US006795776B1

(12) United States Patent
Weinmann et al.

(10) Patent No.: US 6,795,776 B1
(45) Date of Patent: Sep. 21, 2004

(54) CRYSTALLOGRAPHIC STRUCTURE OF THE ANDROGEN RECEPTOR LIGAND BINDING DOMAIN

(75) Inventors: Roberto Weinmann, Lawrenceville, NJ (US); Howard M. Einspahr, Lawrenceville, NJ (US); Stanley R. Krystek, Ringoes, NJ (US); John S. Sack, Lawrenceville, NJ (US); Mark E. Salvati, Lawrenceville, NJ (US); John S. Tokarski, Princeton, NJ (US); Ricardo M. Attar, Lawrenceville, NJ (US); Chihuei Wang, Plainsboro, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 246 days.

(21) Appl. No.: 09/687,609

(22) Filed: Oct. 13, 2000

Related U.S. Application Data

(60) Provisional application No. 60/159,394, filed on Oct. 14, 1999.

(51) Int. Cl.[7] .................. G01N 31/00; G06F 19/00; C07K 1/00; C07J 1/00; A61K 38/22
(52) U.S. Cl. .................. 702/27; 530/350; 530/399; 552/621
(58) Field of Search .................. 702/27; 530/350, 530/399, 386.2; 552/621

(56) References Cited

U.S. PATENT DOCUMENTS 5,463,564 A    10/1995   Agrafiotis et al. .......... 364/496

FOREIGN PATENT DOCUMENTS

| EP | 0 335 628 | 3/1989 |
| WO | WO 97/21993 | 6/1997 |
| WO | WO98/11134 | 3/1998 |
| WO | WO 98/56812 | 12/1998 |
| WO | WO 99/50658 | 10/1999 |

OTHER PUBLICATIONS

Drenth, J. "Principles of Protein X-ray Crystallography" (1994), Springer-Verlag, New York, pp. 1-9.*

Koutsilieris, M. et al. J. of Androl. (1990) vol. 11, No. 1, pp. 2-8.*

Radwan et al. J. Steroid Biochem. (1988) vol. 30, No. 1-6, pp. 251-255.*

Nakahara, M. Hinyokika Kiyo (1986) vol. 32, No. 11, pp. 1689-1699.*

Chang et al. Biochemistry (1982) vol. 21, No. 17, pp. 4102-4109.*

Foekens et al. Mol. Cell Endocrinol. (1981) vol. 23, No. 2, pp. 173-186.*

Tanenbaum et al., Proceedings of the National Acadamy of Sciences of USA, vol. 95, pp. 5998-6003 (1999).

(List continued on next page.)

Primary Examiner—Marjorie Moran
Assistant Examiner—Lori A. Clow
(74) Attorney, Agent, or Firm—Paul D. Golian

(57) ABSTRACT

The first crystal structure of the androgen receptor ligand binding domain has been determined to 2.0 angstrom resolution. Disclosed are the coordinates for the crystal structure, and methods for determining agonists, partial agonists, antagonists, partial antagonists and selective androgen receptors modulators (SARMs) of the androgen receptor.

3 Claims, 3 Drawing Sheets

OTHER PUBLICATIONS

Rossman, M.G., Int. Sci. Rev. Set., vol. 13 (1972).

Bartlett et al., "CAVEAT: A Program to Facilitate the Structure–derived Design of Biologically Active Molecules", *Molecular Recognition in Chemical and Biological Problems Special publication Royal Chem. Soc.* 1989 78:182–196.

Brünger et al., "Crystallographic R. Factor Refinement by Molecular Dynamics", *Science* 1987 235:458–460.

Chang et al., "Structural analysis of complementary DNA and amino acid sequences of human and rat androgen receptors", *Proc. Natl. Acad. Sci. USA* 1988 85:7211–7215.

Goodsell et al., "Automated Docking of Substrates to Proteins by Simulated Annealing", *Proteins: Structure, Function, and Genetics* 1990 8:195–202.

Janknecht R., et al., "Rapid and efficient purification of native histidine–tagged protein expressed by recombinant vaccinia virus" *Proc. Nat. Acad. Sci. USA* 1991 88:8972–8976.

Kuntz et al., "A Geometric Approach to Macromolecule–Ligand Interactions", *J. Mol. Biol.* 1982 161:269–288.

Lattman E., "Use of the Rotation and Translation Functions", *Meth. Enzymol.* 1985 115:55–88.

Martin Y.C., "3D Database Searching in Drug Design", *J. Med. Chem.* 1992 35:2145–2154.

Navaza J., "AMoRe: an Automated Package for Molecular Replacement", *Acta Cryst.* 1994 A50:157–163.

Sack, J.S., "CHAIN—A Crystallographic Modeling Program", *J. Mol. Graphics* 1988 6:224.

Sawyer L., et al., "Data Collection and Processing", *SERC* 1993 56–62.

Wagner et al., "Energetic motion detection", *Nature* 1995 378 (655); 690–697.

Williams, S.P., et al., "Atomic structure of progesterone complexed with its receptor", *Nature* 1998 393: 392–398.

Yanagisawa, et al., "Histamine $H_2$ Receptor Antagonists. 1. Synthesis of N–Cyano and N–Carbamoyl Amidine Derivatives and Their Biological Activities", *J. Med. Chem.* 1984 27:849–857.

* cited by examiner

CRYSTALLOGRAPHIC STRUCTURE OF THE ANDROGEN RECEPTOR LIGAND BINDING DOMAIN

This application claims benefit under 35 U.S.C. section 119(e) to U.S. provisional application No. 60/159,394, filed Oct. 14, 1999.

FIELD OF INVENTION

The present invention relates to compositions and crystals of androgen receptor ligand binding domain optionally in complex with its ligand. This invention also relates to methods of using the structure coordinates of the androgen receptor ligand binding domain/ligand complex to solve the structure of similar or homologous proteins or protein complexes. This invention also relates to methods for designing and selecting ligands that bind to the androgen receptor and methods of using such ligands.

BACKGROUND OF THE INVENTION

The androgen receptor (AR) is a member of the steroid nuclear-receptor superfamily of ligand-dependent transcription factors. The binding of androgen to AR initiates the gene activation required for male sex development.

AR is an important target primarily in two drug discovery areas. In oncology drug discovery, inhibitors (antagonists or partial antagonists) of androgen receptor function are useful for treatment of anti-androgen refractory prostate cancer. In metabolic diseases drug discovery, agonists or partial agonists to the androgen receptor in muscle are useful to treat age-related diseases.

As with the other members of the steroid receptor family, AR has several functional domains including a DNA binding domain (DBD), and a 261 residue ligand-binding domain (LBD) (Mw=30,245 Da) which contains the androgen binding site, and is responsible for switching on the androgen function.

Development of synthetic ligands that specifically bind to androgen receptors has been largely guided by trial and error method of drug design despite the importance of the androgen receptor in physiological processes and medical conditions such as prostate cancer and modulation of reproductive organ modulation. Previously, new ligands specific for androgen receptors were discovered in the absence of information on the three dimensional structure of the androgen receptor with a bound ligand. Before the present invention, researchers were essentially discovering androgen receptor ligands by probing in the dark and without the ability to visualize how the amino acids of the androgen receptor held a ligand in its grasp.

Consequently, it would be advantageous to devise methods and compositions for reducing the time required to discover ligands to the androgen receptor, synthesize such compounds and administer such compounds to organisms to modulate physiological processes regulated by the androgen receptor.

The cDNA and amino acid sequences of human and rat androgen receptors have been described (Proc. Natl. Acad. Sci. U.S.A. 1988 85: 7211–7215). However, there have been no crystals reported of any androgen receptor. Thus, x-ray crystallographic analysis of such proteins has not been possible.

We have discovered the first crystal structure of the androgen receptor ligand binding domain (AR-LBD). Our understanding or the androgen receptor structure has allowed for the determination of the ligand binding site for selective androgen receptor modulators (SARMs).

SUMMARY OF THE INVENTION

The present invention provides crystals of AR-LBD and crystals of an AR-LBD bound to a ligand, i.e. an AR-LBD/AR-LBD ligand complex. Most preferably the AR-LBD ligand is dihydrotestosterone (DHT). Thus, the present invention is directed to a crystal of an AR-LBD comprising:

1) an AR-LBD and an AR-LBD ligand or
2) an AR-LBD without an AR-LBD ligand;

wherein said crystal diffracts to at least 3 angstrom resolution and has a crystal stability within 5% of its unit cell dimensions. The crystal of AR or AR-LBD preferably has at least 200 amino acid and preferably comprises amino acid sequence 672 to 917 of rat AR or the AR amino acid sequence 672 to 917 of human AR.

The present invention also provides the structure coordinates of the AR-LBD/AR-LBD ligand complex. The complete coordinates are listed in Table A.

The present invention also provides a method for determining at least a portion of the three-dimensional structure of molecules or molecular complexes which contain at least some structurally similar features to the androgen receptor ligand binding domain. It is preferred that these molecules or molecular complexes comprise at least a part of the ligand binding site defined by structure coordinates of AR-LBD amino acids V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787,1869, L873, H874, F876, T877 and F878 according to Table A, or a mutant or homologue thereof. Since the protein sequences for rat and human AR LBD are identical, the human numbering system was used herein.

The present invention also provides a machine-readable data storage medium which comprises a data storage material encoded with machine readable data defined by the structure coordinates of an AR-LBD/AR-LBD ligand or ligand complex according to Table A or a homologue of the complex.

The present invention further provides a binding site in AR-LBD for an AR-LBD ligand as well as methods for designing or selecting AR modulators including agonists, partial agonists, antagonists, partial antagonists and/or selective androgen receptor modulators (SARMs) of AR using information about the crystal structures disclosed herein.

DETAILED DESCRIPTION OF THE INVENTION

Figure 1:
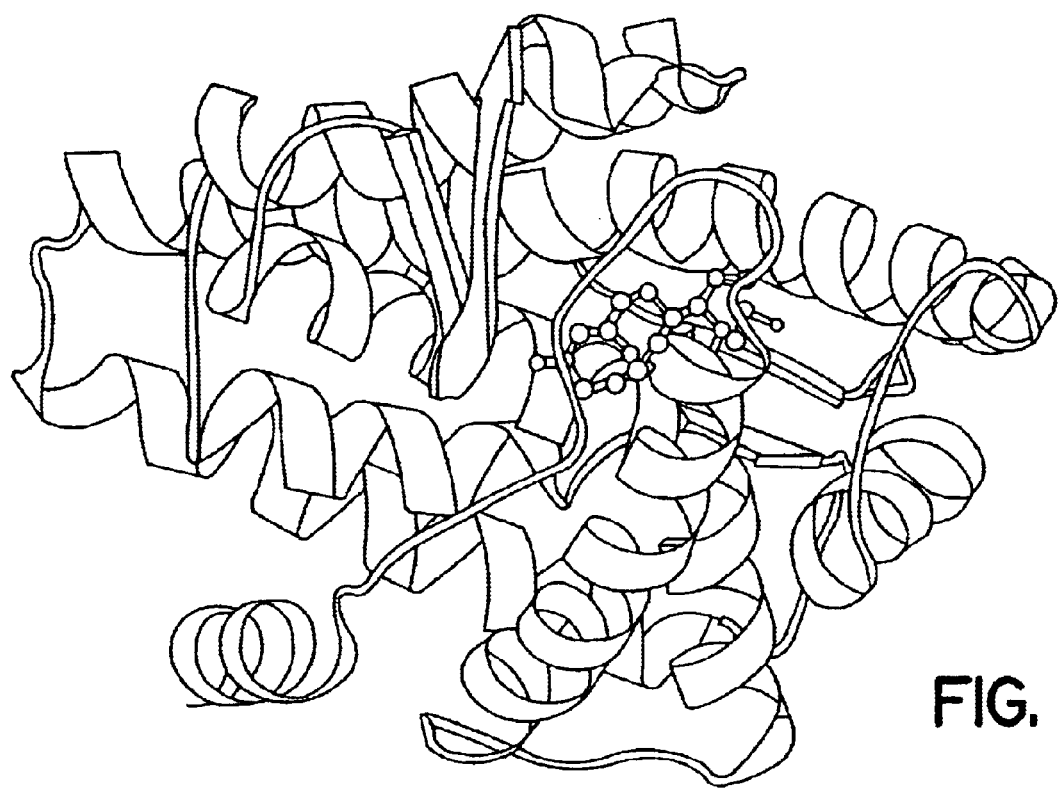
FIG. 1 is a ribbon style drawing of the Androgen Receptor LBD. The substrate DHT is shown as a ball-and-stick figure.
Figure 2:
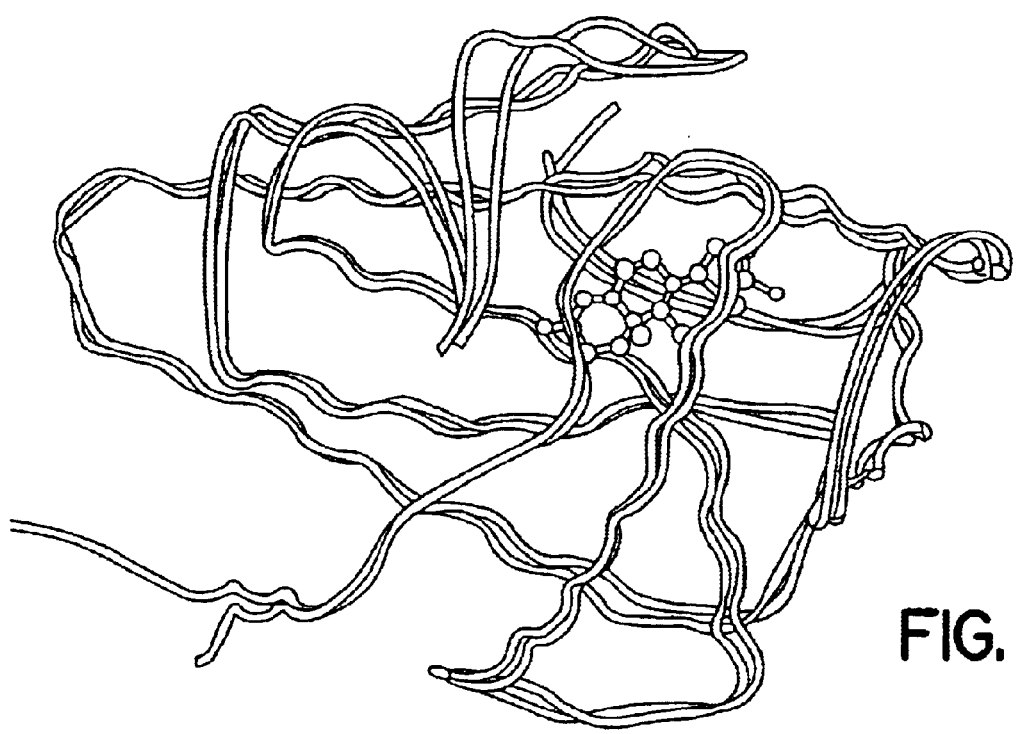
FIG. 2 is a comparison of the androgen receptor ligand binding domain with progesterone receptor ligand binding domain.

The first crystal structure of the androgen receptor ligand binding domain (AR-LBD) has been determined to 2.0 Å resolution. Crystals of rat AR-LBD were grown from precipitating solutions containing 0.9 M Sodium Tartrate, 0.1 M Na Hepes, pH 7.5. X-ray diffraction from the crystals have the symmetry and systematic absences of the orthorhombic space group P212121 with unit cell dimensions a=56.03 Å, b=66.27 Å, c=70.38 Å, and one molecule per asymmetric unit (Mathews Volume=2.16 Å$^3$ Da$^{-1}$). The structure was determined by the method of molecular replacement using the structure of the Progesterone Receptor LBD (PR-LBD) as the search model.

The complex of AR-LBD with dihydrotestosterone (DHT) shows the mode of binding of the steroid to the receptor in the agonist conformation.

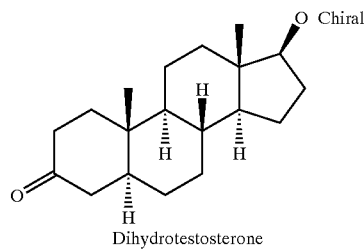

Dihydrotestosterone

The following abbreviations are used throughout the application:
A=Ala=Alanine
V=Val=Valine
L=Leu=Leucine
I=Ile=Isoleucine
P=Pro=proline
F=Phe=phenylalanine
W=Trp=Tryptophan
M=Met=Methionine
G=Gly=Glycine
S=Ser=Serine
T=Thr=Threonine
C=Cys=Cysteine
Y=Tyr=Tyrosine
N=Asn=Asparagine
Q=Gln=Glutamine
D=Asp=Aspartic Acid
E=GIu=Glutamic Acid
K=Lys=Lysine
R=Arg=Arginine
H=His=Histidine
"Atom type" refers to the element whose coordinates have been determined. Elements are defined by the first letter in the column.
"X, Y, Z" crystallographically define the atomic position determined for each atom.
"B" is a thermal factor that measures movement of the atom around its atomic center.
"Occ" is an occupancy factor that refers to the fraction of the molecules in which each atom occupies the position specified by the coordinates. A value of "1" indicates that each atom has the same conformation, i.e., the same position, in all molecules of the crystal.
Additional definitions are set forth in the specification where necessary.

The androgen receptor (AR) described herein is intended to include any polypeptide which has the activity of the naturally occurring androgen receptor. The AR and AR-LBD contemplated herein includes all vertebrate and mammalian forms such as rat, mouse, pig, goat, horse, guinea pig, rabbit, monkey, orangutan and human. Such terms also include polypeptides that differ from naturally occurring forms of AR and AR-LBD by having amino acid deletions, substitutions, and additions, but which retain the activity of AR and AR-LBD, respectively. The crystal structure of the invention preferably contains at least 25%, more preferably at least 50%, more preferably at least 75%, more preferably at least 90%, more preferably at least 95%, more preferably at least 99%, and most preferably all of the coordinates listed in Table A. The crystal of the AR-LBD/AR-LBD ligand of the invention preferably has the following unit cell dimensions in angstroms: a=56.03±5%, b=66.27±5%, c=70.38±5% and an orthorhombic space group P212121.

The AR-LBD ligand of this invention is any peptide, peptide mimetic or nonpeptide, including small organic molecules, that is capable of acting as a ligand for AR-LBD. In a preferred embodiment, the AR-LBD ligand is an AR modulator. By "AR modulator" it is meant an agonist or activator, a partial agonist or partial activator, an antagonist or inhibitor, or a partial antagonist or partial inhibitor which demonstrates tissue specific activations of the AR. Such compounds are also referred to herein as SARMs (selective androgen receptor modulators) of the AR-LBD. Examples of preferred agonists include androgens such as dihydrotestosterone.

The peptides referred to herein (e.g., AR, AR-LBD, and the like) may be produced by any well-known method, including synthetic methods, such as solid phase, liquid phase and combination solid phase/liquid phase syntheses; recombinant DNA methods, including cDNA cloning, optionally combined with site directed mutagenesis; and/or purification of the natural products, optionally combined with enzymatic cleavage methods to produce fragments of naturally occurring.

Advantageously, the crystallizable compositions provided by this invention are amenable to x-ray crystallography. Thus, this invention also provides the three-dimensional structure of the AR-LBD/AR-LBD ligand complex, particularly the complex of rat AR-LBD with dihydrotestosterone.

The three-dimensional structure of the AR-LBD/ dihydrotestosterone complex of this invention is defined by a set of structure coordinates as set forth in Table A. The term "structure coordinates" refers to Cartesian coordinates derived from mathematical equations related to the patterns obtained on diffraction of a monochromatic beam of X-rays by the atoms (scattering centers) of an androgen receptor/ dihydrotestosterone complex in crystal form. The diffraction data are used to calculate an electron density map of the repeating unit of the crystal. The electron density maps are then used to establish the positions of the individual atoms of the complex.

Those of skill in the art will understand that a set of structure coordinates for a receptor or receptor/ligand complex or a portion thereof, is a relative set of points that define a shape in three dimensions. Thus, it is possible that an entirely different set of coordinates could define a similar or identical shape. Moreover, slight variations in the individual coordinates will have little effect on overall shape.

The variations in coordinates discussed above may be generated because of mathematical manipulations of the structure coordinates. For example, the structure coordinates set forth in Table A could be manipulated by crystallographic permutations of the structure coordinates, fractionalization of the structure coordinates; integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within an acceptable standard error as compared to the original coordinates, the resulting three-dimensional shape is considered to be the same.

Various computational analyses are therefore necessary to determine whether a molecule or molecular complex or a portion thereof is sufficiently similar to all or parts of the androgen receptor/dihydrotestosterone described above as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: 1) load the structures to be compared; 2) define the atom equivalences in these structures; 3) perform a fitting operation; and 4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, Cs, C and O) for all conserved residues between the two structures being compared. We will also consider only rigid fitting operations.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any molecule or molecular complex that has a root mean square deviation of conserved residue backbone atoms (N, Cα, C, O) of less than 1.5 Å when superimposed on the relevant backbone atoms described by structure coordinates listed in Table A are considered identical. More preferably, the root mean square deviation is less than 1.0 Å. In a preferred embodiment of the present invention, the molecule or molecular complex comprises at least a portion of the ligand binding site defined by structure coordinates of AR-LBD amino acids V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877 and F878 according to Table A, or a mutant or homologue of said molecule or molecular complex. More preferred are molecules or molecular complexes comprising all or any part of the ligand binding site defined by structure coordinates of AR-LBD amino acids N705, Q711, R752, F764 and T877 according to Table A, or a mutant or homologue of said molecule or molecular complex. Since the protein sequences for rat and human AR LBD are identical, the human numbering system has been used herein.

The term "complex" or "molecular complex" means AR-LBD or a mutant or homologue of AR-LBD in a covalent or non-covalent association with a chemical entity or compound.

For purposes of the present invention, by "at least a portion of" it is meant all or any part of the ligand binding site defined by these structure coordinates.

By "mutant or homologue" as used herein it is meant a molecule or molecular complex having a similar structure and/or sequences to AR-LBD. By "similar structure" it is meant a mutant or homologue having a binding pocket that has a root mean square deviation from the backbone atoms of said AR-LBD amino acids of not more than 1.5 Angstroms. By "similar sequence" it is meant a mutant or homologue having 30%, or more preferably 75%, identity with AR-LBD.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein or protein complex from the relevant portion of the backbone of the AR portion of the complex as defined by the structure coordinates described herein.

Once the structure coordinates of a protein crystal have been determined they are useful in solving the structures of other crystals.

Thus, in accordance with the present invention, the structure coordinates of an androgen receptor/ dihydrotestosterone complex, and in particular a complex, and portions thereof is stored in a machine-readable storage medium. Such data may be used for a variety of purposes, such as drug discovery and x-ray crystallographic analysis or protein crystal.

Accordingly, in one embodiment of this invention is provided a machine-readable data storage medium comprising a data storage material encoded with the structure coordinates set forth in Table A.

One embodiment utilizes System 10 as disclosed in WO 98/11134, the disclosure of which is incorporated herein by reference in its entirety.

For the first time, the present invention permits the use of structure-based or rational drug design techniques to design, select, and synthesize chemical entities, including inhibitory and stimulatory compounds that are capable of binding to AR-LBD, or any portion thereof.

One particularly useful drug design technique enabled by this invention is iterative drug design. Iterative drug design is a method for optimizing associations between a protein and a compound by determining and evaluating the three-dimensional structures of successive sets of protein/compound complexes.

Those of skill in the art will realize that association of natural ligands or substrates with the binding pockets of their corresponding receptors or enzymes is the basis of many biological mechanisms of action. The term "binding pocket" as used herein, refers to a region of a molecule or molecular complex, that, as a result of its shape, favorably associates with another chemical entity or compound. Similarly, many drugs exert their biological effects through association with the binding pockets of receptors and enzymes. Such associations may occur with all or any parts of the binding pockets. An understanding of such associations will help lead to the design of drugs having more favorable associations with their target receptor or enzyme, and thus, improved biological effects. Therefore, this information is valuable in designing potential ligands or inhibitors of receptors or enzymes, such as inhibitors of AR.

The term "associating with" refers to a condition of proximity between chemical entities or compounds, or portions thereof. The association may be non-covalent—wherein the juxtaposition is energetically favored by hydrogen bonding or van der Waals or electrostatic interactions—or it may be covalent.

In iterative drug design, crystals of a series of protein/compound complexes are obtained and then the three-dimensional structures of each complex is solved. Such an approach provides insight into the association between the proteins and compounds of each complex. This is accomplished by selecting compounds with inhibitory activity, obtaining crystals of this new protein/compound complex, solving the three dimensional structure of the complex, and comparing the associations between the new protein/compound complex and previously solved protein/compound complexes. By observing how changes in the compound affected the protein/compound associations, these associations may be optimized.

In some cases, iterative drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex.

As used herein, the term "soaked" refers to a process in which the crystal is transferred to a solution containing the compound of interest.

The structure coordinates set forth in Table A can also be used to aid in obtaining structural information about another crystallized molecule or molecular complex. This may be achieved by any of a number of well-known techniques, including molecular replacement.

The structure coordinates set forth in Table A can also be used for determining at least a portion of the three-dimensional structure of molecules or molecular complexes which contain at least some structurally similar features to AR. In particular, structural information about another crystallized molecule or molecular complex may be obtained. This may be achieved by any of a number of well-known techniques, including molecular replacement.

Therefore, in another embodiment this invention provides a method of utilizing molecular replacement to obtain structural information about a crystallized molecule or molecular complex whose structure is unknown comprising the steps of:
a) generating an X-ray diffraction pattern from said crystallized molecule or molecular complex;
b) applying at least a portion of the structure coordinates set forth in Table A to the X-ray diffraction pattern to generate a three-dimensional electron density map of the molecule or molecular complex whose structure is unknown; and
c) using all or a portion of the structure coordinates set forth in Table A to generate homology models of AR-LBD or any other nuclear hormone receptor ligand binding domain.

Preferably, the crystallized molecule or molecular complex is obtained by soaking a crystal of this invention in a solution.

By using molecular replacement, all or part of the structure coordinates of the AR-LBD/AR-LBD ligand complex provided by this invention or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of the AR-LBD/AR-LBD ligand complex according to Table A within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55–77 (1985); M. G. Rossmann, ed., "The Molecular Replacement Method", Int. Sci. Rev. Set., No. 13, Gordon & Breach, New York (1972)].

The structure of any portion of any crystallized molecule or molecular complex, or mutant, homologue or orphan receptor that is sufficiently homologous to any portion of the AR-LBD/AR-LBD ligand complex can be solved by this method. Along with the aforementioned AR, there also exist a number of AR for which the activating or deactivating ligands may not be characterized. These proteins are classified as AR due to strong sequence homology to other AR, and are known as orphan receptors.

The structure coordinates are also particularly useful to solve the structure of crystals of AR-LBD/AR-LBD ligand co-complexed with a variety of chemical entities. This approach enables the determination of the optimal sites for interaction between chemical entities, including interaction of candidate AR inhibitors with the complex. For example, high resolution X-ray diffraction data collected from crystals exposed to different types of solvent allows the determination of where each type of solvent molecule resides. Small molecules that bind tightly to these sites can then be designed and synthesized and tested for their AR inhibition activity.

All of the complexes referred to above may be studied using well-known X-ray diffraction techniques and may be refined versus 1.5–3 A resolution X-ray data to an R value of about 0.20 or less using computer software, such as X-PLOR [Yale University, 1992, distributed by Molecular Simulations, Inc.; see, e.g., Blundell & Johnson, supra; Meth. Enzymol., vol. 114 & 115, H. W. Wyckoff et al., eds., Academic Press (1985)]. This information may thus be used to optimize known AR agonists, partial agonists, antagonists, partial antagonists and SARMS, and more importantly, to design new AR agonists/antagonists.

Accordingly, the present invention is also directed to a binding site in AR-LBD for an AR-LBD ligand in which a portion of AR-LBD ligand is in van der Walls contact or hydrogen bonding contact with at least one of the following residues: V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877, F878, L880, L881, V889, F891, P892, E893, M894, M895, A896, E897, I898, I899, S900, V901, Q902, V903, P904 or I906 of AR-LBD. For purposes of this invention, by AR-LBD binding site it is also meant to include mutants or homologues thereof. In a preferred embodiment, the mutants or homologues have at least 25% identity, more preferably 50% identity, more preferably 75% identity, and most preferably 95% identity to residues V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877, F878, L880, L881, V889, F891, P892, E893, M894, M895, A896, E897, I898, I899, S900, V901, Q902, V903, P904 or I906 of AR-LBD binding sites.

The present invention is also directed to a machine-readable data storage medium, comprising a data storage material encoded with machine readable data, wherein the data is defined by the structure coordinates of an AR-LBD/AR-LBD ligand according to Table A or a homologue of said complex, wherein said homologue comprises backbone atoms that have a root mean square deviation from the backbone atoms of the complex of not more than 3.0 Å. Preferably, the machine-readable data storage medium, according to the invention, is wherein said molecule or molecular complex is defined by the set of structure coordinates for AR-LBD/AR-LBD ligand according to Table A, or a homologue of said molecule or molecular complex, said homologue having a root mean square deviation from the backbone atoms of said amino acids of not more than 2.0 Å. In a preferred embodiment the machine-readable data storage medium comprises a data storage material encoded with a first set of machine readable data comprising a Fourier transform of at least a portion of the structural coordinates for an AR-LBD/AR-LBD ligand according to Table A; which, when combined with a second set of machine readable data comprising an X-ray diffraction pattern of a molecule or molecular complex of unknown structure, using a machine programmed with instructions for using said first set of data and said second set of data, can determine at least a portion of the structure coordinates corresponding to the second set of machine readable data, said first set of data and said second set of data.

The present invention also provides for computational methods using three dimensional models of the androgen receptor that are based on crystals of AR-LBD/AR-LBD ligand complex. Generally, the computational method of designing an androgen receptor ligand determines which amino acid or amino acids of the AR-LBD interact with a chemical moiety (at least one) of the ligand using a three dimensional model of a crystallized protein comprising the AR-LBD with a bound ligand, and selecting a chemical modification (at least one) of the chemical moiety to produce a second chemical moiety with a structure that either decreases or increases an interaction between the interacting amino acid and the second chemical moiety compared to the interaction between the interacting amino acid and the corresponding chemical moiety on the natural hormone.

The computational methods of the present invention are for designing androgen receptor synthetic ligands using such crystal and three dimensional structural information to generate synthetic ligands that modulate the conformational changes of the androgen receptor's LBD. These computational methods are particularly useful in designing an agonist, partial agonist, antagonist or partial antagonist or SARMs to the androgen receptor, wherein the agonist, partial agonist, antagonist or partial antagonist or SARMS has an extended moiety that prevents any one of a number of ligand-induced molecular events that alter the receptor's influence on the regulation of gene expression, such as preventing the normal coordination of the activation domain observed for a naturally occurring ligand or other ligands that mimic the naturally occurring ligand, such as an agonist. As described herein, synthetic ligands of the androgen receptor will be useful in modulating androgen receptor activity in a variety of medical conditions.

AR is known to comprise various domains as follows:
1) a variable amino-terminal domain;
2) a highly conserved DNA-binding domain (DBD); and
3) a less conserved carboxyl-terminal ligand-binding domain (LBD).

This modularity permits different domains of each protein to separately accomplish different functions, although the domains can influence each other. The separate function of a domain is usually preserved when a particular domain is isolated from the remainder of the protein. Using conventional protein chemistry techniques a modular domain can sometimes be separated from the parent protein. Using conventional molecular biology techniques each domain can usually be separately expressed with its original function intact or chimerles of two different nuclear receptors can be constructed, wherein the chimetics retain the properties of the individual functional domains of the respective nuclear receptors from which the chimerica were generated.

Amino Terminal Domain

The amino terminal domain is the least conserved of the three domains. This domain is involved in transcriptional activation and in some cases its uniqueness may dictate selective receptor-DNA binding and activation of target genes by specific receptor isoforms. This domain can display synergistic and antagonistic interactions with the domains of the LBD. For example, studies with mutated and/or deleted receptors show positive cooperativity of the amino and carboxy terminal domains. In some cases, deletion of either of these domains will abolish the receptor's transcriptional activation functions.

DNA-Binding Domain

The DBD is the most conserved domain. The DBD contains two perpendicularly oriented a-helixes that extend from the base of the first and second zinc fingers. The two zinc fingers function in concert along with non-zinc finger residues to direct nuclear receptors to specific target sites on DNA and to align receptor homodimer or heterodimer interfaces. Various amino acids in DBD influence spacing between two half-sites for receptor dimer binding.

Ligand or AR Binding Domain

The LBD is the second most highly conserved domain. Whereas integrity of several different LBD sub-domains is important for ligand binding, truncated molecules containing only the LBD retain normal ligand-binding activity. This domain also participates in other functions, including dimerization, nuclear translocation and transcriptional activation. Importantly, this domain is the binding site for ligands, i.e. AR modulators, and undergoes ligand-induced conformational changes as detailed herein.

As described herein, the LBD of AR can be expressed, crystallized, its three dimensional structure determined with a ligand bound (either using crystal data from the same receptor or a different receptor or a combination thereof), and computational methods used to design ligands to its LBD, particularly ligands that contain an extension moiety that coordinates the activation domain of AR.

Once a computationally designed ligand (CDL) is synthesized, it can be tested using assays to establish its activity as an agonist, partial agonist, antagonist or partial antagonist or SARM, and affinity, as described herein. After such testing, the CDLs can be further refined by generating LBD crystals with a CDL bound to the LBD. The structure of the CDL can then be further refined using the chemical modification methods described herein for three dimensional models to improve the activity or affinity of the CDL and make second generation CDLs with improved properties, such as that of a super agonist or antagonist.

Typically AR-LBD is purified to homogeneity for crystallization. Purity of AR-LBD is measured with SDS-PAGE, mass spectrometry and hydrophobic HPLC. The purified AR for crystallization should be at least 97.5% pure or 97.5%, preferably at least 99.0% pure or 99.0% pure, more preferably at least 99.5% pure or 99.5% pure.

Initially purification of the unliganded receptor can be obtained by conventional techniques, such as hydrophobic interaction chromatography (HPLC), ion exchange chromatography (HPLC), and heparin affinity chromatography.

To achieve higher purification for improved crystals of AR, it will be desirable to ligand shift purify the nuclear receptor using a column that separates the receptor according to charge, such as an ion exchange or hydrophobic interaction column, and then bind the eluted receptor with a ligand, especially an agonist or partial agonist. The ligand induces a change in the receptor's surface charge such that when re-chromatographed on the same column, the receptor then elutes at the position of the liganded receptor are removed by the original column run with the unliganded receptor. Usually saturating concentrations of ligand are used in the column and the protein can be preincubated with the ligand prior to passing it over the column.

More recently developed methods involve engineering a "tag" such as with histidine placed on the end of the protein, such as on the amino terminus, and then using a nickle chelation column for purification, Janknecht R., Proc. Natl. Acad.Sci. USA Vol 88:8972–8976 (1991) incorporated by reference.

To determine the three dimensional structure of a AR-LBD, it is desirable to co-crystalize the LBD with a corresponding LBD ligand.

Typically purified AR-LBD is equilibrated at a saturating concentration of ligand at a temperature that preserves the integrity of the protein. Ligand equilibration can be established between 2 and 37° C., although the receptor tends to be more stable in the 2–20° C. range.

Preferably crystals are made with the hanging drop methods. Regulated temperature control is desirable to improve crystal stability and quality. Temperatures between 4 and 25° C. are generally used and it is often preferable to test crystallization over a range of temperatures. It is preferable to use crystallization temperatures from 18 to 25° C., more preferably 20 to 23° C., and most preferably 22° C.

Ligands that interact with AR can act as an agonist, partial agonist, antagonist or partial antagonist or SARM based on what ligand-induced conformational changes take place.

Agonists or partial agonists induce changes in receptors that place them in an active conformation that allows them to influence transcription, either positively or negatively. There may be several different ligand-induced changes in the receptor's conformation.

Antagonists or partial antagonists bind to receptors, but fail to induce conformational changes that alter the receptor's transcriptional regulatory properties or physiologically telcram conformations. Binding of an antagonist or partial antagonist can also block the binding and therefore the actions of an agonist or partial agonist.

Partial agonists, or partial antagonists, bind to receptors and induce only part of the changes in the receptors that are induced by agonists or antagonists, respectively. The differences can be qualitative or quantitative. Thus, a partial agonist or partial antagonist may induce some of the conformation changes induced by agonists or antagonists, respectively, but not others, or it may only induce certain changes to a limited extent.

As described herein, the unliganded receptor is in a configuration that is either inactive, has some activity or has repressor activity. Binding of agonist ligands induces conformational changes in the receptor such that the receptor becomes more active, either to stimulate or repress the expression of genes. The receptors may also have non-genomic actions, some of the known types of changes and/or the sequelae of these are listed herein.

Heat shock protein binding domains present a region for binding to the LBD and can be modulated by the binding of a ligand to the LBD. Consequently, an extended chemical moiety (or more) from the ligand that stabilizes the binding or comact of the heat shock protein binding domain with the LBD can be designed. Typically such chemical moieties will extend past and away from the molecular recognition domain on the ligand and usually past the buried binding cavity of the ligand.

Ligand binding by the receptor is a dynamic process, which regulates receptor function by inducing an altered conformation.

The three-dimensional structure of the liganded AR receptor will greatly aid in the development of new AR synthetic ligands. In addition, AR is overall well suited to modern methods including three-dimensional structure elucidation and combinatorial chemistry such as those disclosed in EP 335 628, U.S. Pat. No. 5,463,564, which are incorporated herein by reference. Computer programs that use crystallography data when practicing the present invention will enable the rational design of ligand to AR. Programs such as RASMOL can be used with the atomic coordinates from crystals generated by practicing the invention or used to practice the invention by generating three dimensional models and/or determining the structures involved in ligand binding. Computer programs such as INSIGHT and GRASP allow for further manipulation and the ability to introduce new structures. In addition, high throughput binding and bioactivity assays can be devised using purified recombinant protein and modern reporter gene transcription assays described herein and known in the art in order to refine the activity of a CDL.

Generally the computational method of designing an AR synthetic ligand comprises two steps:

1) determining which amino acid or amino acids of AR-LBD interacts with a first chemical moiety (at least one) of the ligand using a three dimensional model of a crystallized protein comprising an AR-LBD with a bound ligand; and 2) selecting a chemical modifications (at least one) of the first chemical moiety to produce a second chemical moiety with a structure to either decrease or increase an interaction between the interacting amino acid and the second chemical moiety compared to the interaction between the interacting amino acid and the first chemical moiety.

Preferably the method is carried out wherein said three dimensional model is generated by comparing isomorphous ligand derivatives to produce improved phasing. Further preferred is wherein said method comprises determining a change in interaction between said interacting amino acid and said ligand after chemical modification of said first chemical moiety, especially wherein said three dimensional model is generated by comparing isomorphous ligand derivatives to produce improved phasing. Also preferred is wherein said selecting uses said first chemical moiety that interacts with at least one of the interacting amino acids V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877, F878, L880, L881, V889, F891, P892, E893, M894, M895, A896, E897, I898, I899, S900, V901, Q902, V903, P904 or I906.

As shown herein, interacting amino acids form contacts with the ligand and the center of the atoms of the interacting amino acids are usually 2 to 4 angstroms away from the center of the atoms of the ligand. Generally these distances are determined by computer as discussed herein and in McRee 1993, however distances can be determined manually once the three dimensional model is made. See also Wagner et al., Nature 378(6558):670–697 (1995) for stereochemical figures of -three dimensional models. More commonly, the atoms of the ligand and the atoms of interacting amino acids are 3 to 4 angstroms apart. The invention can be practiced by repeating steps I and 2 to refine the fit of the ligand to the LBD and to determine a better ligand, such as an agonist, partial agonist, antagonist or partial antagonist or SARM. The three dimensional model of AR can be represented in two dimensions to determine which amino acids contact the ligand and to select a position on the ligand for chemical modification and changing the interaction with a particular amino acid compared to that before chemical modification. The chemical modification may be made using a computer, manually using a two dimensional representation of the three dimensional model or by chemically synthesizing the ligand. The ligand can also interact with distant amino acids after chemical modification of the ligand to create a new ligand. Distant amino acids are generally not in contact with the ligand before chemical modification. A chemical modification can change the structure of the ligand to make as new ligand that interacts with a distant amino acid usually at least 4.5 angstroms away from the ligand, preferably wherein said first chemical moiety is 6 to 12 angstroms away from a distant amino acid. Often distant amino acids will not line the surface of the binding cavity for the ligand, they are too far away from the ligand to be part of a pocket or binding cavity. The interaction between a LBD amino acid and an atom of an LBD ligand can be made by any force or attraction described in nature. Usually the interaction between the atom of the amino acid and the ligand will be the result of a hydrogen bonding interaction, charge interaction, hydrophobic interaction, van der Waals interaction or dipole interaction. In the case of the hydrophobic interaction it is recognized that this is not a per se interaction between the amino acid and ligand, but rather the usual result, in part, of the repulsion of water or other hydrophilic group from a hydrophobic surface. Reducing or enhancing the interaction of the LBD and a ligand can be measured by calculating or testing binding energies, computationally or using thermodynamic or kinetic methods as known in the art.

Chemical modifications will often enhance or reduce interactions of an atom of a LBD amino acid and an atom of an LBD ligand. Steric hindrance will be a common means of changing the interaction of the LBD binding cavity with the activation domain.

The present invention also provides methods for identifying compounds that modulate androgen receptor activity. Various methods or combinations thereof can be used to identify these compounds. For example, test compounds can be modeled that fit spatially into the AR-LBD as defined by structure coordinates according to Table A, or using a three-dimensional structural model of AR-LBD, mutant AR-LBD or AR-LBD homolog or portion thereof. Structure coordinates of the ligand binding site, in particular amino acids V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877, F878, L880, L881, V889, F891, P892, E893, M894, M895, A896, E897, I898, I899, S900, V901, Q902, V903, P904 or I906 can also be used to identify structural and chemical features. Identified structural or chemical features can then be employed to design or select compounds as potential AR modulators. By structural and chemical features it is meant to include, but is not limited to, van der Waals interactions, hydrogen bonding interactions, charge interaction, hydrophobic bonding interaction, hydrophobic interaction and dipole interaction. Alternatively, or in conjunction, the three-dimensional structural model or the ligand binding site can be employed to design or select compounds as potential AR modulators. Compounds identified as potential AR modulators can then be synthesized and screened in an assay characterized by binding of a test compound to the AR-LBD. Examples of assays useful in screening of potential AR modulators include, but are not limited to, screening in silico, in vitro assays and high throughput assays. Finally, these methods may also involve modifying or replacing one or more amino acids from AR-LBD such as V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877, F878, L880, L881, V889, F891, P892, E893, M894, M895, A896, E897, I898, I899, S900, V901, Q902, V903, P904 or I906 of AR-LBD according to Table A.

A preferred method of the invention can be described as a computational method of designing an androgen receptor antagonist from an androgen receptor agonist comprising:

1) determining a structure of a molecular recognition domain of said agonist using a three dimensional model of a crystallized protein comprising an AR-LBD, and
2) selecting at least one chemical modification of said agonist that provides a ligand structure that extends beyond a binding site for said agonist and in the direction of at least one protein domain important in AR biological function.

Another preferred method of the invention can be described as a computational method of designing a selective androgen receptor modulator such as an androgen receptor super agonist or antagonist comprising:

1) determining at least one interacting amino acid of an AR-LBD that interacts with at least one first chemical moiety of said ligand using a three dimensional model of a crystallized protein comprising AR-LBD with a bound ligand, and
2) selecting at least one chemical modification of said first chemical moiety to produce a second chemical moiety with a structure to reduce or enhance an interaction between said interacting amino acid and said second chemical moiety compared to said interaction between said interacting amino acid and said first chemical moiety.

However, as will be understood by those of skill in the art upon this disclosure, other structure based design methods can be used. Various computational structure based design methods have been disclosed in the art.

For example, a number computer modeling systems are available in which the sequence of the AR-LBD and the AR-LBD structure (i.e., atomic coordinates of AR-LBD and/or the atomic coordinates of the active site, the bond and dihedral angles, and distances between atoms in the active site such as provided in Table A) can be input. This computer system then generates the structural details of the site in which a potential AR modulator binds so that complementary structural details of the potential modulators can be determined. Design in these modeling systems is generally based upon the compound being capable of physically and structurally associating with AR-LBD. In addition, the compound must be able to assume a conformation that allows it to associate with AR-LBD. Some modeling systems estimate the potential inhibitory or binding effect of a potential AR modulator prior to actual synthesis and testing.

Methods for screening chemical entities or fragments for their ability to associate with AR-LBD are also well known. Often these methods begin by visual inspection of the active site on the computer screen. Selected fragments or chemical entities are then positioned with the AR-LBD. Docking is accomplished using software such as QUANTA and SYBYL, following by energy minimization and molecular dynamics with standard molecular mechanic forcefields such as CHARMM and AMBER. Examples of computer programs which assist in the selection of chemical fragment or chemical entities useful in the present invention include, but are not limited to, GRID (Goodford, P. J. J. Med. Chem. 1985 28:849–857), AUTODOCK (Goodsell, D. S. and Olsen, A. J. Proteins, Structure, Functions, and Genetics 1990 8:195–202), and DOCK (Kunts et al. J. Mol. Biol. 1982 161:269–288).

Upon selection of preferred chemical entities or fragments, their relationship to each other and AR-ABD can be visualized and the entities or fragments can be assembled into a single potential modulator. Programs useful in assembling the individual chemical entities include, but are not limited to CAVEAT (Bartlett et al. Molecular Recognition in Chemical and Biological Problems Special Publication, Royal Chem. Soc. 78, 182–196 (1989) ) and 3D Database systems (Martin, Y. C. J. Med. Chem. 1992 35:2145–2154).

Alternatively, compounds may be designed de novo using either an empty active site or optionally including some portion of a known inhibitor. Methods of this type of design include, but are not limited to LUDI (Bohm H-J, J. Comp. Aid. Molec. Design 1992 6:61–78) and LeapFrog (Tripos Associates, St. Louis. Mo.).

The present invention is also directed to an AR-LBD selective androgen receptor modulator (SARM), in particular an agonist or antagonist or partial agonist or partial antagonist, identified by a computational process of the invention.

The present invention is further directed to a method for treating prostate cancer comprising administering an effective amount of an AR modulator, preferably an antagonist or partial antagonist, identified by a computational process of the invention.

The present invention is also direct to a method for treating an age related disease comprising administering an effective amount of an AR modulator, preferably an agonist or partial agonist, identified by a computational process of the invention, preferably wherein said age related disease is osteoporosis, muscle wasting or loss of libido.

Compounds identified as agonists, partial agonists, antagonists, partial antagonists or SARMs by the methods disclosed herein which are active when given orally can be formulated as liquids for example syrups, suspensions or emulsions, tablets, capsules and lozenges. A liquid composition will generally consist of a suspension or solution of the compound in a suitable liquid carrier(s), for example ethanol, glycerin, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder. For example a powder containing active compound, suspending agent, sucrose and a sweetener can be reconstituted with water to form a suspension; and a syrup can be prepared from a powder containing active ingredient, sucrose and a sweetener. A composition in the form of a tablet can be prepared using any suitable pharmaceutical carrier(s) routinely used for preparing solid compositions. Examples of such carriers include magnesium stearate, starch, lactose, sucrose, microcrystalline cellulose, binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix. A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule. Compounds identified by the processes described herein which are active when given parenterally can be formulated for intramuscular or intravenous administration. A typical composition for intramuscular administration will consist of a suspension or solution of active ingredient in an oil, for example arachis oil or sesame oil. A typical composition for intravenous administration will consist of a sterile isotonic aqueous solution containing, for example active ingredient, dextrose, sodium chloride, a co-solvent, for example polyethylene glycol and, optionally, a chelating agent, for example ethylenediaminetetracetic acid and an anti-oxidant, for example, sodium metabisulphite. Alternatively, the solution can be freeze dried and then reconstituted with a suitable solvent just prior to administration. Identified compounds which are active on rectal administration can be formulated as suppositories. A typical suppository formulation will generally consist of active ingredient with a binding and/or lubricating agent such as a gelatin or cocoa butter or other low melting vegetable or synthetic wax or fat. Identified compounds which are active on topical administration can be formulated as transdermal compositions. Such compositions include, for example, a backing, active compound reservoir, a control membrane, liner and contact adhesive. The typical daily dose of a varies according to individual needs, the condition to be treated and with the route of administration. Suitable doses are in the general range of from 0.001 to 10 mg/kg bodyweight of the recipient per day.

The following examples are to illustrate the invention, but should not be interpreted as a limitation thereon.

EXAMPLES

Cloning, Expression and Purification of the Androgen Receptor Ligand-Binding Domain The rat androgen receptor (rAR) ligand-binding domain (LBD) cDNA, from amino acid 646 to 901, was cloned from a rat prostate cDNA library (Clontech) by PCR. The primers used were CATATGATTGAAGGCTATGAATGTCAAC-CTATCTTT (SEQ ID NO:3) and TCACTGTGTGTG-GAAATAGATGG (SEQ ID NO:4). The rat AR LBD was expressed as a fusion protein driven by the T7 promoter of pET28b vector (Novagen) to include an N-terrninal polyhistidine tag and a thrombin cleavage site. The replacement of T877 for A (the LNCaP mutation) in this rAR LBD expression construct was performed with the QuickChange Site-Directed Mutagenesis kit (STRATAGENE). Dihydrotestosterone (DHT) was included in the E. coli (BL21-DE3) fermentation medium at a concentration of 0.05 mM. Induction with 0.4 mM isopropyl-β-D-thiogalactopyranoside was allowed to proceed for 16 hours at 20° C. in M9 minimal media supplemented with casamino acids (Difco) and trace minerals, and pellets were stored at −70° C. A total of 6–9 mg of recombinant AR LBD was isolated from a 15 gram cell pellet following sonication and chromatography on a nickel-chelate resin. Polyhistidine-tagged AR LBD of approximately 90% purity eluted at 0.45 M imidazole in a gradient of 0.05–1.0 imidazole. This material was quantitatively cleaved at an engineered site for thrombin recognition, followed by chromatography on benzamidine sepharose (Pharmacia) to remove the serine protease, with a 70% recovery. The final sample containing the sequence Gly-Ser-His-Met (SEQ ID NO:5) at the N-terminus followed by residues 646–901 of the rat (664–919 in the human) AR LBD protein, was concentrated for crystallography to 2 mg/ml in 20 mM Tris (pH 7.5), 0.5 M NaCl, 10% glycerol, 1 mM EDTA and 1 mM DTT.

The sequence of the rat Androgen Receptor LBD (AR), as cloned, with the secondary structural features marked. For comparison, the aligned sequence of the Progesterone Receptor LBD (PR) is given. Residues involved in androgen binding are marked (*). Residues which are disordered in the crystal structure are underlined. The AR sequence is SEQ ID NO:1. The PR sequence is SEQ ID NO: 2.

purification. In the initial trial to obtain crystallization conditions, a sparse matrix crystallization screen was done with the Crystal Screens 1 and 2 (Hampton Research). For each crystallization trial, a 2 μl drop was prepared by mixing 1 μl of purified protein (1.9 mg ml$^{-1}$) with an equal volume of reservoir solution. The reservoir contained 1.0 ml of the precipitating solution. Small crystals were obtained in two days from six of the drops (table 1).

TABLE 1

Crystallization Conditions

| Screen/# | Precipitating Solution | Result |
|---|---|---|
| 1/16 | 1.5 M Li Sulfate, 0.1 M Na Hepes, pH 7.5 | Small rods |
| 1/29 | 0.8 M Na/K Tartrate, 0.1 M Na Hepes, pH 7.5 | Larger rods |
| 1/30 | 2% v/v PEG 400, 2.0 M Am Sulfate, 0.1 M Na Hepes, pH 7.5 | Small cubes |
| 2/20 | 1.6 M Mg Sulfate, 0.1 M MES, pH 6.5 | Small crystallites |
| 2/32 | 1.6 M Am Sulfate, 0.1 M Na Cl, 0.1 M Hepes, pH 7.5 | Small rods |
| 2/42 | 12% v/v Glycerol, 1.5 M Am Sulfate, 0.1 M Tris, pH 8.5 | Small rods |

The largest single crystal, measuring 0.05 mm×0.04 mm×0.26 mm, was obtained from Crystal Screen 1, solution #29 (0.8 M Na/K Tartrate, 0.1M Na Hepes, pH 7.5). This crystal was subsequently used in the initial data collection run (as described below).

Optimization of the crystallization condition was done using a Cyperlab C-200 automated crystallization robotic workstation. A crystallization trial was performed using a 24-step linear gradient from 0.6 M to 1.26 M Na tartrate, 100 Mm Hepes, pH 7.5 (Note: The optimization screen used sodium rather than sodium/potassium tartrate). The largest, rod shaped crystal, with dimensions 0.09 mm×0.09 mm×0.20 mm, was obtained at 0.887 M Na Tartrate. This crystal was used in the second data collection run (as described below).

```
        |-H1--|                  |----------H3-------------------
    660 GSHMIEGYECQPIFLNVLEAIEPGVVCAGHDNNQPDSFAALLSSLNELGE    AR
    678     GQDIQLIPPLINLLMSIEPDVIYAGHDNTKPDTSSSLLTSLNQLGE    PR
                                                  **

----------|            |----------H4/5----------|
    710 RQLVHVVKWAKALPGFRNLHVDDQMAVIQYSWMGLMVFAMGWRSFTNVNS    AR
    724 RQLLSVVKWSKSLPGFRNLHIDDQITLIQYSWMSLMVFGLGWRSYKHVSG    PR
            *                              *         *

SSSS  SSS |-H6|        |-----H7-----|    |---H8--
    760 RMLYFAPDLVFNEYRMHKSRMYSQCVRMRHLSQEFGWLQITPQEFLCMKA    AR
    774 QMLYFAPDLILNEQRMKESSFYSLCLTMWQIPQEFVKLQVSQEEFLCMKV    PR

-|   SSS           |------H9------|         |-------
    810 LLLFSIIPVDGLKNQKFFDELRMNYIKELDRIIACKRKNPTSCSRRFYQL    AR
    824 LLLLNTIPLEGLRSQTQFEEMRSSYIRELIKAIGLRQKGVVSSSQRFYQL    PR

---H10/11-------------| |--|    |-----H12-----|
    860 TKLLDSVQPIARELHQFTFDLLIKSHMVSVDFPEMMAEIISVQVPKILSG    AR
    874 TKLLDNLHDLVKQLHLYCLNTFIQSRALSVEFPEMMSEVIAAQLPKILAG    PR
                                *

SSS
    910 KVKPIYFHTQ   AR
    924 MVKPLLFHK    PR
```

Crystallization

The AR-LBD—Dihydrotestosterone (DHT) complex was crystallized at 20° C. by vapor diffusion in the hanging-drop mode. In the crystallization trials, the protein complex as obtained from MMB&B was used without any further Data Collection and Reduction For the initial X-ray experiment, the crystal from the initial crystallization screen was flash cooled by dipping it in a cryoprotectant solution containing the precipitating solution (0.8 M Na/K Tartrate, 0.1M Na Hepes, pH 7.5) with 250 mm NaCl and 20% Glycerol added and then placed it in a cold stream at 100° K.

For data set 1, X-ray diffraction data were collected with an R-Axis II imaging plate detector. The radiation was generated from a Rigaku RU-200 rotating at 5 kw power with a fine focus filament (0.3×3.0 mm) was monchromated (Cu Kα) and intensified by focusing with Yale mirrors (Molecular Structure Corporation). The crystal diffracted to better than 2.4 Å resolution. Autoindexing and processing of the measured intensity data was carried out with the HKL software package (Otwinoski, L. (1993) in CCP4 Study Weekend, Data Collection and Processing (Sawyer,L., Issacs, N., and Bailey, S., Eds.) pp 56–62, SERC Daresbury Laboratory, Warrington, U.K). X-ray diffraction from the crystals have the symmetry and systematic absences of the orthorhombic space group P212121 with unit cell dimensions a=56.03 Å, b=66.27 Å, c=70.38 Å, and one molecule per asymmetric unit (Mathews Volume=2.16 Å$^3$ Da$^{-1}$).

A second X-ray diffraction data set (data set 2) was collected at the IMCA-CAT beamline (sector 171D) at the Advanced Photon Source synchrotron at Argonne, Il. The crystal from the optimization screen described above, was flash-cooled by placing it in the reservoir solution (0.877 M Na Tartrate, 0.1M Na Hepes, pH 7.5) with 250 mm NaCl and 20% Glycerol added, and then placing it in a cold stream at 100° K. The data were collected with a Bruker 2×2 mosaic CCD detector. The crystal diffracted to better than 2.0 Å. Autoindexing and processing of the measured intensity data was carried out with the HKL2000 software package (Otwinoski, L. (1993) in CCP4 Study Weekend, Data Collection and Processing (Sawyer, L., Issacs, N., and Bailey, S., Eds.) pp 56–62, SERC Daresbury Laboratory, Warrington, U.K.). The data collection and processing statistics for both data sets are summarized in table 2.

Structure Determination (Molecular Replacement)

The structure was determined by the method of molecular replacement with the program AmoRe (Navaza, J. (1994) AmoRe: an automated package for molecular replacement. Acta Cryst. D50, 157–163). The Progesterone Receptor ligand binding domain (PR-LBD), which has 54% sequence identity and 76% sequence homology to AR-LBD, was used as the search model. The atomic coordinates of PR-LBD (Protein Data Bank reference code 1A28) by Williams & Sigler (Nature 1998 393, 391) were unmodified except for the removal of the ligand and solvent molecules. A second molecular replacement search was performed with a theoretical model for the AR-LBD provided by the MMS/CADD group (table 3). The PR-LBD structure gave a slightly better solution than the AR-model (1.7σvs. 1.3σ above background) and was used in the subsequent refinement, although both structures gave equivalent results with no molecular interpenetration.

TABLE 2

Data Collection and Processing

|  | Data Set I | Data Set II |
|---|---|---|
| Date | May 19, 1999 | Jun. 17, 1999 |
| Source/Detector | Rigaku RU-200 | IMCA/APS 17ID |
| Detector | R-axis II | Bruker 2 × 2 |
| Wavelength | Cu Kα (1.54 Å) | 1.00 Å |
| Frames | 364 | 400 |
| ΔΦ | 0.5° | 0.5° |
| Crystal to plate distance | 150 mm | 135 mm |
| Time/frame | 20 min | 1 sec |
| Number of Observations | 209,891 | 416,207 |
| Data Reduction Program | HKL | HKL2000 |

TABLE 2-continued

Data Collection and Processing

|  | Data Set I | Data Set II |
|---|---|---|
| Unique reflections | 10,824 | 18,308 |
| Reflections Used | 10,114 | 16,862 |
| Resolution | 2.4 Å (2.5–2.4 Å) | 2.0 Å (2.1–2.0 Å) |
| Completeness | 93.8% (71.6%) | 92.6% (73.0%) |
| Multiplicity | 6.3 | 7.3 |
| Mosiacity | 0.502 | 0.332 |
| Rsym (on I) | 4.2% (17.5%) | 10.1% (25.6%) |
| Space Group | P212121 | P212121 |
| a | 56.09 Å | 56.08 Å |
| b | 66.43 Å | 65.76 Å |
| c | 70.54 Å | 70.51 Å |
| Wilson B-value | 39.05 Å$^2$ | 29.26 Å$^2$ |

Values for data in the last resolution shell are given in parentheses

TABLE 3

Molecular Replacement Statistics

| Search Model: | Progesterone (PDB file 1A28) | AR Model |
|---|---|---|
| Program Used | AmoRe | AMoRe |
| Resolution Range | 8.0–4.0 Å | 8.0–4.0 Å |
| Radius of Integration | 25 Å | 25 Å |
| Number of Reflections | 2,393 | 2,393 |
| Number of Atoms | 2,019 | 2,094 |
| RF Correlation (2$^{nd}$ solution) | 0.16 (0.12) | 0.13 (0.11) |
| TF Correlation (2$^{nd}$ solution) | 0.31 (0.20) | 0.23 (0.14) |
| TF R-factor (2$^{nd}$ solution) | 49.0% (52.7%) | 52.1% (54.0%) |
| Rigid Body Correlation | 0.34 | 0.28 |
| Rigid Body R-factor | 48.1% | 50.4% |

Structure Refinement

The structure was first refined with the initial 2.4 Å data set (2σ data, 9,818 reflections) by the method of simulated annealing with program X-PLOR (Brünger, A. T., Kuriyan, J. & Karplus, J. (1987) "Crystallographic R-factor refinement by molecular dynamics", Science 235: 458–460) in four cycles to an R-factor of 27.7%. Each refinement cycle consisted of a least-squares minimization, simulated annealing at 3000°, and individual isotropic B-factor refinement. The first cycle, with the Progesterone molecular replacement model unmodified for the sequence differences between AR and PR, gave an R-factor of 33.8%. The model was then rebuilt using the AR amino acid sequence and a second refinement cycle gave an R-factor of 29.6%. At this stage of the refinement, the DHT molecule could be clearly seen in the difference electron density map.

After each cycle, the structure was carefully examined using molecular computer graphics program Chain (Sack, John S. (1988) "CHAIN—A Crystallographic Modeling Program", J. Mol. Graphics 6: 224–225) and modifications were made to the structure as needed. Several residues, from both the N- and C-termini of the molecule, which were not seen in the electron density maps were removed from the model. After the second cycle of refinement, the DHT was added to the model. Solvent molecules were added where there were 3σ peaks in both the 2Fo-Fc and Fo-Fc electron density maps and removed if their B-factor went above 60 Å$^2$. After four cycles of X-PLOR refinement, a careful examination of the electron density showed the model to be much improved, although molecular refitting still needed to be done in some regions. The density is clear except for some of the loop regions, particularly the loop between helices I and II, which was also poorly modeled in the PR structure.

TABLE 4

Refinement Statistics (X-PLOR)

Part I: 2σ data (9,818 reflections) to 2.4 Å

| Cycle 1 | 251 residues | No ligand | 0 waters | R = 33.8% |
|---|---|---|---|---|
| Cycle 2 | 248 residues | No ligand | 0 waters | R = 29.6% |
| Cycle 3 | 247 residues | ligand | 18 waters | R = 28.3% |
| Cycle 4 | 246 residues | ligand | 40 waters | R = 27.7% |

Part II: 2σ data (15,067 reflections) to 2.0 Å

| Cycle 5 | 246 residues | ligand | 32 waters | R = 27.9% |
|---|---|---|---|---|
| Cycle 6 | 246 residues | ligand | 57 waters | R = 26.8% |
| Cycle 7 | 246 residues | ligand | 58 waters | R = 26.7% |
| Cycle 8 | 246 residues | ligand | 106 waters | R = 24.2% |

At this stage of the refinement, the higher resolution data collected at the APS synchrotron became available. Four additional X-PLOR refinement cycles were performed with the 2.0 Å data set (2σ data, 15,067 reflections) following the same protocol. The final structure has an R-factor of 24.2% with a total of 106 solvent molecules. The final refinement statistics are presented in table 5.

TABLE 5

Final Refinement Parameters

| Resolution Range | 10.0–2.0 Å |
|---|---|
| Reflections | 15,067 |
| R-factor | 24.2% |
| R-free | 31.2% |
| # residues | 246 (672–917) |
| # atoms | 2118 (1991 atoms, 21 DHT, 106 waters) |
| RMS deviations | |
| bond lengths | 0.014 Å |
| bind angles | 1.594° |
| Improper angles | 1.558° |
| Average B-factors | |
| Protein | 25.02 Å$^2$ |
| DHT | 14.40 Å$^2$ |
| Water | 30.21 Å$^2$ |
| Wilson B-factor | 29.26 Å$^2$ |

Description of the Molecule

The structure of AR-LBD is complete from residues 671 through 917 for the wild-type and 672 to 918 for the LNCaP mutant. Analysis of the structures with program PROCHECK showed only minor exceptions to the allowed geometry. In the wild-type structure, the first six residues of the chain (664–670) are not seen in the electron density and are probably disordered. This leaves only one residue before the initial residue of the first α-helix (H1) in the wild-type structure, none in the LNCaP mutant structure. On the C-terminal end, the last two residues (918–919) are not seen in the electron density of the wild-type structure, but only the last is missing in the mutant. In addition, since the loop between helices 9 and 10 (residues 845–850) is not well defined, it has been modeled as poly-alanine.

Folding and Packing

As expected, the AR LBD has the same overall three-dimensional structure as those of the other nuclear hormone receptor LBDs. The molecule is folded into a "helical sandwich" consisting of 10 α-helices. There are four small pieces of beta strand, forming two short beta-sheets; one in the core of the molecule between helices 5 and 6 near the ligand binding site, and the other formed by the loop between helices 8 and 9 and the C-terminus. This latter sheet, also seen in the PR LBD structure, holds helix 12 in the closed, agonist conformation, close to and capping the ligand binding site.

Lack of Dimer Formation

Studies have indicated that the estrogen, progesterone, and androgen receptors all function as homodimers and that AR LBD forms dimers in solution. Thus it could be expected that the AR LBD domains might form homodimers in the crystal similar to those previously seen in the RXR-Δ and estrogen receptor (ER) LBD crystal structures. In the PR LBD structure, the two monomers in the asymmetric unit are related by a dyad, but the two-fold-symmetric configuration is strikingly different from that of the RXR and ER homodimers and the area buried in this configuration is much smaller than would be expected for stable dimer formation. In the AR LBD crystal, the ligand-binding domains are unmistakably monomeric, and there are no twofold axes relating domains. Moreover, the homodimer interaction seen in the structures of ER and RXR LBDs is not possible for the AR LBD, as the C-terminal tail is bound to the groove formed by helices 9 and 10, thereby obstructing the contact region between monomers in RXR and ER homodimers. Whether this observation reflects a non-dimeric state of the AR LBD in the functional AR dimer or is an artifact of the conditions used for AR LBD crystallization remains to be determined. It is noteworthy that the ER LBD constructs used for crystallization have been truncated to remove an analogous C-terminal extension.

Comparison with Progesterone Receptor

While there is only 55% sequence identity between AR LBD and PR LBD, there is a 77% sequence similarity, and as expected, the three-dimensional structures of these two LBDs are very similar with an r.m.s. deviation of 1.3 Å between corresponding Cα atom positions. As with PR, AR LBD has no helix 2, but its helix 12 is longer than those of RXR or TR. In the case of AR, while helices 10 and 11 are nearly contiguous, there is a proline residue at position 868 that causes a kink between the two helices.

Comparison with Theoretical AR Model

The theoretical AR model obtained from MMS/CADD and the AR structure have an r.m.s. deviation of 1.29 Å for the 247 alpha carbons. More importantly, the hormone binding site is virtually identical with the exception of the side chains of Met 732(749), Leu 863(880), and Leu 864 (881) which are in different rotomers. This causes the binding cavity to be more compact in the AR structure. Also, there is a flip of the side chain of Asn 688(705) so that the ND2 atom is in position to make a hydrogen bond to the carbonyl off of the D-ring.

TABLE 6

Comparison of AR-LBD to PR-LBD and Theoretical model

| | Calpha | Main | Side | Total |
|---|---|---|---|---|
| AR vs. Pr | 1.22 (246) | 1.27 (983) | 1.80 (772) | 1.53 (1,755) |
| AR vs. CADD | 1.25 (246) | 1.31 (983) | 2.41 (971) | 1.93 (1,954) |

Binding of Dihydrotestosterone

At the end of the molecular replacement procedure with the PR LBD structure without progesterone as search model, the largest piece of difference electron density, at approximately the 3σ level, was found at the progesterone-binding site. Replacing the bound progesterone agonist (which has a carboxyl group at the 17-position) with a model of d-hydrotestosterone (DHT, which has a hydroxyl group at the 17-position) produced an even better fit to the difference electron density, indicating that DHT binds to AR LBD in an almost identical fashion to the way progesterone binds to PR LBD. Both agonists interact with helices 3, 5, and 11 of their respective LBDs. Ring A, which is identical in the two steroids, makes similar interactions with the side chains of Q711, M745, R752 (Q725, M759, R766 in PR LBD), and a conserved water molecule. The interactions with ring C are also similar, with close contacts to the mainchain of L704 (L718 in PR LBD) and sidechain of N705 (N719 in PR LBD). The contact between C18 and the Oγ1 of T877 is unique to the wild-type AR LBD, as the corresponding cysteinyl side chain is pointed away from the steroid in the PR LBD structure.

Since progesterone and DHT differ in the substituent on ring D, it is expected that interactions with respective receptors will differ in this region. In the AR LBD structure, Nδ2 of N705 makes a hydrogen bond to the D-ring hydroxyl of DHT. A similar interaction could be made between progesterone and the PR LBD if there were a flip of both the steroid acetyl group and the side chain of N719. This would place the oxygen approximately 3.2 Å from the Nδ2 atom of Asn 719. The ligand contact surface area is slightly larger for progesterone in PR than for DHT in AR (483 vs. 448 Å$^2$) but they are both considerably smaller than the ligand contact surface area in TR (559 Å$^2$), PPARγ (583 Å$^2$), or the Vitamin D receptor (677 Å$^2$).

Figure 3:
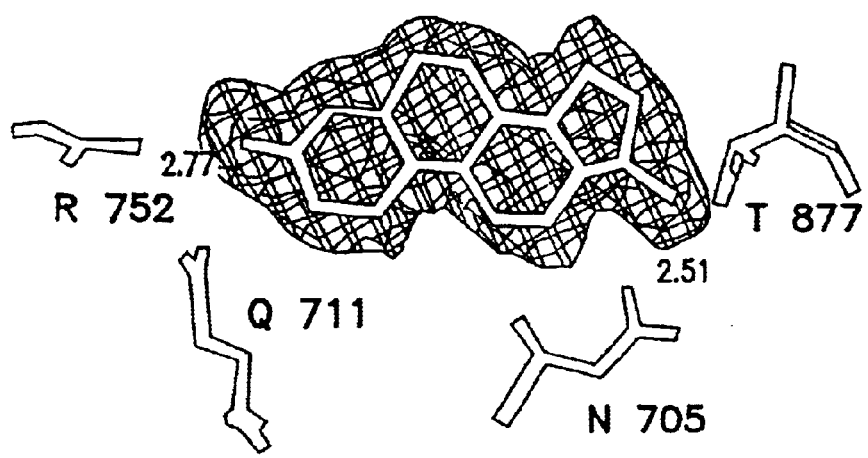
FIG. 3 provides three views of the omit electron density map of dihydrotestosterone (DHT) in the hormone-binding site of AR-LBD. There are hydrogen bonds between the steroid and the side chains of Arg 752 and Asn 705.
Figure 3:
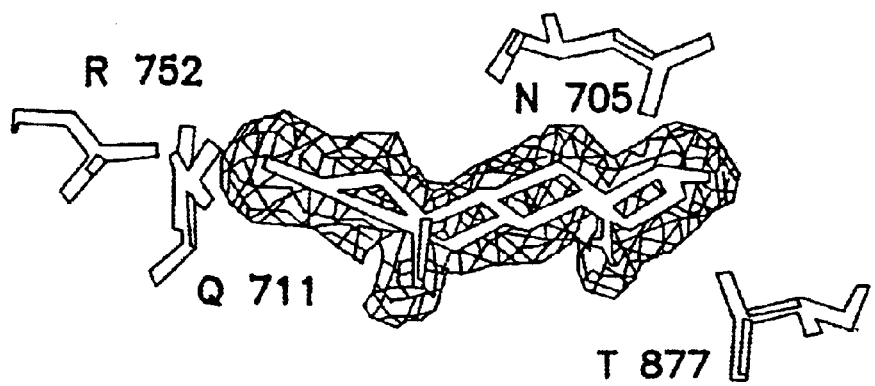
Figure 3:
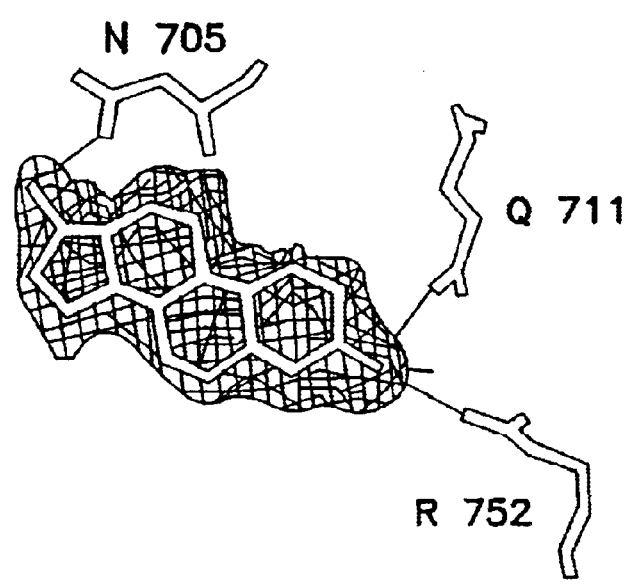

FIG. 3 shows two orthogonal views of the omit electron density map of dihydrotestosterone (DHT) in the hormone-binding site of AR-LBD. There are hydrogen bonds between the steroid and the side chains of Arg 752 and Asn 705.

TABLE 7

| Dihydrotestosterone Contacts (3.4 Å) | | |
|---|---|---|
| Hydrogen Bonds | | |
| O3 | Arg 752 Nh2 | 2.89 Å (2.77 Å) |
| O3 | Gln 711 Nε2 | 3.36 Å (3.20 Å) |
| O20 | Asn 705 Nδ2 | 2.80 Å (3.20 Å) |
| O20 | Thr 877 Oγ1 | 2.70 Å (N/A) |
| Possible Close Contacts | | |
| C11 | Leu 704 O | 3.31 Å |

TABLE 7-continued

| Dihydrotestosterone Contacts (3.4 Å) | | |
|---|---|---|
| C12 | Asn 705 Nδ2 | 3.07 Å |
| C17 | Asn 705 Nδ2 | 3.34 Å |
| C19 | Met 745 Sδ | 3.38 Å |
| C18 | Thr 877 Oγ1 | 3.07 Å |

Comparison with Progesterone binding

Comparison of the structure of DHT in the AR-LBD with the structure of progesterone in the PR-LBD (Williams, S. P. & Sigler, P. B. (1998) "Atomic Structure of Progesterone Complexed with its Receptor", Nature 393, 391) shows a similar mode of binding. Ring A, which is identical in the two steroids, makes similar interactions with the side chains of Q711, M745, R752, Q711 and a conserved water molecule (table 8). The interaction with ring C are also similar, with close contacts to the mainchain of L704 and sidechain of N705. The contact from C18 to the Oγ1 of T877 is unique to AR-LBD, as the corresponding cysteine sidechain is pointed away from the steroid in the PR-LBD structure Since progesterone and DHT differ in the substitution off of ring D, it is expected that there will be different interactions with the protein in this region. In the AR structure, the Nδ2 atom of Asn 705 makes hydrogen bond to the D-ring hydroxyl.

A similar interaction could be made in the PR if there were a flip of both the steroid carboxyl group and the side chain of N719. This would place the carboxyl oxygen approximately 3.2 A from the Nδ2 atom of Asn 719. In AR-LBD, there is also a close contact to the side chain of T877 which is absent in the PR-LBD structure.

Figure 4:
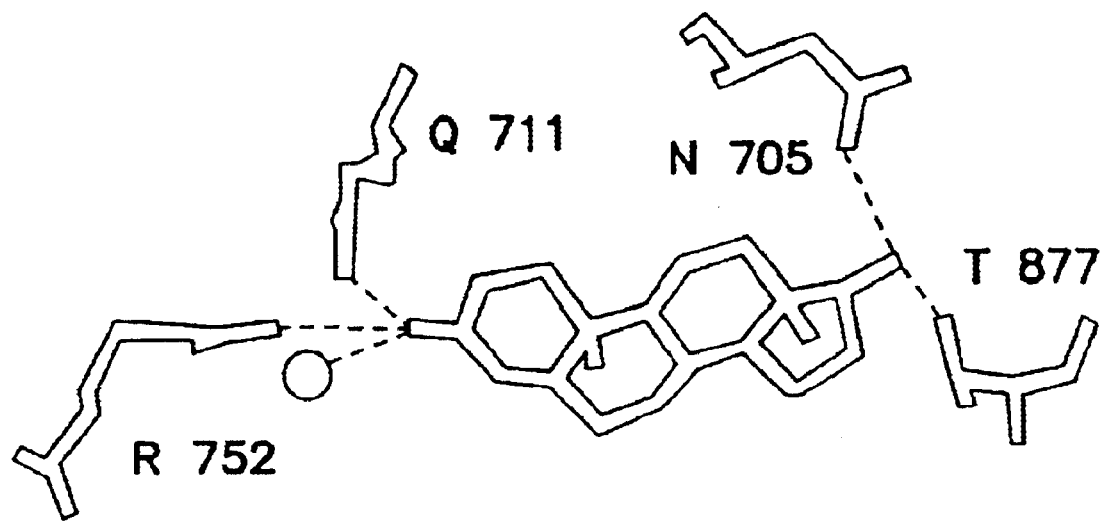
FIG. 4 is a comparison of the binding of dihydrotestosterone to AR-LBD (top) and of progesterone to PR-LBD (bottom). Note that an additional hydrogen bond interaction would be possible if both the sidechains of both N719 and the progesterone were flipped.
Figure 4:
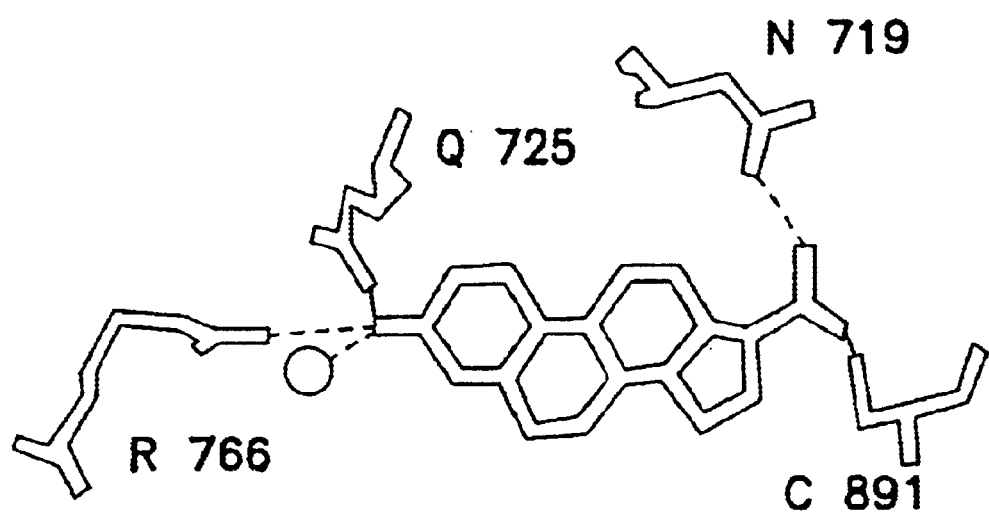

FIG. 4 shows comparison of AR and PR steroid binding Comparison of the binding of dihydrotestosterone to AR-LBD (top) and of progesterone to PR-LBD (bottom). Note that an additional hydrogen bond interaction would be possible if both the sidechains of both N719 and the progesterone were flipped.

TABLE 8

| Comparison of AR and PR steroid binding | | |
|---|---|---|
| | AR | PR |
| Ring A | | |
| O3: | H-bond to R752 NH2 (2.9 Å) | H-bond to R766 NH2 (2.8 Å) |
| | H-bond to water (3.5 Å) | H-bond to water (3.1/3.4 Å) |
| | SC of Q711 in different rotomer distance to O3 is 3.4 and 4.13 Å | Contact to SC of Gln 725 distance to O3 is 3.2 and 3.3 Å |
| C19 | Contact to M745 SD (3.4 Å) | Similar orientation (3.5 Å) |
| C2: | SC of Q711 (3.5 Å) | different rotomer (3.2 & 3.3) distance to C4 is 4.1 Å |
| Ring C | | |
| C11 | LO704 O (3.3 Å) | (3.5 Å) |
| C12 | Contact to N705 Nδ2 (3.1 Å) | Contact to N719 Oδ1 (3.4 Å) |
| C18 | Contact T877 Oγ1 (3.1 Å) | SC of C891 pointing away distance to Sγ is 3.8 Å |
| Ring D | | |
| O20/C21 | O21 in AR is close to C21 in PR (Possible flip of Carboxyl in PR?) | |
| | N/A | O20: Contact to C891 Cα (3.2 Å) |
| | O20: H-bond N705 Nδ2 (2.8 Å) | C21: Contact to N719 OD1 (3.2 Å) |
| | O20: Contact T877 Cγ1 (2.7 Å) | SC of C891 pointing away |
| C17 | Contact N705 Nδ2 (3.3 Å) | Ring in slightly different orientation; distance to N719 Oδ1 is 4.7 Å |

Structure of the Complex of DHT with the LBD of the LNCAP Mutant

In the LNCaP mutant, T877 is replaced by an alanine residue. The mutant LBD structure has an r.m.s. deviation of 0.8 Å compared to the wild-type structure, close to the expected r.m.s. deviation due to the estimated errors in the coordinates. In particular, the binding of DHT is essentially identical by wild-type and mutant LBDs except at the point of mutation. Here the replacement of T877 by alanine leaves additional space off the D-ring of DHT to accommodate a larger substituent on position 17. This may explain the promiscuous ability of the LNCaP mutant, unlike wild-type AR, to bind to a variety of other hormones and analogs like some progestins, estrogens and cortisols that differ from DHT in substitution at position 17. For example, the binding of flutamide, estradiol, and progesterone to the LNCaP mutant can activate the mutant receptor. Conversely, mutation of T877 to residues with larger sidechains such as aspartic acid and lysine would be expected completely preclude the binding of ligands with any substituent at position 17 of the D-ring and such mutations have been shown to totally eliminate androgen binding.

TABLE A

| | | | | | | | | |
|---|---|---|---|---|---|---|---|---|
| ATOM | 1 | CB | ILE | 672 | 14.846 | 25.527 | 23.734 | 1.00 | 25.78 |
| ATOM | 2 | CG2 | ILE | 672 | 16.247 | 25.008 | 24.099 | 1.00 | 25.56 |
| ATOM | 3 | CG1 | ILE | 672 | 14.842 | 27.035 | 23.978 | 1.00 | 25.60 |
| ATOM | 4 | CD1 | ILE | 672 | 15.312 | 27.404 | 25.360 | 1.00 | 25.81 |
| ATOM | 5 | C | ILE | 672 | 15.115 | 23.900 | 21.789 | 1.00 | 25.32 |
| ATOM | 6 | O | ILE | 672 | 16.189 | 23.926 | 21.195 | 1.00 | 24.67 |
| ATOM | 7 | N | ILE | 672 | 13.004 | 25.282 | 22.008 | 1.00 | 24.75 |
| ATOM | 8 | CA | ILE | 672 | 14.475 | 25.215 | 22.242 | 1.00 | 25.11 |
| ATOM | 9 | N | PHE | 673 | 14.448 | 22.768 | 22.030 | 1.00 | 25.89 |
| ATOM | 10 | CA | PHE | 673 | 14.980 | 21.446 | 21.635 | 1.00 | 25.86 |
| ATOM | 11 | CB | PHE | 673 | 14.020 | 20.306 | 22.029 | 1.00 | 26.22 |
| ATOM | 12 | CG | PHE | 673 | 14.557 | 18.923 | 21.722 | 1.00 | 25.12 |
| ATOM | 13 | CD1 | PHE | 673 | 15.765 | 18.501 | 22.251 | 1.00 | 25.16 |
| ATOM | 14 | CD2 | PHE | 673 | 13.877 | 18.066 | 20.874 | 1.00 | 25.81 |
| ATOM | 15 | CE1 | PHE | 673 | 16.286 | 17.255 | 21.946 | 1.00 | 23.42 |
| ATOM | 16 | CE2 | PHE | 673 | 14.403 | 16.809 | 20.567 | 1.00 | 25.08 |
| ATOM | 17 | CZ | PHE | 673 | 15.609 | 16.417 | 21.107 | 1.00 | 23.85 |
| ATOM | 18 | C | PHE | 673 | 15.213 | 21.374 | 20.147 | 1.00 | 25.25 |
| ATOM | 19 | O | PHE | 673 | 16.260 | 20.926 | 19.680 | 1.00 | 24.38 |
| ATOM | 20 | N | LEU | 674 | 14.193 | 21.792 | 19.412 | 1.00 | 25.01 |
| ATOM | 21 | CA | LEU | 674 | 14.237 | 21.802 | 17.969 | 1.00 | 25.58 |
| ATOM | 22 | CB | LEU | 674 | 12.833 | 21.974 | 17.391 | 1.00 | 26.05 |
| ATOM | 23 | CG | LEU | 674 | 12.067 | 20.653 | 17.317 | 1.00 | 26.55 |
| ATOM | 24 | CD1 | LEU | 674 | 10.617 | 20.887 | 16.935 | 1.00 | 26.35 |
| ATOM | 25 | CD2 | LEU | 674 | 12.762 | 19.758 | 16.304 | 1.00 | 26.09 |
| ATOM | 26 | C | LEU | 674 | 15.199 | 22.801 | 17.357 | 1.00 | 25.10 |
| ATOM | 27 | O | LEU | 674 | 15.743 | 22.518 | 16.294 | 1.00 | 26.08 |
| ATOM | 28 | N | ASN | 675 | 15.440 | 23.939 | 18.019 | 1.00 | 24.63 |
| ATOM | 29 | CA | ASN | 675 | 16.356 | 24.964 | 17.484 | 1.00 | 23.19 |
| ATOM | 30 | CB | ASN | 675 | 16.478 | 26.215 | 18.393 | 1.00 | 24.20 |
| ATOM | 31 | CG | ASN | 675 | 15.206 | 27.067 | 18.452 | 1.00 | 24.32 |
| ATOM | 32 | OD1 | ASN | 675 | 14.368 | 27.062 | 17.547 | 1.00 | 24.82 |
| ATOM | 33 | ND2 | ASN | 675 | 15.076 | 27.817 | 19.539 | 1.00 | 24.74 |
| ATOM | 34 | C | ASN | 675 | 17.726 | 24.338 | 17.397 | 1.00 | 21.66 |
| ATOM | 35 | O | ASN | 675 | 18.435 | 24.524 | 16.417 | 1.00 | 21.43 |
| ATOM | 36 | N | VAL | 676 | 18.095 | 23.612 | 18.448 | 1.00 | 21.17 |
| ATOM | 37 | CA | VAL | 676 | 19.394 | 22.952 | 18.507 | 1.00 | 20.92 |
| ATOM | 38 | CB | VAL | 676 | 19.718 | 22.442 | 19.934 | 1.00 | 21.33 |
| ATOM | 39 | CG1 | VAL | 676 | 18.899 | 21.237 | 20.247 | 1.00 | 24.09 |
| ATOM | 40 | CG2 | VAL | 676 | 21.192 | 22.095 | 20.065 | 1.00 | 21.88 |
| ATOM | 41 | C | VAL | 676 | 19.501 | 21.830 | 17.473 | 1.00 | 19.78 |
| ATOM | 42 | O | VAL | 676 | 20.421 | 21.827 | 16.646 | 1.00 | 19.99 |
| ATOM | 43 | N | LEU | 677 | 18.530 | 20.923 | 17.434 | 1.00 | 19.08 |
| ATOM | 44 | CA | LEU | 677 | 18.601 | 19.848 | 16.453 | 1.00 | 17.91 |
| ATOM | 45 | CB | LEU | 677 | 17.383 | 18.921 | 16.518 | 1.00 | 17.50 |
| ATOM | 46 | CG | LEU | 677 | 17.267 | 18.083 | 17.798 | 1.00 | 16.78 |
| ATOM | 47 | CD1 | LEU | 677 | 16.355 | 16.934 | 17.541 | 1.00 | 17.01 |
| ATOM | 48 | CD2 | LEU | 677 | 18.615 | 17.555 | 18.225 | 1.00 | 17.10 |
| ATOM | 49 | C | LEU | 677 | 18.768 | 20.427 | 15.068 | 1.00 | 16.96 |
| ATOM | 50 | O | LEU | 677 | 19.640 | 20.008 | 14.347 | 1.00 | 14.94 |
| ATOM | 51 | N | GLU | 678 | 17.980 | 21.445 | 14.736 | 1.00 | 19.12 |
| ATOM | 52 | CA | GLU | 678 | 18.058 | 22.121 | 13.437 | 1.00 | 20.06 |
| ATOM | 53 | CB | GLU | 678 | 16.972 | 23.188 | 13.317 | 1.00 | 23.33 |
| ATOM | 54 | CG | GLU | 678 | 15.532 | 22.646 | 13.381 | 1.00 | 28.64 |
| ATOM | 55 | CD | GLU | 678 | 14.459 | 23.736 | 13.387 | 1.00 | 32.31 |
| ATOM | 56 | OE1 | GLU | 678 | 14.811 | 24.943 | 13.374 | 1.00 | 34.41 |
| ATOM | 57 | OE2 | GLU | 678 | 13.253 | 23.384 | 13.410 | 1.00 | 34.91 |
| ATOM | 58 | C | GLU | 678 | 19.410 | 22.783 | 13.243 | 1.00 | 19.33 |
| ATOM | 59 | O | GLU | 678 | 19.966 | 22.737 | 12.152 | 1.00 | 18.20 |
| ATOM | 60 | N | ALA | 679 | 19.966 | 23.324 | 14.329 | 1.00 | 19.45 |
| ATOM | 61 | CA | ALA | 679 | 21.257 | 24.018 | 14.303 | 1.00 | 18.84 |
| ATOM | 62 | CB | ALA | 679 | 21.388 | 24.919 | 15.517 | 1.00 | 17.67 |
| ATOM | 63 | C | ALA | 679 | 22.472 | 23.094 | 14.195 | 1.00 | 19.25 |
| ATOM | 64 | O | ALA | 679 | 23.479 | 23.436 | 13.558 | 1.00 | 19.27 |

TABLE A-continued

| | | | | | | | | |
|---|---|---|---|---|---|---|---|---|
| ATOM | 65 | N | ILE | 680 | 22.395 | 21.914 | 14.802 | 1.00 | 18.82 |
| ATOM | 66 | CA | ILE | 680 | 23.518 | 20.984 | 14.742 | 1.00 | 17.49 |
| ATOM | 67 | CB | ILE | 680 | 23.674 | 20.231 | 16.056 | 1.00 | 17.05 |
| ATOM | 68 | CG2 | ILE | 680 | 24.022 | 21.213 | 17.158 | 1.00 | 16.83 |
| ATOM | 69 | CG1 | ILE | 680 | 22.393 | 19.467 | 16.391 | 1.00 | 15.55 |
| ATOM | 70 | CD1 | ILE | 680 | 22.558 | 18.575 | 17.552 | 1.00 | 13.80 |
| ATOM | 71 | C | ILE | 680 | 23.516 | 19.984 | 13.593 | 1.00 | 16.89 |
| ATOM | 72 | O | ILE | 680 | 24.518 | 19.303 | 13.370 | 1.00 | 17.12 |
| ATOM | 73 | N | GLU | 681 | 22.415 | 19.922 | 12.847 | 1.00 | 16.79 |
| ATOM | 74 | CA | GLU | 681 | 22.265 | 19.002 | 11.719 | 1.00 | 17.26 |
| ATOM | 75 | CB | GLU | 681 | 20.902 | 19.227 | 11.094 | 1.00 | 16.72 |
| ATOM | 76 | CG | GLU | 681 | 20.579 | 18.300 | 9.952 | 1.00 | 18.48 |
| ATOM | 77 | CD | GLU | 681 | 20.473 | 16.823 | 10.348 | 1.00 | 17.51 |
| ATOM | 78 | OE1 | GLU | 681 | 20.659 | 16.502 | 11.524 | 1.00 | 17.58 |
| ATOM | 79 | OE2 | GLU | 681 | 20.214 | 15.981 | 9.467 | 1.00 | 18.59 |
| ATOM | 80 | C | GLU | 681 | 23.370 | 19.128 | 10.673 | 1.00 | 18.79 |
| ATOM | 81 | O | GLU | 681 | 23.517 | 20.173 | 10.043 | 1.00 | 20.09 |
| ATOM | 82 | N | PRO | 682 | 24.145 | 18.044 | 10.437 | 1.00 | 19.02 |
| ATOM | 83 | CD | PRO | 682 | 23.969 | 16.704 | 11.019 | 1.00 | 18.22 |
| ATOM | 84 | CA | PRO | 682 | 25.252 | 18.021 | 9.472 | 1.00 | 19.11 |
| ATOM | 85 | CB | PRO | 682 | 25.681 | 16.546 | 9.493 | 1.00 | 18.30 |
| ATOM | 86 | CG | PRO | 682 | 25.338 | 16.109 | 10.846 | 1.00 | 17.08 |
| ATOM | 87 | C | PRO | 682 | 24.912 | 18.475 | 8.057 | 1.00 | 19.76 |
| ATOM | 88 | O | PRO | 682 | 23.771 | 18.382 | 7.625 | 1.00 | 21.13 |
| ATOM | 89 | N | GLY | 683 | 25.901 | 18.995 | 7.339 | 1.00 | 20.64 |
| ATOM | 90 | CA | GLY | 683 | 25.665 | 19.422 | 5.972 | 1.00 | 21.67 |
| ATOM | 91 | C | GLY | 683 | 25.809 | 18.260 | 4.990 | 1.00 | 23.13 |
| ATOM | 92 | O | GLY | 683 | 25.595 | 17.108 | 5.355 | 1.00 | 23.47 |
| ATOM | 93 | N | VAL | 684 | 26.190 | 18.567 | 3.748 | 1.00 | 23.58 |
| ATOM | 94 | CA | VAL | 684 | 26.365 | 17.573 | 2.685 | 1.00 | 22.44 |
| ATOM | 95 | CB | VAL | 684 | 26.320 | 18.216 | 1.259 | 1.00 | 24.93 |
| ATOM | 96 | CG1 | VAL | 684 | 26.217 | 17.130 | 0.183 | 1.00 | 24.57 |
| ATOM | 97 | CG2 | VAL | 684 | 25.153 | 19.228 | 1.131 | 1.00 | 24.89 |
| ATOM | 98 | C | VAL | 684 | 27.725 | 16.934 | 2.811 | 1.00 | 20.64 |
| ATOM | 99 | O | VAL | 684 | 28.708 | 17.614 | 3.042 | 1.00 | 19.82 |
| ATOM | 100 | N | VAL | 685 | 27.778 | 15.631 | 2.585 | 1.00 | 19.05 |
| ATOM | 101 | CA | VAL | 685 | 29.012 | 14.878 | 2.665 | 1.00 | 17.89 |
| ATOM | 102 | CB | VAL | 685 | 28.955 | 13.857 | 3.867 | 1.00 | 17.81 |
| ATOM | 103 | CG1 | VAL | 685 | 30.303 | 13.189 | 4.086 | 1.00 | 15.58 |
| ATOM | 104 | CG2 | VAL | 685 | 28.527 | 14.556 | 5.147 | 1.00 | 16.27 |
| ATOM | 105 | C | VAL | 685 | 29.143 | 14.112 | 1.345 | 1.00 | 17.88 |
| ATOM | 106 | O | VAL | 685 | 28.238 | 13.367 | 0.969 | 1.00 | 18.33 |
| ATOM | 107 | N | CYS | 686 | 30.224 | 14.339 | 0.609 | 1.00 | 17.00 |
| ATOM | 108 | CA | CYS | 686 | 30.451 | 13.628 | -0.650 | 1.00 | 17.52 |
| ATOM | 109 | CB | CYS | 686 | 31.101 | 14.534 | -1.706 | 1.00 | 17.76 |
| ATOM | 110 | SG | CYS | 686 | 30.166 | 16.031 | -2.147 | 1.00 | 21.38 |
| ATOM | 111 | C | CYS | 686 | 31.354 | 12.447 | -0.327 | 1.00 | 16.97 |
| ATOM | 112 | O | CYS | 686 | 32.141 | 12.496 | 0.615 | 1.00 | 17.15 |
| ATOM | 113 | N | ALA | 687 | 31.183 | 11.360 | -1.065 | 1.00 | 17.74 |
| ATOM | 114 | CA | ALA | 687 | 31.949 | 10.132 | -0.836 | 1.00 | 17.57 |
| ATOM | 115 | CB | ALA | 687 | 31.161 | 8.929 | -1.295 | 1.00 | 16.91 |
| ATOM | 116 | C | ALA | 687 | 33.277 | 10.161 | -1.526 | 1.00 | 18.06 |
| ATOM | 117 | O | ALA | 687 | 34.185 | 9.431 | -1.139 | 1.00 | 17.98 |
| ATOM | 118 | N | GLY | 688 | 33.370 | 11.023 | -2.539 | 1.00 | 18.50 |
| ATOM | 119 | CA | GLY | 688 | 34.580 | 11.167 | -3.326 | 1.00 | 19.16 |
| ATOM | 120 | C | GLY | 688 | 34.705 | 10.099 | -4.388 | 1.00 | 19.90 |
| ATOM | 121 | O | GLY | 688 | 35.802 | 9.730 | -4.771 | 1.00 | 20.86 |
| ATOM | 122 | N | HIS | 689 | 33.582 | 9.630 | -4.907 | 1.00 | 20.92 |
| ATOM | 123 | CA | HIS | 689 | 33.577 | 8.576 | -5.912 | 1.00 | 22.43 |
| ATOM | 124 | CB | HIS | 689 | 32.195 | 7.917 | -5.900 | 1.00 | 22.00 |
| ATOM | 125 | CG | HIS | 669 | 32.046 | 6.775 | -6.857 | 1.00 | 22.28 |
| ATOM | 126 | CD2 | HIS | 689 | 32.782 | 5.656 | -7.033 | 1.00 | 22.64 |
| ATOM | 127 | ND1 | HIS | 669 | 31.040 | 6.724 | -7.796 | 1.00 | 22.44 |
| ATOM | 128 | CE1 | HIS | 689 | 31.166 | 5.627 | -8.516 | 1.00 | 23.43 |
| ATOM | 129 | NE2 | HIS | 689 | 32.219 | 4.960 | -8.074 | 1.00 | 23.78 |
| ATOM | 130 | C | HIS | 689 | 33.923 | 9.063 | -7.328 | 1.00 | 24.19 |
| ATOM | 131 | O | HIS | 689 | 33.511 | 10.145 | -7.731 | 1.00 | 24.06 |
| ATOM | 132 | N | ASP | 690 | 34.719 | 8.296 | -8.073 | 1.00 | 26.27 |
| ATOM | 133 | CA | ASP | 690 | 35.017 | 8.691 | -9.447 | 1.00 | 28.86 |
| ATOM | 134 | CB | ASP | 690 | 36.330 | 8.096 | -9.963 | 1.00 | 28.93 |
| ATOM | 135 | CG | ASF | 690 | 36.696 | 8.618 | -11.361 | 1.00 | 30.03 |
| ATOM | 136 | OD1 | ASP | 690 | 37.868 | 8.497 | -11.764 | 1.00 | 31.23 |
| ATOM | 137 | OD2 | ASP | 690 | 35.819 | 9.170 | -12.061 | 1.00 | 29.72 |
| ATOM | 138 | C | ASP | 690 | 33.872 | 8.164 | -10.286 | 1.00 | 30.15 |
| ATOM | 139 | O | ASP | 690 | 33.701 | 6.952 | -10.409 | 1.00 | 30.46 |
| ATOM | 140 | N | ASN | 691 | 33.065 | 9.067 | -10.832 | 1.00 | 32.35 |
| ATOM | 141 | CA | ASN | 691 | 31.933 | 8.660 | -11.655 | 1.00 | 33.60 |
| ATOM | 142 | CB | ASN | 691 | 30.725 | 9.562 | -11.416 | 1.00 | 32.74 |
| ATOM | 143 | CG | ASN | 691 | 30.079 | 9.313 | -10.074 | 1.00 | 32.95 |

TABLE A-continued

| ATOM | 144 | OD1 | ASN | 691 | 29.187 | 8.474 | −9.930 | 1.00 | 32.13 |
|------|-----|-----|-----|-----|--------|-------|--------|------|-------|
| ATOM | 145 | ND2 | ASN | 691 | 30.547 | 10.024 | −9.069 | 1.00 | 33.57 |
| ATOM | 146 | C | ASN | 691 | 32.284 | 8.608 | −13.136 | 1.00 | 35.13 |
| ATOM | 147 | O | ASN | 691 | 31.419 | 8.733 | −13.999 | 1.00 | 36.66 |
| ATOM | 148 | N | ALA | 692 | 33.565 | 8.471 | −13.434 | 1.00 | 36.15 |
| ATOM | 149 | CA | ALA | 692 | 33.995 | 8.365 | −14.819 | 1.00 | 37.44 |
| ATOM | 150 | CB | ALA | 692 | 35.148 | 9.328 | −15.103 | 1.00 | 36.71 |
| ATOM | 151 | C | ALA | 692 | 34.425 | 6.913 | −15.027 | 1.00 | 38.39 |
| ATOM | 152 | O | ALA | 692 | 34.414 | 6.406 | −16.139 | 1.00 | 39.10 |
| ATOM | 153 | N | GLN | 693 | 34.757 | 6.241 | −13.928 | 1.00 | 39.29 |
| ATOM | 154 | CA | GLN | 693 | 35.200 | 4.849 | −13.942 | 1.00 | 40.00 |
| ATOM | 155 | CB | GLN | 693 | 36.131 | 4.577 | −12.745 | 1.00 | 41.81 |
| ATOM | 156 | CG | GLN | 693 | 37.538 | 4.029 | −13.110 | 1.00 | 44.34 |
| ATOM | 157 | CD | GLN | 693 | 38.420 | 5.017 | −13.902 | 1.00 | 45.44 |
| ATOM | 158 | OE1 | GLN | 693 | 39.378 | 5.587 | −13.363 | 1.00 | 45.95 |
| ATOM | 159 | NE2 | GLN | 693 | 38.115 | 5.193 | −15.186 | 1.00 | 45.47 |
| ATOM | 160 | C | GLN | 693 | 33.988 | 3.939 | −13.854 | 1.00 | 39.48 |
| ATOM | 161 | O | GLN | 693 | 32.997 | 4.298 | −13.217 | 1.00 | 40.11 |
| ATOM | 162 | N | PRO | 694 | 34.055 | 2.743 | −14.485 | 1.00 | 38.78 |
| ATOM | 163 | CD | PRO | 694 | 35.138 | 2.286 | −15.375 | 1.00 | 38.88 |
| ATOM | 164 | CA | PRO | 694 | 32.970 | 1.762 | −14.489 | 1.00 | 36.98 |
| ATOM | 165 | CB | PRO | 694 | 33.571 | 0.601 | −15.265 | 1.00 | 37.17 |
| ATOM | 166 | CG | PRO | 694 | 34.432 | 1.271 | −16.234 | 1.00 | 38.48 |
| ATOM | 167 | C | PRO | 694 | 32.575 | 1.304 | −13.109 | 1.00 | 35.56 |
| ATOM | 168 | O | PRO | 694 | 33.411 | 1.198 | −12.204 | 1.00 | 35.44 |
| ATOM | 169 | N | ASP | 695 | 31.289 | 1.022 | −12.958 | 1.00 | 34.27 |
| ATOM | 170 | CA | ASP | 695 | 30.776 | 0.534 | −11.698 | 1.00 | 32.38 |
| ATOM | 171 | CB | ASP | 695 | 29.251 | 0.518 | −11.694 | 1.00 | 29.77 |
| ATOM | 172 | CG | ASP | 695 | 28.660 | 1.901 | −11.608 | 1.00 | 28.80 |
| ATOM | 173 | OD1 | ASP | 695 | 27.532 | 2.100 | −12.089 | 1.00 | 27.09 |
| ATOM | 174 | OD2 | ASP | 695 | 29.329 | 2.794 | −11.057 | 1.00 | 28.72 |
| ATOM | 175 | C | ASP | 695 | 31.318 | −0.868 | −11.524 | 1.00 | 32.55 |
| ATOM | 176 | O | ASP | 695 | 31.237 | −1.707 | −12.429 | 1.00 | 33.50 |
| ATOM | 177 | N | SER | 696 | 32.025 | −1.052 | −10.424 | 1.00 | 31.71 |
| ATOM | 178 | CA | SER | 696 | 32.577 | −2.333 | −10.077 | 1.00 | 30.42 |
| ATOM | 179 | CB | SER | 696 | 34.064 | −2.383 | −10.425 | 1.00 | 30.43 |
| ATOM | 180 | OG | SER | 696 | 34.854 | −1.589 | −9.567 | 1.00 | 31.47 |
| ATOM | 181 | C | SER | 696 | 32.340 | −2.445 | −8.577 | 1.00 | 30.15 |
| ATOM | 182 | O | SER | 696 | 32.275 | −1.418 | −7.885 | 1.00 | 30.10 |
| ATOM | 183 | N | PHE | 697 | 32.104 | −3.669 | −8.099 | 1.00 | 28.48 |
| ATOM | 184 | CA | PHE | 697 | 31.890 | −3.933 | −6.679 | 1.00 | 26.74 |
| ATOM | 185 | CB | PHE | 697 | 31.982 | −5.442 | −6.423 | 1.00 | 25.46 |
| ATOM | 186 | CG | PHE | 697 | 31.781 | −5.827 | −4.989 | 1.00 | 24.31 |
| ATOM | 187 | CD1 | PHE | 697 | 30.536 | −5.722 | −4.398 | 1.00 | 24.48 |
| ATOM | 188 | CD2 | PHE | 697 | 32.845 | −6.281 | −4.220 | 1.00 | 24.78 |
| ATOM | 189 | CE1 | PHE | 697 | 30.344 | −6.063 | −3.071 | 1.00 | 24.65 |
| ATOM | 190 | CE2 | PHE | 697 | 32.659 | −6.626 | −2.886 | 1.00 | 24.77 |
| ATOM | 191 | CZ | PHE | 697 | 31.406 | −6.512 | −2.315 | 1.00 | 24.30 |
| ATOM | 192 | C | PHE | 697 | 32.956 | −3.205 | −5.846 | 1.00 | 26.76 |
| ATOM | 193 | O | PHE | 697 | 32.641 | −2.393 | −4.972 | 1.00 | 27.12 |
| ATOM | 194 | N | ALA | 698 | 34.219 | −3.495 | −6.140 | 1.00 | 25.86 |
| ATOM | 195 | CA | ALA | 698 | 35.351 | −2.911 | −5.436 | 1.00 | 24.97 |
| ATOM | 196 | CB | ALA | 698 | 36.596 | −3.305 | −6.131 | 1.00 | 25.52 |
| ATOM | 197 | C | ALA | 698 | 35.323 | −1.402 | −5.300 | 1.00 | 25.24 |
| ATOM | 198 | O | ALA | 698 | 35.559 | −0.852 | −4.216 | 1.00 | 24.99 |
| ATOM | 199 | N | ALA | 699 | 35.029 | −0.737 | −6.414 | 1.00 | 25.11 |
| ATOM | 200 | CA | ALA | 699 | 35.001 | 0.717 | −6.490 | 1.00 | 23.76 |
| ATOM | 201 | CB | ALA | 699 | 34.845 | 1.156 | −7.943 | 1.00 | 24.31 |
| ATOM | 202 | C | ALA | 699 | 33.873 | 1.281 | −5.668 | 1.00 | 22.91 |
| ATOM | 203 | O | ALA | 699 | 34.084 | 2.133 | −4.795 | 1.00 | 22.51 |
| ATOM | 204 | N | LEU | 700 | 32.682 | 0.770 | −5.957 | 1.00 | 21.56 |
| ATOM | 205 | CA | LEU | 700 | 31.440 | 1.185 | −5.314 | 1.00 | 20.84 |
| ATOM | 206 | CB | LEU | 700 | 30.274 | 0.397 | −5.937 | 1.00 | 19.59 |
| ATOM | 207 | CG | LEU | 700 | 29.249 | 0.984 | −6.911 | 1.00 | 18.78 |
| ATOM | 208 | CD1 | LEU | 700 | 29.727 | 2.269 | −7.529 | 1.00 | 18.69 |
| ATOM | 209 | CD2 | LEU | 700 | 28.952 | −0.015 | −7.957 | 1.00 | 17.10 |
| ATOM | 210 | C | LEU | 700 | 31.456 | 0.977 | −3.793 | 1.00 | 20.77 |
| ATOM | 211 | O | LEU | 700 | 30.891 | 1.765 | −3.035 | 1.00 | 19.67 |
| ATOM | 212 | N | LEU | 701 | 32.103 | −0.093 | −3.350 | 1.00 | 20.77 |
| ATOM | 213 | CA | LEU | 701 | 32.147 | −0.367 | −1.941 | 1.00 | 20.58 |
| ATOM | 214 | CB | LEU | 701 | 32.099 | −1.871 | −1.670 | 1.00 | 19.52 |
| ATOM | 215 | CG | LEU | 701 | 30.582 | −2.050 | −1.567 | 1.00 | 19.40 |
| ATOM | 216 | CD1 | LEU | 701 | 30.046 | −2.911 | −2.642 | 1.00 | 17.73 |
| ATOM | 217 | CD2 | LEU | 701 | 30.173 | −2.510 | −0.217 | 1.00 | 17.25 |
| ATOM | 218 | C | LEU | 701 | 33.261 | 0.365 | −1.241 | 1.00 | 20.86 |
| ATOM | 219 | O | LEU | 701 | 33.126 | 0.734 | −0.088 | 1.00 | 21.69 |
| ATOM | 220 | N | SER | 702 | 34.356 | 0.615 | −1.937 | 1.00 | 21.06 |
| ATOM | 221 | CA | SER | 702 | 35.406 | 1.378 | −1.316 | 1.00 | 20.96 |
| ATOM | 222 | CB | SER | 702 | 36.632 | 1.400 | −2.190 | 1.00 | 21.52 |

TABLE A-continued

| | | | | | | | | |
|---|---|---|---|---|---|---|---|---|
| ATOM | 223 | OG | SER | 702 | 37.204 | 0.120 | −2.175 | 1.00 | 23.71 |
| ATOM | 224 | C | SER | 702 | 34.874 | 2.791 | −1.105 | 1.00 | 20.81 |
| ATOM | 225 | O | SER | 702 | 35.187 | 3.423 | −0.103 | 1.00 | 20.82 |
| ATOM | 226 | N | SER | 703 | 34.023 | 3.250 | −2.028 | 1.00 | 20.55 |
| ATOM | 227 | CA | SER | 703 | 33.443 | 4.585 | −1.934 | 1.00 | 18.91 |
| ATOM | 228 | CB | SER | 703 | 32.755 | 4.966 | −3.224 | 1.00 | 18.44 |
| ATOM | 229 | OG | SER | 703 | 33.748 | 5.182 | −4.194 | 1.00 | 20.63 |
| ATOM | 230 | C | SER | 703 | 32.470 | 4.678 | −0.793 | 1.00 | 18.35 |
| ATOM | 231 | O | SER | 703 | 32.520 | 5.625 | −0.025 | 1.00 | 18.89 |
| ATOM | 232 | N | LEU | 704 | 31.596 | 3.684 | −0.662 | 1.00 | 17.26 |
| ATOM | 233 | CA | LEU | 704 | 30.639 | 3.687 | 0.432 | 1.00 | 16.37 |
| ATOM | 234 | CB | LEU | 704 | 29.691 | 2.497 | 0.342 | 1.00 | 15.19 |
| ATOM | 235 | CG | LEU | 704 | 28.558 | 2.583 | −0.660 | 1.00 | 14.03 |
| ATOM | 236 | CD1 | LEU | 704 | 27.882 | 1.259 | −0.748 | 1.00 | 12.28 |
| ATOM | 237 | CD2 | LEU | 704 | 27.582 | 3.681 | −0.235 | 1.00 | 14.48 |
| ATOM | 238 | C | LEU | 704 | 31.366 | 3.678 | 1.761 | 1.00 | 16.10 |
| ATOM | 239 | O | LEU | 704 | 30.925 | 4.340 | 2.696 | 1.00 | 16.81 |
| ATOM | 240 | N | ASN | 705 | 32.495 | 2.961 | 1.829 | 1.00 | 16.70 |
| ATOM | 241 | CA | ASN | 705 | 33.307 | 2.863 | 3.049 | 1.00 | 16.66 |
| ATOM | 242 | CB | ASN | 705 | 34.398 | 1.794 | 2.924 | 1.00 | 15.46 |
| ATOM | 243 | CG | ASN | 705 | 33.850 | 0.384 | 2.941 | 1.00 | 16.24 |
| ATOM | 244 | OD1 | ASN | 705 | 34.448 | −0.512 | 2.385 | 1.00 | 16.82 |
| ATOM | 245 | ND2 | ASN | 705 | 32.726 | 0.180 | 3.592 | 1.00 | 16.07 |
| ATOM | 246 | C | ASN | 705 | 33.955 | 4.201 | 3.410 | 1.00 | 17.17 |
| ATOM | 247 | O | ASN | 705 | 33.970 | 4.587 | 4.570 | 1.00 | 17.46 |
| ATOM | 248 | N | GLU | 706 | 34.512 | 4.882 | 2.415 | 1.00 | 17.04 |
| ATOM | 249 | CA | GLU | 706 | 35.151 | 6.193 | 2.598 | 1.00 | 17.55 |
| ATOM | 250 | CB | GLU | 706 | 35.739 | 6.668 | 1.258 | 1.00 | 18.93 |
| ATOM | 251 | CG | GLU | 706 | 36.394 | 8.029 | 1.282 | 1.00 | 21.19 |
| ATOM | 252 | CD | GLU | 706 | 37.488 | 8.146 | 2.347 | 1.00 | 23.68 |
| ATOM | 253 | OE1 | GLU | 706 | 37.586 | 9.225 | 2.978 | 1.00 | 25.14 |
| ATOM | 254 | OE2 | GLU | 706 | 38.246 | 7.175 | 2.569 | 1.00 | 24.37 |
| ATOM | 255 | C | GLU | 706 | 34.089 | 7.180 | 3.069 | 1.00 | 16.10 |
| ATOM | 256 | O | GLU | 706 | 34.313 | 8.023 | 3.950 | 1.00 | 16.62 |
| ATOM | 257 | N | LEU | 707 | 32.927 | 7.076 | 2.445 | 1.00 | 15.13 |
| ATOM | 258 | CA | LEU | 707 | 31.803 | 7.916 | 2.792 | 1.00 | 14.21 |
| ATOM | 259 | CB | LEU | 707 | 30.604 | 7.579 | 1.925 | 1.00 | 12.85 |
| ATOM | 260 | CG | LEU | 707 | 29.318 | 8.262 | 2.328 | 1.00 | 12.03 |
| ATOM | 261 | CD1 | LEU | 707 | 29.537 | 9.745 | 2.280 | 1.00 | 13.09 |
| ATOM | 262 | CD2 | LEU | 707 | 28.252 | 7.889 | 1.374 | 1.00 | 12.74 |
| ATOM | 263 | C | LEU | 707 | 31.461 | 7.634 | 4.228 | 1.00 | 14.91 |
| ATOM | 264 | O | LEU | 707 | 31.121 | 8.557 | 4.980 | 1.00 | 15.85 |
| ATOM | 265 | N | GLY | 708 | 31.532 | 6.358 | 4.602 | 1.00 | 13.93 |
| ATOM | 266 | CA | GLY | 708 | 31.230 | 5.976 | 5.965 | 1.00 | 12.96 |
| ATOM | 267 | C | GLY | 708 | 32.213 | 6.620 | 6.917 | 1.00 | 13.13 |
| ATOM | 268 | O | GLY | 708 | 31.849 | 7.061 | 7.987 | 1.00 | 13.55 |
| ATOM | 269 | N | GLU | 709 | 33.468 | 6.687 | 6.514 | 1.00 | 14.14 |
| ATOM | 270 | CA | GLU | 709 | 34.525 | 7.279 | 7.322 | 1.00 | 15.83 |
| ATOM | 271 | CB | GLU | 709 | 35.874 | 7.046 | 6.658 | 1.00 | 16.73 |
| ATOM | 272 | CG | GLU | 709 | 37.051 | 7.547 | 7.446 | 1.00 | 18.68 |
| ATOM | 273 | CD | GLU | 709 | 37.573 | 6.514 | 8.401 | 1.00 | 21.63 |
| ATOM | 274 | OE1 | GLU | 709 | 36.766 | 5.660 | 8.826 | 1.00 | 23.39 |
| ATOM | 275 | OE2 | GLU | 709 | 38.784 | 6.544 | 8.723 | 1.00 | 23.17 |
| ATOM | 276 | C | GLU | 709 | 34.334 | 8.775 | 7.486 | 1.00 | 16.65 |
| ATOM | 277 | O | GLU | 709 | 34.628 | 9.317 | 8.563 | 1.00 | 17.59 |
| ATOM | 278 | N | ARG | 710 | 33.845 | 9.427 | 6.428 | 1.00 | 16.70 |
| ATOM | 279 | CA | ARG | 710 | 33.616 | 10.869 | 6.418 | 1.00 | 17.32 |
| ATOM | 280 | CB | ARG | 710 | 33.459 | 11.346 | 4.990 | 1.00 | 16.07 |
| ATOM | 281 | CG | ARG | 710 | 34.659 | 11.098 | 4.137 | 1.00 | 16.18 |
| ATOM | 282 | CD | ARG | 710 | 34.329 | 11.498 | 2.706 | 1.00 | 16.39 |
| ATOM | 283 | NE | ARG | 710 | 35.512 | 11.535 | 1.850 | 1.00 | 15.28 |
| ATOM | 284 | CZ | ARG | 710 | 35.587 | 12.246 | 0.733 | 1.00 | 15.30 |
| ATOM | 285 | NH1 | ARG | 710 | 34.550 | 12.975 | 0.357 | 1.00 | 14.96 |
| ATOM | 286 | NH2 | ARG | 710 | 36.691 | 12.242 | 0.001 | 1.00 | 14.89 |
| ATOM | 287 | C | ARG | 710 | 32.376 | 11.230 | 7.218 | 1.00 | 17.85 |
| ATOM | 288 | O | ARG | 710 | 32.379 | 12.156 | 8.034 | 1.00 | 17.75 |
| ATOM | 289 | N | GLN | 711 | 31.291 | 10.516 | 6.955 | 1.00 | 18.71 |
| ATON | 290 | CA | GLN | 711 | 30.067 | 10.745 | 7.697 | 1.00 | 19.38 |
| ATOM | 291 | CB | GLN | 711 | 28.908 | 9.938 | 7.127 | 1.00 | 19.79 |
| ATON | 292 | CG | GLN | 711 | 28.377 | 10.566 | 5.878 | 1.00 | 22.36 |
| ATOM | 293 | CD | GLN | 711 | 27.058 | 10.010 | 5.446 | 1.00 | 23.37 |
| ATOM | 294 | OE1 | GLN | 711 | 26.758 | 9.932 | 4.244 | 1.00 | 25.35 |
| ATOM | 295 | NE2 | GLN | 711 | 26.228 | 9.677 | 6.410 | 1.00 | 24.52 |
| ATOM | 296 | C | GLN | 711 | 30.209 | 10.494 | 9.188 | 1.00 | 19.48 |
| ATOM | 297 | O | GLN | 711 | 29.564 | 11.183 | 9.985 | 1.00 | 19.57 |
| ATOM | 298 | N | LEU | 712 | 31.043 | 9.529 | 9.571 | 1.00 | 18.76 |
| ATOM | 299 | CA | LEU | 712 | 31.259 | 9.227 | 10.984 | 1.00 | 19.20 |
| ATOM | 300 | CB | LEU | 712 | 32.163 | 8.008 | 11.157 | 1.00 | 20.55 |
| ATOM | 301 | CG | LEU | 712 | 32.522 | 7.607 | 12.590 | 1.00 | 21.95 |

TABLE A-continued

| | | | | | | | | |
|---|---|---|---|---|---|---|---|---|
| ATOM | 302 | CD1 | LEU | 712 | 31.288 | 7.641 | 13.484 | 1.00 | 23.43 |
| ATOM | 303 | CD2 | LEU | 712 | 33.132 | 6.223 | 12.586 | 1.00 | 22.57 |
| ATOM | 304 | C | LEU | 712 | 31.876 | 10.428 | 11.704 | 1.00 | 19.23 |
| ATOM | 305 | O | LEU | 712 | 31.507 | 10.743 | 12.834 | 1.00 | 17.65 |
| ATOM | 306 | N | VAL | 713 | 32.809 | 11.099 | 11.039 | 1.00 | 19.70 |
| ATOM | 307 | CA | VAL | 713 | 33.427 | 12.270 | 11.619 | 1.00 | 19.68 |
| ATOM | 308 | CB | VAL | 713 | 34.453 | 12.859 | 10.658 | 1.00 | 20.01 |
| ATOM | 309 | CG1 | VAL | 713 | 34.722 | 14.292 | 11.001 | 1.00 | 21.16 |
| ATOM | 310 | CG2 | VAL | 713 | 35.750 | 12.069 | 10.750 | 1.00 | 20.06 |
| ATOM | 311 | C | VAL | 713 | 32.328 | 13.277 | 11.990 | 1.00 | 19.53 |
| ATOM | 312 | O | VAL | 713 | 32.325 | 13.802 | 13.086 | 1.00 | 20.00 |
| ATOM | 313 | N | HIS | 714 | 31.330 | 13.434 | 11.128 | 1.00 | 19.20 |
| ATOM | 314 | CA | HIS | 714 | 30.215 | 14.356 | 11.358 | 1.00 | 19.47 |
| ATOM | 315 | CB | HIS | 714 | 29.498 | 14.658 | 10.038 | 1.00 | 20.77 |
| ATOM | 316 | CG | HIS | 714 | 30.331 | 15.410 | 9.058 | 1.00 | 21.60 |
| ATOM | 317 | CD2 | HIS | 714 | 31.369 | 15.016 | 8.283 | 1.00 | 22.31 |
| ATOM | 318 | ND1 | HIS | 714 | 30.131 | 16.744 | 8.784 | 1.00 | 22.32 |
| ATOM | 319 | CE1 | HIS | 714 | 31.005 | 17.139 | 7.876 | 1.00 | 23.41 |
| ATOM | 320 | NE2 | HIS | 714 | 31.768 | 16.113 | 7.557 | 1.00 | 23.22 |
| ATOM | 321 | C | HIS | 714 | 29.183 | 13.885 | 12.383 | 1.00 | 18.83 |
| ATOM | 322 | O | HIS | 714 | 28.497 | 14.701 | 13.005 | 1.00 | 18.73 |
| ATOM | 323 | N | VAL | 715 | 29.006 | 12.572 | 12.485 | 1.00 | 18.39 |
| ATOM | 324 | CA | VAL | 715 | 28.063 | 11.972 | 13.434 | 1.00 | 16.86 |
| ATOM | 325 | CB | VAL | 715 | 27.869 | 10.435 | 13.134 | 1.00 | 16.78 |
| ATOM | 326 | CG1 | VAL | 715 | 27.037 | 9.756 | 14.197 | 1.00 | 17.10 |
| ATOM | 327 | CG2 | VAL | 715 | 27.183 | 10.259 | 11.817 | 1.00 | 17.34 |
| ATOM | 328 | C | VAL | 715 | 28.667 | 12.166 | 14.817 | 1.00 | 15.60 |
| ATOM | 329 | O | VAL | 715 | 27.958 | 12.422 | 15.788 | 1.00 | 15.49 |
| ATOM | 330 | N | VAL | 716 | 29.986 | 12.077 | 14.913 | 1.00 | 15.13 |
| ATOM | 331 | CA | VAL | 716 | 30.622 | 12.250 | 16.205 | 1.00 | 15.01 |
| ATOM | 332 | CB | VAL | 716 | 32.136 | 11.885 | 16.158 | 1.00 | 14.93 |
| ATOM | 333 | CG1 | VAL | 716 | 32.825 | 12.233 | 17.481 | 1.00 | 13.26 |
| ATOM | 334 | CG2 | VAL | 716 | 32.310 | 10.373 | 15.870 | 1.00 | 14.26 |
| ATOM | 335 | C | VAL | 716 | 30.419 | 13.681 | 16.708 | 1.00 | 15.83 |
| ATOM | 336 | O | VAL | 716 | 30.129 | 13.883 | 17.887 | 1.00 | 16.61 |
| ATOM | 337 | N | LYS | 717 | 30.544 | 14.665 | 15.816 | 1.00 | 16.59 |
| ATOM | 338 | CA | LYS | 717 | 30.390 | 16.082 | 16.183 | 1.00 | 17.20 |
| ATOM | 339 | CB | LYS | 717 | 30.884 | 16.974 | 15.041 | 1.00 | 18.94 |
| ATOM | 340 | CG | LYS | 717 | 32.361 | 16.747 | 14.698 | 1.00 | 22.56 |
| ATOM | 341 | CD | LYS | 717 | 33.245 | 16.752 | 15.978 | 1.00 | 25.34 |
| ATOM | 342 | CE | LYS | 717 | 34.294 | 15.609 | 16.007 | 1.00 | 27.06 |
| ATOM | 343 | NZ | LYS | 717 | 34.709 | 15.195 | 17.410 | 1.00 | 27.21 |
| ATOM | 344 | C | LYS | 717 | 28.951 | 16.387 | 16.534 | 1.00 | 16.77 |
| ATOM | 345 | O | LYS | 717 | 28.658 | 16.931 | 17.593 | 1.00 | 18.49 |
| ATOM | 346 | N | TRP | 718 | 28.049 | 15.976 | 15.659 | 1.00 | 15.68 |
| ATOM | 347 | CA | TRP | 718 | 26.618 | 16.143 | 15.868 | 1.00 | 14.61 |
| ATOM | 348 | CB | TRP | 718 | 25.889 | 15.442 | 14.689 | 1.00 | 11.97 |
| ATOM | 349 | CG | TRP | 718 | 24.433 | 15.266 | 14.841 | 1.00 | 9.66 |
| ATOM | 350 | CD2 | TRP | 718 | 23.757 | 14.069 | 15.254 | 1.00 | 10.28 |
| ATOM | 351 | CE2 | TRP | 718 | 22.373 | 14.371 | 15.293 | 1.00 | 9.98 |
| ATOM | 352 | CE3 | TRP | 718 | 24.176 | 12.778 | 15.612 | 1.00 | 10.09 |
| ATOM | 353 | CD1 | TRP | 718 | 23.472 | 16.199 | 14.645 | 1.00 | 9.89 |
| ATOM | 354 | NE1 | TRP | 718 | 22.228 | 15.688 | 14.918 | 1.00 | 8.38 |
| ATOM | 355 | CZ2 | TRP | 718 | 21.394 | 13.419 | 15.663 | 1.00 | 9.00 |
| ATOM | 356 | CZ3 | TRP | 718 | 23.201 | 11.835 | 15.980 | 1.00 | 8.20 |
| ATOM | 357 | CH2 | TRP | 718 | 21.835 | 12.171 | 16.004 | 1.00 | 7.32 |
| ATOM | 358 | C | TRP | 718 | 26.200 | 15.562 | 17.261 | 1.00 | 15.34 |
| ATOM | 359 | O | TRP | 718 | 25.659 | 16.269 | 18.124 | 1.00 | 14.55 |
| ATOM | 360 | N | ALA | 719 | 26.468 | 14.272 | 17.464 | 1.00 | 16.10 |
| ATOM | 361 | CA | ALA | 719 | 26.143 | 13.559 | 18.683 | 1.00 | 15.03 |
| ATOM | 362 | CB | ALA | 719 | 26.796 | 12.184 | 18.657 | 1.00 | 13.59 |
| ATOM | 363 | C | ALA | 719 | 26.623 | 14.346 | 19.881 | 1.00 | 15.62 |
| ATOM | 364 | O | ALA | 719 | 25.857 | 14.646 | 20.785 | 1.00 | 15.85 |
| ATOM | 365 | N | LYS | 720 | 27.870 | 14.781 | 19.828 | 1.00 | 17.45 |
| ATOM | 366 | CA | LYS | 720 | 28.463 | 15.516 | 20.924 | 1.00 | 18.63 |
| ATOM | 367 | CB | LYS | 720 | 29.970 | 15.625 | 20.715 | 1.00 | 19.81 |
| ATOM | 368 | CG | LYS | 720 | 30.644 | 14.292 | 21.012 | 1.00 | 21.18 |
| ATOM | 369 | CD | LYS | 720 | 32.136 | 14.334 | 20.860 | 1.00 | 23.81 |
| ATOM | 370 | CE | LYS | 720 | 32.762 | 12.975 | 21.244 | 1.00 | 25.84 |
| ATOM | 371 | NZ | LYS | 720 | 32.729 | 12.661 | 22.708 | 1.00 | 26.70 |
| ATOM | 372 | C | LYS | 720 | 27.822 | 16.860 | 21.204 | 1.00 | 18.98 |
| ATOM | 373 | O | LYS | 720 | 27.921 | 17.377 | 22.321 | 1.00 | 19.86 |
| ATOM | 374 | N | ALA | 721 | 27.070 | 17.369 | 20.238 | 1.00 | 18.21 |
| ATOM | 375 | CA | ALA | 721 | 26.406 | 18.651 | 20.382 | 1.00 | 18.10 |
| ATOM | 376 | CB | ALA | 721 | 26.584 | 19.461 | 19.146 | 1.00 | 17.43 |
| ATOM | 377 | C | ALA | 721 | 24.941 | 18.492 | 20.675 | 1.00 | 18.80 |
| ATOM | 378 | O | ALA | 721 | 24.192 | 19.485 | 20.660 | 1.00 | 19.16 |
| ATOM | 379 | N | LEU | 722 | 24.518 | 17.247 | 20.904 | 1.00 | 19.00 |
| ATOM | 380 | CA | LEU | 722 | 23.119 | 16.912 | 21.207 | 1.00 | 19.60 |

TABLE A-continued

| | | | | | | | | |
|---|---|---|---|---|---|---|---|---|
| ATOM | 381 | CB | LEU | 722 | 22.955 | 15.395 | 21.119 | 1.00 | 19.45 |
| ATOM | 382 | CG | LEU | 722 | 21.855 | 14.771 | 20.271 | 1.00 | 19.62 |
| ATOM | 383 | CD1 | LEU | 722 | 21.540 | 15.657 | 19.099 | 1.00 | 17.02 |
| ATOM | 384 | CD2 | LEU | 722 | 22.298 | 13.382 | 19.815 | 1.00 | 17.38 |
| ATOM | 385 | C | LEU | 722 | 22.754 | 17.362 | 22.616 | 1.00 | 20.27 |
| ATOM | 386 | O | LEU | 722 | 23.521 | 17.125 | 23.549 | 1.00 | 21.72 |
| ATOM | 387 | N | PRO | 723 | 21.574 | 17.992 | 22.811 | 1.00 | 20.65 |
| ATOM | 388 | CD | PRO | 723 | 20.500 | 18.317 | 21.861 | 1.00 | 20.29 |
| ATOM | 389 | CA | PRO | 723 | 21.211 | 18.428 | 24.167 | 1.00 | 21.24 |
| ATON | 390 | CB | PRO | 723 | 19.767 | 18.917 | 23.997 | 1.00 | 20.40 |
| ATOM | 391 | CG | PRO | 723 | 19.706 | 19.349 | 22.624 | 1.00 | 20.05 |
| ATOM | 392 | C | PRO | 723 | 21.266 | 17.287 | 25.195 | 1.00 | 21.66 |
| ATOM | 393 | O | PRO | 723 | 20.821 | 16.165 | 24.935 | 1.00 | 21.14 |
| ATOM | 394 | N | GLY | 724 | 21.800 | 17.588 | 26.369 | 1.00 | 22.02 |
| ATOM | 395 | CA | GLY | 724 | 21.874 | 16.598 | 27.416 | 1.00 | 22.29 |
| ATOM | 396 | C | GLY | 724 | 22.838 | 15.478 | 27.132 | 1.00 | 23.13 |
| ATOM | 397 | O | GLY | 724 | 23.076 | 14.658 | 28.004 | 1.00 | 23.78 |
| ATOM | 398 | N | PHE | 725 | 23.434 | 15.446 | 25.946 | 1.00 | 24.14 |
| ATOM | 399 | CA | PHE | 725 | 24.360 | 14.368 | 25.610 | 1.00 | 24.24 |
| ATOM | 400 | CB | PHE | 725 | 24.915 | 14.554 | 24.214 | 1.00 | 23.59 |
| ATOM | 401 | CG | PHE | 725 | 25.648 | 13.353 | 23.703 | 1.00 | 23.80 |
| ATOM | 402 | CD1 | PHE | 725 | 24.944 | 12.239 | 23.260 | 1.00 | 22.83 |
| ATOM | 403 | CD2 | PHE | 725 | 27.046 | 13.328 | 23.675 | 1.00 | 22.40 |
| ATOM | 404 | CE1 | PHE | 725 | 25.623 | 11.130 | 22.804 | 1.00 | 22.77 |
| ATOM | 405 | CE2 | PHE | 725 | 27.731 | 12.226 | 23.221 | 1.00 | 21.05 |
| ATOM | 406 | CZ | PHE | 725 | 27.025 | 11.123 | 22.784 | 1.00 | 22.31 |
| ATOM | 407 | C | PHE | 725 | 25.505 | 14.170 | 26.582 | 1.00 | 24.85 |
| ATOM | 408 | O | PHE | 725 | 25.873 | 13.028 | 26.863 | 1.00 | 23.79 |
| ATOM | 409 | N | ARG | 726 | 26.083 | 15.270 | 27.070 | 1.00 | 25.97 |
| ATOM | 410 | CA | ARG | 726 | 27.207 | 15.229 | 28.033 | 1.00 | 27.63 |
| ATOM | 411 | CB | ARG | 726 | 27.831 | 16.620 | 28.204 | 1.00 | 29.27 |
| ATOM | 412 | CG | ARG | 726 | 28.622 | 17.087 | 26.995 | 1.00 | 31.68 |
| ATOM | 413 | CD | ARG | 726 | 29.759 | 16.141 | 26.727 | 1.00 | 34.22 |
| ATOM | 414 | NE | ARG | 726 | 30.657 | 16.595 | 25.670 | 1.00 | 37.18 |
| ATOM | 415 | CZ | ARG | 726 | 31.872 | 16.090 | 25.464 | 1.00 | 38.28 |
| ATOM | 416 | NH1 | ARG | 726 | 32.635 | 16.558 | 24.486 | 1.00 | 39.44 |
| ATOM | 417 | NH2 | ARG | 726 | 32.329 | 15.109 | 26.232 | 1.00 | 38.78 |
| ATOM | 418 | C | ARG | 726 | 26.902 | 14.615 | 29.423 | 1.00 | 27.24 |
| ATOM | 419 | O | ARG | 726 | 27.797 | 14.449 | 30.253 | 1.00 | 27.08 |
| ATOM | 420 | N | ASN | 727 | 25.632 | 14.316 | 29.683 | 1.00 | 27.15 |
| ATOM | 421 | CA | ASN | 727 | 25.244 | 13.695 | 30.938 | 1.00 | 26.29 |
| ATOM | 422 | CB | ASN | 727 | 23.717 | 13.687 | 31.115 | 1.00 | 25.46 |
| ATOM | 423 | CG | ASN | 727 | 23.118 | 15.085 | 31.195 | 1.00 | 24.95 |
| ATOM | 424 | OD1 | ASN | 727 | 21.947 | 15.277 | 30.893 | 1.00 | 24.88 |
| ATOM | 425 | ND2 | ASN | 727 | 23.909 | 16.055 | 31.628 | 1.00 | 24.54 |
| ATOM | 426 | C | ASN | 727 | 25.750 | 12.261 | 30.934 | 1.00 | 26.17 |
| ATOM | 427 | O | ASN | 727 | 25.992 | 11.689 | 31.994 | 1.00 | 27.30 |
| ATOM | 428 | N | LEU | 728 | 25.895 | 11.673 | 29.749 | 1.00 | 25.64 |
| ATOM | 429 | CA | LEU | 728 | 26.362 | 10.289 | 29.625 | 1.00 | 25.16 |
| ATOM | 430 | CB | LEU | 728 | 26.191 | 9.759 | 28.190 | 1.00 | 22.98 |
| ATOM | 431 | CG | LEU | 728 | 24.859 | 9.711 | 27.448 | 1.00 | 20.68 |
| ATOM | 432 | CD1 | LEU | 728 | 25.084 | 9.133 | 26.076 | 1.00 | 19.66 |
| ATOM | 433 | CD2 | LEU | 728 | 23.856 | 8.883 | 28.203 | 1.00 | 19.79 |
| ATOM | 434 | C | LEU | 728 | 27.833 | 10.208 | 29.974 | 1.00 | 25.79 |
| ATOM | 435 | O | LEU | 728 | 28.571 | 11.157 | 29.739 | 1.00 | 25.15 |
| ATOM | 436 | N | HIS | 729 | 28.247 | 9.064 | 30.516 | 1.00 | 27.05 |
| ATOM | 437 | CA | HIS | 729 | 29.642 | 8.808 | 30.871 | 1.00 | 28.68 |
| ATOM | 438 | CB | HIS | 729 | 29.737 | 7.455 | 31.570 | 1.00 | 30.72 |
| ATOM | 439 | CG | HIS | 729 | 31.132 | 7.042 | 31.943 | 1.00 | 33.13 |
| ATOM | 440 | CD2 | HIS | 729 | 32.276 | 6.978 | 31.218 | 1.00 | 33.50 |
| ATOM | 441 | ND1 | HIS | 729 | 31.460 | 6.603 | 33.209 | 1.00 | 34.21 |
| ATOM | 442 | CE1 | HIS | 729 | 32.744 | 6.293 | 33.247 | 1.00 | 34.64 |
| ATOM | 443 | NE2 | HIS | 729 | 33.263 | 6.510 | 32.049 | 1.00 | 34.52 |
| ATOM | 444 | C | HIS | 729 | 30.450 | 8.772 | 29.577 | 1.00 | 29.25 |
| ATOM | 445 | O | HIS | 729 | 30.003 | 8.182 | 28.594 | 1.00 | 29.28 |
| ATOM | 446 | N | VAL | 730 | 31.681 | 9.295 | 29.625 | 1.00 | 30.21 |
| ATOM | 447 | CA | VAL | 730 | 32.592 | 9.365 | 28.465 | 1.00 | 31.02 |
| ATOM | 448 | CB | VAL | 730 | 34.036 | 9.793 | 28.898 | 1.00 | 32.08 |
| ATOM | 449 | CG1 | VAL | 730 | 35.077 | 9.446 | 27.811 | 1.00 | 32.91 |
| ATOM | 450 | CG2 | VAL | 730 | 34.074 | 11.284 | 29.176 | 1.00 | 31.86 |
| ATOM | 451 | C | VAL | 730 | 32.662 | 8.108 | 27.600 | 1.00 | 30.89 |
| ATOM | 452 | O | VAL | 730 | 32.704 | 8.192 | 26.371 | 1.00 | 30.40 |
| ATOM | 453 | N | ASP | 731 | 32.770 | 6.956 | 28.244 | 1.00 | 30.81 |
| ATOM | 454 | CA | ASP | 731 | 32.819 | 5.709 | 27.509 | 1.00 | 31.55 |
| ATOM | 455 | CB | ASP | 731 | 33.244 | 4.536 | 28.410 | 1.00 | 36.23 |
| ATOM | 456 | CG | ASP | 731 | 32.966 | 3.152 | 27.771 | 1.00 | 40.32 |
| ATOM | 457 | OD1 | ASP | 731 | 31.837 | 2.619 | 27.974 | 1.00 | 42.21 |
| ATOM | 458 | OD2 | ASP | 731 | 33.867 | 2.599 | 27.075 | 1.00 | 42.23 |
| ATOM | 459 | C | ASP | 731 | 31.474 | 5.425 | 26.889 | 1.00 | 28.94 |

TABLE A-continued

| | | | | | | | | |
|---|---|---|---|---|---|---|---|---|
| ATOM | 460 | O | ASP | 731 | 31.408 | 4.912 | 25.789 | 1.00 | 29.47 |
| ATOM | 461 | N | ASP | 732 | 30.403 | 5.760 | 27.587 | 1.00 | 26.17 |
| ATOM | 462 | CA | ASP | 732 | 29.079 | 5.510 | 27.057 | 1.00 | 24.53 |
| ATOM | 463 | CB | ASP | 732 | 28.024 | 5.711 | 28.119 | 1.00 | 24.04 |
| ATOM | 464 | CG | ASP | 732 | 28.073 | 4.654 | 29.186 | 1.00 | 23.64 |
| ATOM | 465 | OD1 | ASP | 732 | 28.728 | 3.592 | 28.984 | 1.00 | 22.31 |
| ATOM | 466 | OD2 | ASP | 732 | 27.444 | 4.904 | 30.231 | 1.00 | 23.89 |
| ATOM | 467 | C | ASP | 732 | 28.770 | 6.387 | 25.875 | 1.00 | 23.96 |
| ATOM | 468 | O | ASP | 732 | 28.030 | 5.982 | 24.981 | 1.00 | 22.56 |
| ATOM | 469 | N | GLN | 733 | 29.288 | 7.612 | 25.920 | 1.00 | 23.56 |
| ATOM | 470 | CA | GLN | 733 | 29.121 | 8.591 | 24.855 | 1.00 | 22.94 |
| ATOM | 471 | CB | GLN | 733 | 29.942 | 9.847 | 25.166 | 1.00 | 22.73 |
| ATOM | 472 | CG | GLN | 733 | 29.359 | 10.776 | 26.225 | 1.00 | 23.24 |
| ATOM | 473 | CD | GLN | 733 | 30.208 | 12.013 | 26.480 | 1.00 | 23.27 |
| ATOM | 474 | OE1 | GLN | 733 | 30.018 | 12.696 | 27.477 | 1.00 | 24.33 |
| ATOM | 475 | NE2 | GLN | 733 | 31.130 | 12.316 | 25.577 | 1.00 | 23.47 |
| ATOM | 476 | C | GLN | 733 | 29.636 | 7.997 | 23.557 | 1.00 | 23.20 |
| ATOM | 477 | O | GLN | 733 | 28.979 | 8.075 | 22.522 | 1.00 | 23.08 |
| ATOM | 478 | N | MET | 734 | 30.853 | 7.459 | 23.625 | 1.00 | 23.37 |
| ATOM | 479 | CA | MET | 734 | 31.545 | 6.832 | 22.508 | 1.00 | 24.31 |
| ATOM | 480 | CB | MET | 734 | 33.003 | 6.596 | 22.906 | 1.00 | 27.26 |
| ATOM | 481 | CG | MET | 734 | 33.749 | 5.604 | 22.047 | 1.00 | 31.61 |
| ATOM | 482 | SD | MET | 734 | 35.293 | 5.121 | 22.821 | 1.00 | 39.54 |
| ATOM | 483 | CE | MET | 734 | 34.884 | 3.401 | 23.387 | 1.00 | 37.92 |
| ATOM | 484 | C | MET | 734 | 30.902 | 5.510 | 22.077 | 1.00 | 23.31 |
| ATOM | 485 | O | MET | 734 | 30.732 | 5.247 | 20.884 | 1.00 | 23.35 |
| ATOM | 486 | N | ALA | 735 | 30.571 | 4.671 | 23.052 | 1.00 | 21.64 |
| ATOM | 487 | CA | ALA | 735 | 29.939 | 3.390 | 22.788 | 1.00 | 20.44 |
| ATOM | 488 | CB | ALA | 735 | 29.650 | 2.683 | 24.110 | 1.00 | 20.71 |
| ATOM | 489 | C | ALA | 735 | 28.644 | 3.570 | 22.013 | 1.00 | 19.23 |
| ATOM | 490 | O | ALA | 735 | 28.398 | 2.905 | 21.015 | 1.00 | 19.59 |
| ATOM | 491 | N | VAL | 736 | 27.799 | 4.460 | 22.501 | 1.00 | 18.69 |
| ATOM | 492 | CA | VAL | 736 | 26.516 | 4.734 | 21.877 | 1.00 | 17.76 |
| ATOM | 493 | CB | VAL | 736 | 25.742 | 5.771 | 22.760 | 1.00 | 18.30 |
| ATOM | 494 | CG1 | VAL | 736 | 25.373 | 6.998 | 22.011 | 1.00 | 17.05 |
| ATOM | 495 | CG2 | VAL | 736 | 24.544 | 5.118 | 23.420 | 1.00 | 17.25 |
| ATOM | 496 | C | VAL | 736 | 26.673 | 5.133 | 20.389 | 1.00 | 18.16 |
| ATOM | 497 | O | VAL | 736 | 25.962 | 4.614 | 19.512 | 1.00 | 17.42 |
| ATOM | 498 | N | ILE | 737 | 27.658 | 5.985 | 20.096 | 1.00 | 17.60 |
| ATOM | 499 | CA | ILE | 737 | 27.914 | 6.429 | 18.724 | 1.00 | 16.31 |
| ATOM | 500 | CB | ILE | 737 | 29.046 | 7.497 | 18.683 | 1.00 | 14.71 |
| ATOM | 501 | CG2 | ILE | 737 | 29.476 | 7.772 | 17.272 | 1.00 | 14.05 |
| ATOM | 502 | CG1 | ILE | 737 | 28.602 | 8.819 | 19.325 | 1.00 | 15.11 |
| ATOM | 503 | CD1 | ILE | 737 | 29.769 | 9.804 | 19.618 | 1.00 | 12.32 |
| ATOM | 504 | C | ILE | 737 | 28.352 | 5.216 | 17.904 | 1.00 | 16.74 |
| ATOM | 505 | O | ILE | 737 | 27.853 | 4.982 | 16.812 | 1.00 | 16.09 |
| ATOM | 506 | N | GLN | 738 | 29.281 | 4.451 | 18.468 | 1.00 | 18.15 |
| ATOM | 507 | CA | GLN | 738 | 29.850 | 3.260 | 17.845 | 1.00 | 17.97 |
| ATOM | 508 | CB | GLN | 738 | 30.960 | 2.715 | 18.713 | 1.00 | 20.53 |
| ATOM | 509 | CG | GLN | 738 | 32.278 | 3.394 | 18.568 | 1.00 | 23.88 |
| ATOM | 510 | CD | GLN | 738 | 33.306 | 2.726 | 19.439 | 1.00 | 26.69 |
| ATOM | 511 | OE1 | GLN | 738 | 33.027 | 2.390 | 20.593 | 1.00 | 29.30 |
| ATOM | 512 | NE2 | GLN | 738 | 34.483 | 2.475 | 18.887 | 1.00 | 28.53 |
| ATOM | 513 | C | GLN | 738 | 28.904 | 2.111 | 17.548 | 1.00 | 16.76 |
| ATOM | 514 | O | GLN | 738 | 29.249 | 1.226 | 16.788 | 1.00 | 16.47 |
| ATOM | 515 | N | TYR | 739 | 27.792 | 2.029 | 18.260 | 1.00 | 16.39 |
| ATOM | 516 | CA | TYR | 739 | 26.819 | 0.983 | 17.995 | 1.00 | 16.41 |
| ATOM | 517 | CB | TYR | 739 | 26.174 | 0.448 | 19.285 | 1.00 | 15.99 |
| ATOM | 518 | CG | TYR | 739 | 27.130 | −0.115 | 20.313 | 1.00 | 15.68 |
| ATOM | 519 | CD1 | TYR | 739 | 28.251 | −0.852 | 19.950 | 1.00 | 15.41 |
| ATOM | 520 | CE1 | TYR | 739 | 29.151 | −1.317 | 20.915 | 1.00 | 16.17 |
| ATOM | 521 | CD2 | TYR | 739 | 26.925 | 0.131 | 21.656 | 1.00 | 16.49 |
| ATOM | 522 | CE2 | TYR | 739 | 27.817 | −0.321 | 22.624 | 1.00 | 17.09 |
| ATOM | 523 | CZ | TYR | 739 | 28.921 | −1.040 | 22.253 | 1.00 | 16.83 |
| ATOM | 524 | OH | TYR | 739 | 29.787 | −1.435 | 23.256 | 1.00 | 18.24 |
| ATOM | 525 | C | TYR | 739 | 25.721 | 1.527 | 17.100 | 1.00 | 16.45 |
| ATOM | 526 | O | TYR | 739 | 25.138 | 0.793 | 16.295 | 1.00 | 17.63 |
| ATOM | 527 | N | SER | 740 | 25.453 | 2.822 | 17.195 | 1.00 | 15.61 |
| ATOM | 528 | CA | SER | 740 | 24.384 | 3.404 | 16.403 | 1.00 | 15.61 |
| ATOM | 529 | CB | SER | 740 | 23.619 | 4.403 | 17.252 | 1.00 | 15.49 |
| ATOM | 530 | OG | SER | 740 | 24.512 | 5.421 | 17.682 | 1.00 | 18.39 |
| ATOM | 531 | C | SER | 740 | 24.697 | 4.054 | 15.060 | 1.00 | 14.87 |
| ATOM | 532 | O | SER | 740 | 23.778 | 4.451 | 14.376 | 1.00 | 15.75 |
| ATOM | 533 | N | TRP | 741 | 25.948 | 4.188 | 14.659 | 1.00 | 14.33 |
| ATOM | 534 | CA | TRP | 741 | 26.202 | 4.835 | 13.382 | 1.00 | 14.83 |
| ATOM | 535 | CB | TRP | 741 | 27.706 | 4.997 | 13.113 | 1.00 | 15.35 |
| ATOM | 536 | CG | TRP | 741 | 28.465 | 3.720 | 13.000 | 1.00 | 17.05 |
| ATOM | 537 | CD2 | TRP | 741 | 28.765 | 2.987 | 11.800 | 1.00 | 17.91 |
| ATOM | 538 | CE2 | TRP | 741 | 29.467 | 1.834 | 12.190 | 1.00 | 18.98 |

TABLE A-continued

| ATOM | 539 | CE3 | TRP | 741 | 28.505 | 3.193 | 10.434 | 1.00 | 18.66 |
|---|---|---|---|---|---|---|---|---|---|
| ATOM | 540 | CD1 | TRP | 741 | 28.995 | 3.016 | 14.020 | 1.00 | 17.12 |
| ATOM | 541 | NE1 | TRP | 741 | 29.592 | 1.878 | 13.551 | 1.00 | 19.60 |
| ATOM | 542 | CZ2 | TRP | 741 | 29.915 | 0.876 | 11.266 | 1.00 | 18.79 |
| ATOM | 543 | CZ3 | TRP | 741 | 28.949 | 2.240 | 9.509 | 1.00 | 17.91 |
| ATOM | 544 | CH2 | TRP | 741 | 29.644 | 1.098 | 9.934 | 1.00 | 18.35 |
| ATOM | 545 | C | TRP | 741 | 25.471 | 4.246 | 12.166 | 1.00 | 15.12 |
| ATOM | 546 | O | TRP | 741 | 24.902 | 4.995 | 11.376 | 1.00 | 15.56 |
| ATOM | 547 | N | MET | 742 | 25.391 | 2.920 | 12.034 | 1.00 | 14.55 |
| ATOM | 548 | CA | MET | 742 | 24.723 | 2.339 | 10.870 | 1.00 | 12.90 |
| ATOM | 549 | CB | MET | 742 | 24.785 | 0.815 | 10.866 | 1.00 | 13.16 |
| ATOM | 550 | CG | MET | 742 | 24.219 | 0.185 | 9.597 | 1.00 | 12.17 |
| ATOM | 551 | SD | MET | 742 | 25.353 | 0.336 | 8.263 | 1.00 | 15.00 |
| ATOM | 552 | CE | MET | 742 | 26.462 | −0.994 | 8.639 | 1.00 | 13.52 |
| ATOM | 553 | C | MET | 742 | 23.290 | 2.763 | 10.699 | 1.00 | 12.47 |
| ATOM | 554 | O | MET | 742 | 22.886 | 3.153 | 9.610 | 1.00 | 13.31 |
| ATOM | 555 | N | GLY | 743 | 22.497 | 2.656 | 11.748 | 1.00 | 12.12 |
| ATOM | 556 | CA | GLY | 743 | 21.102 | 3.057 | 11.663 | 1.00 | 11.81 |
| ATOM | 557 | C | GLY | 743 | 20.947 | 4.558 | 11.452 | 1.00 | 12.08 |
| ATOM | 558 | O | GLY | 743 | 20.022 | 5.009 | 10.768 | 1.00 | 11.88 |
| ATOM | 559 | N | LEU | 744 | 21.835 | 5.336 | 12.070 | 1.00 | 12.77 |
| ATOM | 560 | CA | LEU | 744 | 21.817 | 6.797 | 11.972 | 1.00 | 12.22 |
| ATOM | 561 | CB | LEU | 744 | 22.884 | 7.418 | 12.888 | 1.00 | 11.70 |
| ATOM | 562 | CG | LEU | 744 | 22.702 | 7.481 | 14.399 | 1.00 | 9.95 |
| ATOM | 563 | CD1 | LEU | 744 | 23.967 | 8.075 | 14.954 | 1.00 | 9.77 |
| ATOM | 564 | CD2 | LEU | 744 | 21.516 | 8.341 | 14.799 | 1.00 | 9.16 |
| ATOM | 565 | C | LEU | 744 | 22.087 | 7.258 | 10.563 | 1.00 | 12.20 |
| ATOM | 566 | O | LEU | 744 | 21.424 | 8.173 | 10.080 | 1.00 | 14.22 |
| ATOM | 567 | N | MET | 745 | 23.083 | 6.651 | 9.921 | 1.00 | 12.34 |
| ATOM | 568 | CA | MET | 745 | 23.466 | 6.991 | 8.541 | 1.00 | 11.39 |
| ATOM | 569 | CB | MET | 745 | 24.839 | 6.427 | 8.191 | 1.00 | 10.75 |
| ATOM | 570 | CG | MET | 745 | 25.961 | 6.948 | 9.076 | 1.00 | 8.86 |
| ATOM | 571 | SD | MET | 745 | 27.509 | 6.429 | 8.487 | 1.00 | 11.97 |
| ATOM | 572 | CE | MET | 745 | 28.579 | 6.939 | 9.717 | 1.00 | 9.84 |
| ATOM | 573 | C | MET | 745 | 22.462 | 6.498 | 7.508 | 1.00 | 12.29 |
| ATOM | 574 | O | MET | 745 | 22.234 | 7.155 | 6.495 | 1.00 | 10.62 |
| ATOM | 575 | N | VAL | 746 | 21.855 | 5.342 | 7.793 | 1.00 | 12.05 |
| ATOM | 576 | CA | VAL | 746 | 20.874 | 4.733 | 6.934 | 1.00 | 11.50 |
| ATOM | 577 | CB | VAL | 746 | 20.524 | 3.315 | 7.426 | 1.00 | 11.19 |
| ATOM | 578 | CG1 | VAL | 746 | 19.245 | 2.852 | 6.811 | 1.00 | 10.17 |
| ATOM | 579 | CG2 | VAL | 746 | 21.615 | 2.355 | 7.095 | 1.00 | 9.64 |
| ATOM | 580 | C | VAL | 746 | 19.605 | 5.565 | 6.942 | 1.00 | 12.13 |
| ATOM | 581 | O | VAL | 746 | 19.000 | 5.792 | 5.907 | 1.00 | 12.72 |
| ATOM | 582 | N | PHE | 747 | 19.227 | 6.051 | 8.117 | 1.00 | 12.64 |
| ATOM | 583 | CA | PHE | 747 | 18.014 | 6.857 | 8.304 | 1.00 | 12.63 |
| ATOM | 584 | CB | PHE | 747 | 17.763 | 7.031 | 9.800 | 1.00 | 11.19 |
| ATOM | 585 | CG | PHE | 747 | 16.411 | 7.542 | 10.126 | 1.00 | 10.00 |
| ATOM | 586 | CD1 | PHE | 747 | 15.286 | 6.780 | 9.847 | 1.00 | 9.30 |
| ATOM | 587 | CD2 | PHE | 747 | 16.253 | 8.798 | 10.700 | 1.00 | 7.79 |
| ATOM | 588 | CE1 | PHE | 747 | 14.008 | 7.260 | 10.136 | 1.00 | 8.30 |
| ATOM | 589 | CE2 | PHE | 747 | 14.996 | 9.293 | 10.993 | 1.00 | 6.75 |
| ATOM | 590 | CZ | PHE | 747 | 13.867 | 8.524 | 10.707 | 1.00 | 8.21 |
| ATOM | 591 | C | PHE | 747 | 18.137 | 8.241 | 7.621 | 1.00 | 13.26 |
| ATOM | 592 | O | PHE | 747 | 17.178 | 8.751 | 7.042 | 1.00 | 13.81 |
| ATOM | 593 | N | ALA | 748 | 19.298 | 8.873 | 7.740 | 1.00 | 12.46 |
| ATOM | 594 | CA | ALA | 748 | 19.513 | 10.172 | 7.119 | 1.00 | 12.97 |
| ATOM | 595 | CB | ALA | 748 | 20.749 | 10.808 | 7.648 | 1.00 | 11.50 |
| ATOM | 596 | C | ALA | 748 | 19.640 | 9.988 | 5.635 | 1.00 | 13.78 |
| ATOM | 597 | O | ALA | 748 | 19.226 | 10.850 | 4.882 | 1.00 | 14.44 |
| ATOM | 598 | N | MET | 749 | 20.209 | 8.864 | 5.204 | 1.00 | 14.54 |
| ATOM | 599 | CA | MET | 749 | 20.381 | 8.578 | 3.782 | 1.00 | 14.78 |
| ATOM | 600 | CB | MET | 749 | 21.241 | 7.331 | 3.607 | 1.00 | 15.28 |
| ATOM | 601 | CG | MET | 749 | 21.622 | 6.945 | 2.199 | 1.00 | 15.33 |
| ATOM | 602 | SD | MET | 749 | 20.315 | 6.246 | 1.193 | 1.00 | 18.79 |
| ATOM | 603 | CE | MET | 749 | 20.226 | 4.627 | 1.835 | 1.00 | 18.82 |
| ATOM | 604 | C | MET | 749 | 19.023 | 8.390 | 3.142 | 1.00 | 15.85 |
| ATOM | 605 | O | MET | 749 | 18.808 | 8.780 | 1.990 | 1.00 | 17.51 |
| ATOM | 606 | N | GLY | 750 | 18.088 | 7.829 | 3.895 | 1.00 | 16.02 |
| ATOM | 607 | CA | GLY | 750 | 16.748 | 7.618 | 3.384 | 1.00 | 16.34 |
| ATOM | 608 | C | GLY | 750 | 16.057 | 8.956 | 3.225 | 1.00 | 17.79 |
| ATOM | 609 | O | GLY | 750 | 15.263 | 9.135 | 2.289 | 1.00 | 19.00 |
| ATOM | 610 | N | TRP | 751 | 16.361 | 9.897 | 4.121 | 1.00 | 17.36 |
| ATOM | 611 | CA | TRP | 751 | 15.778 | 11.241 | 4.091 | 1.00 | 17.99 |
| ATOM | 612 | CB | TRP | 751 | 16.108 | 12.026 | 5.366 | 1.00 | 16.08 |
| ATOM | 613 | CG | TRP | 751 | 15.528 | 13.458 | 5.416 | 1.00 | 14.99 |
| ATOM | 614 | CD2 | TRP | 751 | 14.151 | 13.821 | 5.617 | 1.00 | 13.68 |
| ATOM | 615 | CE2 | TRP | 751 | 14.099 | 15.230 | 5.697 | 1.00 | 12.98 |
| ATOM | 616 | CE3 | TRP | 751 | 12.967 | 13.090 | 5.743 | 1.00 | 14.14 |
| ATOM | 617 | CD1 | TRP | 751 | 16.225 | 14.636 | 5.364 | 1.00 | 13.27 |

TABLE A-continued

| ATOM | 618 | NE1 | TRP | 751 | 15.375 | 15.705 | 5.538 | 1.00 | 12.27 |
|---|---|---|---|---|---|---|---|---|---|
| ATOM | 619 | CZ2 | TRP | 751 | 12.907 | 15.926 | 5.899 | 1.00 | 14.74 |
| ATOM | 620 | CZ3 | TRP | 751 | 11.775 | 13.780 | 5.942 | 1.00 | 14.63 |
| ATOM | 621 | CH2 | TRP | 751 | 11.756 | 15.188 | 6.020 | 1.00 | 14.82 |
| ATOM | 622 | C | TRP | 751 | 16.266 | 11.995 | 2.857 | 1.00 | 18.41 |
| ATOM | 623 | O | TRP | 751 | 15.457 | 12.558 | 2.124 | 1.00 | 20.13 |
| ATOM | 624 | N | ARG | 752 | 17.569 | 11.971 | 2.607 | 1.00 | 19.13 |
| ATOM | 625 | CA | ARG | 752 | 18.150 | 12.616 | 1.431 | 1.00 | 19.06 |
| ATOM | 626 | CB | ARG | 752 | 19.644 | 12.380 | 1.389 | 1.00 | 18.53 |
| ATOM | 627 | CG | ARG | 752 | 20.370 | 12.908 | 2.567 | 1.00 | 18.25 |
| ATOM | 628 | CD | ARG | 752 | 21.870 | 12.901 | 2.317 | 1.00 | 17.24 |
| ATOM | 629 | NE | ARG | 752 | 22.467 | 11.573 | 2.298 | 1.00 | 14.94 |
| ATOM | 630 | CZ | ARG | 752 | 22.976 | 10.973 | 3.370 | 1.00 | 14.90 |
| ATOM | 631 | NH1 | ARG | 752 | 22.928 | 11.561 | 4.554 | 1.00 | 14.75 |
| ATOM | 632 | NH2 | ARG | 752 | 23.684 | 9.864 | 3.240 | 1.00 | 13.87 |
| ATOM | 633 | C | ARG | 752 | 17.572 | 12.077 | 0.138 | 1.00 | 20.27 |
| ATOM | 634 | O | ARG | 752 | 17.392 | 12.815 | −0.828 | 1.00 | 20.66 |
| ATOM | 635 | N | SER | 753 | 17.391 | 10.761 | 0.083 | 1.00 | 22.00 |
| ATOM | 636 | CA | SER | 753 | 16.823 | 10.099 | −1.093 | 1.00 | 22.25 |
| ATOM | 637 | CB | SER | 753 | 16.716 | 8.590 | −0.879 | 1.00 | 20.25 |
| ATOM | 638 | OG | SER | 753 | 17.988 | 8.027 | −0.687 | 1.00 | 19.78 |
| ATOM | 639 | C | SER | 753 | 15.434 | 10.635 | −1.289 | 1.00 | 23.31 |
| ATOM | 640 | O | SER | 753 | 14.978 | 10.803 | −2.409 | 1.00 | 23.88 |
| ATOM | 641 | N | PHE | 754 | 14.762 | 10.870 | −0.173 | 1.00 | 24.76 |
| ATOM | 642 | CA | PHE | 754 | 13.405 | 11.375 | −0.156 | 1.00 | 26.45 |
| ATOM | 643 | CB | PHE | 754 | 12.835 | 11.243 | 1.245 | 1.00 | 26.43 |
| ATOM | 644 | CG | PHE | 754 | 11.447 | 11.765 | 1.364 | 1.00 | 28.06 |
| ATOM | 645 | CD1 | PHE | 754 | 10.407 | 11.168 | 0.654 | 1.00 | 28.69 |
| ATOM | 646 | CD2 | PHE | 754 | 11.184 | 12.895 | 2.118 | 1.00 | 27.96 |
| ATOM | 647 | CE1 | PHE | 754 | 9.126 | 11.703 | 0.687 | 1.00 | 29.47 |
| ATOM | 648 | CE2 | PHE | 754 | 9.901 | 13.442 | 2.160 | 1.00 | 28.93 |
| ATOM | 649 | CZ | PHE | 754 | 8.876 | 12.849 | 1.445 | 1.00 | 29.47 |
| ATOM | 650 | C | PHE | 754 | 13.239 | 12.818 | −0.630 | 1.00 | 27.47 |
| ATOM | 651 | O | PHE | 754 | 12.543 | 13.100 | −1.614 | 1.00 | 26.87 |
| ATOM | 652 | N | THR | 755 | 13.823 | 13.732 | 0.125 | 1.00 | 29.01 |
| ATOM | 653 | CA | THR | 755 | 13.725 | 15.134 | −0.190 | 1.00 | 30.83 |
| ATOM | 654 | CB | THR | 755 | 14.345 | 15.972 | 0.918 | 1.00 | 29.71 |
| ATOM | 655 | OG1 | THR | 755 | 15.669 | 15.524 | 1.183 | 1.00 | 28.99 |
| ATOM | 656 | CG2 | THR | 755 | 13.553 | 15.796 | 2.164 | 1.00 | 29.63 |
| ATOM | 657 | C | THR | 755 | 14.317 | 15.460 | −1.552 | 1.00 | 32.57 |
| ATOM | 658 | O | THR | 755 | 13.841 | 16.358 | −2.234 | 1.00 | 33.24 |
| ATOM | 659 | N | ASN | 756 | 15.262 | 14.639 | −1.991 | 1.00 | 34.71 |
| ATOM | 660 | CA | ASN | 756 | 15.920 | 14.842 | −3.273 | 1.00 | 36.48 |
| ATOM | 661 | CB | ASN | 756 | 17.417 | 14.562 | −3.149 | 1.00 | 36.89 |
| ATOM | 662 | CG | ASN | 756 | 18.137 | 15.616 | −2.344 | 1.00 | 37.02 |
| ATOM | 663 | OD1 | ASN | 756 | 17.563 | 16.237 | −1.456 | 1.00 | 39.11 |
| ATOM | 664 | ND2 | ASN | 756 | 19.392 | 15.844 | −2.668 | 1.00 | 37.24 |
| ATOM | 665 | C | ASN | 756 | 15.360 | 14.065 | −4.457 | 1.00 | 37.88 |
| ATOM | 666 | O | ASN | 756 | 14.684 | 14.628 | −5.313 | 1.00 | 39.57 |
| ATOM | 667 | N | VAL | 757 | 15.654 | 12.773 | −4.518 | 1.00 | 38.99 |
| ATOM | 668 | CA | VAL | 757 | 15.210 | 11.948 | −5.633 | 1.00 | 39.74 |
| ATOM | 669 | CB | VAL | 757 | 16.274 | 10.869 | −5.971 | 1.00 | 39.96 |
| ATOM | 670 | CG1 | VAL | 757 | 17.639 | 11.540 | −6.170 | 1.00 | 40.00 |
| ATOM | 671 | CG2 | VAL | 757 | 16.354 | 9.819 | −4.871 | 1.00 | 39.28 |
| ATOM | 672 | C | VAL | 757 | 13.835 | 11.308 | −5.456 | 1.00 | 39.95 |
| ATOM | 673 | O | VAL | 757 | 13.501 | 10.335 | −6.134 | 1.00 | 40.19 |
| ATOM | 674 | N | ASN | 758 | 13.037 | 11.874 | −4.559 | 1.00 | 40.46 |
| ATOM | 675 | CA | ASN | 758 | 11.699 | 11.374 | −4.265 | 1.00 | 41.28 |
| ATOM | 676 | CB | ASN | 758 | 10.678 | 11.894 | −5.288 | 1.00 | 43.82 |
| ATOM | 677 | CG | ASN | 758 | 10.257 | 13.331 | −5.005 | 1.00 | 44.84 |
| ATOM | 678 | OD1 | ASN | 758 | 11.097 | 14.199 | −4.764 | 1.00 | 46.40 |
| ATOM | 679 | ND2 | ASN | 758 | 8.953 | 13.576 | −4.987 | 1.00 | 45.71 |
| ATOM | 680 | C | ASN | 758 | 11.622 | 9.858 | −4.100 | 1.00 | 40.91 |
| ATOM | 681 | O | ASN | 758 | 10.592 | 9.229 | −4.404 | 1.00 | 40.73 |
| ATOM | 682 | N | SER | 759 | 12.733 | 9.298 | −3.612 | 1.00 | 40.04 |
| ATOM | 683 | CA | SER | 759 | 12.891 | 7.877 | −3.326 | 1.00 | 38.71 |
| ATOM | 684 | CB | SER | 759 | 11.763 | 7.415 | −2.395 | 1.00 | 37.53 |
| ATOM | 685 | OG | SER | 759 | 11.496 | 8.369 | −1.378 | 1.00 | 34.26 |
| ATOM | 686 | C | SER | 759 | 13.027 | 6.921 | −4.532 | 1.00 | 39.24 |
| ATOM | 687 | O | SER | 759 | 12.833 | 5.711 | −4.382 | 1.00 | 39.20 |
| ATOM | 688 | N | ARG | 760 | 13.409 | 7.438 | −5.704 | 1.00 | 39.12 |
| ATOM | 689 | CA | ARG | 760 | 13.564 | 6.589 | −6.892 | 1.00 | 38.62 |
| ATOM | 690 | CB | ARG | 760 | 13.451 | 7.422 | −8.171 | 1.00 | 40.63 |
| ATOM | 691 | CG | ARG | 760 | 13.598 | 6.577 | −9.444 | 1.00 | 44.41 |
| ATOM | 692 | CD | ARG | 760 | 13.903 | 7.394 | −10.715 | 1.00 | 46.97 |
| ATOM | 693 | NE | ARG | 760 | 14.534 | 6.544 | −11.729 | 1.00 | 48.86 |
| ATOM | 694 | CZ | ARG | 760 | 13.875 | 5.797 | −12.614 | 1.00 | 49.74 |
| ATOM | 695 | NH1 | ARG | 760 | 12.542 | 5.795 | −12.649 | 1.00 | 50.04 |
| ATOM | 696 | NH2 | ARG | 760 | 14.553 | 4.969 | −13.398 | 1.00 | 49.46 |

TABLE A-continued

| | | | | | | | | |
|---|---|---|---|---|---|---|---|---|
| ATOM | 697 | C | ARG | 760 | 14.897 | 5.840 | −6.876 | 1.00 | 36.88 |
| ATOM | 698 | O | ARG | 760 | 15.024 | 4.741 | −7.426 | 1.00 | 37.48 |
| ATOM | 699 | N | MET | 761 | 15.902 | 6.466 | −6.275 | 1.00 | 34.87 |
| ATOM | 700 | CA | MET | 761 | 17.238 | 5.890 | −6.159 | 1.00 | 32.21 |
| ATOM | 701 | CB | MET | 761 | 18.171 | 6.510 | −7.194 | 1.00 | 33.77 |
| ATOM | 702 | CG | MET | 761 | 17.588 | 6.682 | −8.571 | 1.00 | 36.10 |
| ATOM | 703 | SD | MET | 761 | 18.859 | 7.115 | −9.788 | 1.00 | 40.36 |
| ATOM | 704 | CE | MET | 761 | 18.737 | 8.904 | −9.809 | 1.00 | 38.10 |
| ATOM | 705 | C | MET | 761 | 17.738 | 6.242 | −4.751 | 1.00 | 29.46 |
| ATOM | 706 | O | MET | 761 | 17.144 | 7.080 | −4.075 | 1.00 | 28.57 |
| ATOM | 707 | N | LEU | 762 | 18.837 | 5.635 | −4.319 | 1.00 | 26.78 |
| ATOM | 708 | CA | LEU | 762 | 19.382 | 5.905 | −2.992 | 1.00 | 24.13 |
| ATOM | 709 | CB | LEU | 762 | 19.956 | 4.637 | −2.393 | 1.00 | 24.05 |
| ATOM | 710 | CG | LEU | 762 | 18.957 | 3.502 | −2.272 | 1.00 | 23.69 |
| ATOM | 711 | CD1 | LEU | 762 | 19.615 | 2.272 | −1.632 | 1.00 | 23.99 |
| ATOM | 712 | CD2 | LEU | 762 | 17.788 | 4.011 | −1.439 | 1.00 | 24.34 |
| ATOM | 713 | C | LEU | 762 | 20.458 | 6.968 | −3.040 | 1.00 | 23.01 |
| ATOM | 714 | O | LEU | 762 | 21.537 | 6.726 | −3.548 | 1.00 | 22.65 |
| ATOM | 715 | N | TYR | 763 | 20.162 | 8.132 | −2.475 | 1.00 | 22.03 |
| ATOM | 716 | CA | TYR | 763 | 21.066 | 9.273 | −2.450 | 1.00 | 20.69 |
| ATOM | 717 | CB | TYR | 763 | 20.250 | 10.540 | −2.266 | 1.00 | 23.12 |
| ATOM | 718 | CG | TYR | 763 | 20.946 | 11.782 | −2.730 | 1.00 | 25.58 |
| ATOM | 719 | CD1 | TYR | 763 | 20.841 | 12.187 | −4.052 | 1.00 | 26.87 |
| ATOM | 720 | CE1 | TYR | 763 | 21.416 | 13.373 | −4.492 | 1.00 | 28.03 |
| ATOM | 721 | CD2 | TYR | 763 | 21.662 | 12.590 | −1.841 | 1.00 | 26.77 |
| ATOM | 722 | CE2 | TYR | 763 | 22.247 | 13.789 | −2.272 | 1.00 | 28.35 |
| ATOM | 723 | CZ | TYR | 763 | 22.107 | 14.172 | −3.604 | 1.00 | 28.85 |
| ATOM | 724 | OH | TYR | 763 | 22.595 | 15.379 | −4.047 | 1.00 | 30.59 |
| ATOM | 725 | C | TYR | 763 | 22.068 | 9.173 | −1.323 | 1.00 | 18.78 |
| ATOM | 726 | O | TYR | 763 | 21.910 | 9.828 | −0.304 | 1.00 | 17.73 |
| ATOM | 727 | N | PHE | 764 | 23.128 | 8.401 | −1.538 | 1.00 | 17.33 |
| ATOM | 728 | CA | PHE | 764 | 24.152 | 8.191 | −0.533 | 1.00 | 16.94 |
| ATOM | 729 | CB | PHE | 764 | 25.086 | 7.078 | −0.956 | 1.00 | 15.91 |
| ATOM | 730 | CG | PHE | 764 | 24.505 | 5.724 | −0.807 | 1.00 | 16.79 |
| ATOM | 731 | CD1 | PHE | 764 | 24.211 | 4.961 | −1.908 | 1.00 | 16.06 |
| ATOM | 732 | CD2 | PHE | 764 | 24.267 | 5.205 | 0.450 | 1.00 | 16.83 |
| ATOM | 733 | CE1 | PHE | 764 | 23.691 | 3.692 | −1.756 | 1.00 | 18.06 |
| ATOM | 734 | CE2 | PHE | 764 | 23.748 | 3.941 | 0.606 | 1.00 | 18.27 |
| ATOM | 735 | CZ | PHE | 764 | 23.458 | 3.176 | −0.496 | 1.00 | 17.80 |
| ATOM | 736 | C | PHE | 764 | 24.964 | 9.441 | −0.375 | 1.00 | 17.39 |
| ATOM | 737 | O | PHE | 764 | 25.379 | 9.797 | 0.734 | 1.00 | 17.28 |
| ATOM | 738 | N | ALA | 765 | 25.224 | 10.084 | −1.503 | 1.00 | 17.00 |
| ATOM | 739 | CA | ALA | 765 | 26.013 | 11.292 | −1.525 | 1.00 | 16.32 |
| ATOM | 740 | CB | ALA | 765 | 27.479 | 10.957 | −1.460 | 1.00 | 16.17 |
| ATOM | 741 | C | ALA | 765 | 25.674 | 11.913 | −2.841 | 1.00 | 16.66 |
| ATOM | 742 | O | ALA | 765 | 25.051 | 11.267 | −3.675 | 1.00 | 16.71 |
| ATOM | 743 | N | PRO | 766 | 26.016 | 13.196 | −3.032 | 1.00 | 17.18 |
| ATOM | 744 | CD | PRO | 766 | 26.544 | 14.169 | −2.064 | 1.00 | 15.41 |
| ATOM | 745 | CA | PRO | 766 | 25.703 | 13.846 | −4.311 | 1.00 | 17.49 |
| ATOM | 746 | CB | PRO | 766 | 26.183 | 15.277 | −4.077 | 1.00 | 17.30 |
| ATOM | 747 | CG | PRO | 766 | 26.002 | 15.451 | −2.608 | 1.00 | 17.07 |
| ATOM | 748 | C | PRO | 766 | 26.429 | 13.161 | −5.481 | 1.00 | 17.65 |
| ATOM | 749 | O | PRO | 766 | 25.923 | 13.099 | −6.598 | 1.00 | 17.73 |
| ATOM | 750 | N | ASP | 767 | 27.578 | 12.569 | −5.166 | 1.00 | 18.27 |
| ATOM | 751 | CA | ASP | 767 | 28.416 | 11.850 | −6.115 | 1.00 | 18.49 |
| ATOM | 752 | CB | ASP | 767 | 29.877 | 12.312 | −5.955 | 1.00 | 18.71 |
| ATOM | 753 | CG | ASP | 767 | 30.413 | 12.135 | −4.525 | 1.00 | 19.47 |
| ATOM | 754 | OD1 | ASP | 767 | 29.611 | 12.038 | −3.569 | 1.00 | 20.31 |
| ATOM | 755 | OD2 | ASP | 767 | 31.650 | 12.102 | −4.348 | 1.00 | 19.04 |
| ATOM | 756 | C | ASP | 767 | 28.330 | 10.317 | −5.981 | 1.00 | 17.79 |
| ATOM | 757 | O | ASP | 767 | 29.191 | 9.594 | −6.476 | 1.00 | 18.69 |
| ATOM | 758 | N | LEU | 768 | 27.334 | 9.820 | −5.267 | 1.00 | 18.04 |
| ATOM | 759 | CA | LEU | 768 | 27.164 | 8.379 | −5.110 | 1.00 | 18.20 |
| ATOM | 760 | CB | LEU | 768 | 27.955 | 7.809 | −3.914 | 1.00 | 17.47 |
| ATOM | 761 | CG | LEU | 768 | 28.032 | 6.263 | −3.786 | 1.00 | 16.12 |
| ATOM | 762 | CD1 | LEU | 768 | 28.641 | 5.671 | −5.047 | 1.00 | 14.30 |
| ATOM | 763 | CD2 | LEU | 768 | 28.850 | 5.846 | −2.563 | 1.00 | 15.17 |
| ATOM | 764 | C | LEU | 768 | 25.690 | 8.129 | −4.930 | 1.00 | 18.58 |
| ATOM | 765 | O | LEU | 768 | 25.184 | 8.068 | −3.812 | 1.00 | 17.79 |
| ATOM | 766 | N | VAL | 769 | 24.979 | 8.156 | −6.048 | 1.00 | 19.79 |
| ATOM | 767 | CA | VAL | 769 | 23.553 | 7.895 | −6.035 | 1.00 | 20.42 |
| ATOM | 768 | CB | VAL | 769 | 22.709 | 9.142 | −6.447 | 1.00 | 19.95 |
| ATOM | 769 | CG1 | VAL | 769 | 23.571 | 10.190 | −7.096 | 1.00 | 20.70 |
| ATOM | 770 | CG2 | VAL | 769 | 21.537 | 8.757 | −7.277 | 1.00 | 19.19 |
| ATOM | 771 | C | VAL | 769 | 23.373 | 6.609 | −6.852 | 1.00 | 20.73 |
| ATOM | 772 | O | VAL | 769 | 23.873 | 6.467 | −7.961 | 1.00 | 22.43 |
| ATOM | 773 | N | PHE | 770 | 22.871 | 5.604 | −6.157 | 1.00 | 19.70 |
| ATOM | 774 | CA | PHE | 770 | 22.683 | 4.277 | −6.681 | 1.00 | 19.29 |
| ATOM | 775 | CB | PHE | 770 | 22.596 | 3.263 | −5.503 | 1.00 | 18.44 |

TABLE A-continued

| | | | | | | | | |
|---|---|---|---|---|---|---|---|---|
| ATOM | 776 | CG | PHE | 770 | 23.930 | 2.757 | −4.996 | 1.00 | 16.41 |
| ATOM | 777 | CD1 | PHE | 770 | 25.079 | 3.546 | −5.053 | 1.00 | 14.52 |
| ATOM | 778 | CD2 | PHE | 770 | 24.025 | 1.468 | −4.459 | 1.00 | 14.96 |
| ATOM | 779 | CE1 | PHE | 770 | 26.291 | 3.070 | −4.588 | 1.00 | 13.39 |
| ATOM | 780 | CE2 | PHE | 770 | 25.243 | 0.979 | −3.983 | 1.00 | 13.90 |
| ATOM | 781 | CZ | PHE | 770 | 26.383 | 1.786 | −4.050 | 1.00 | 13.96 |
| ATOM | 782 | C | PHE | 770 | 21.425 | 4.134 | −7.473 | 1.00 | 19.41 |
| ATOM | 783 | O | PHE | 770 | 20.367 | 4.583 | −7.054 | 1.00 | 19.74 |
| ATOM | 784 | N | ASN | 771 | 21.534 | 3.474 | −8.611 | 1.00 | 20.33 |
| ATOM | 785 | CA | ASN | 771 | 20.363 | 3.157 | −9.410 | 1.00 | 20.23 |
| ATOM | 786 | CB | ASN | 771 | 20.524 | 3.593 | −10.864 | 1.00 | 19.33 |
| ATOM | 787 | CG | ASN | 771 | 21.883 | 3.304 | −11.403 | 1.00 | 18.89 |
| ATOM | 788 | OD1 | ASN | 771 | 22.574 | 2.408 | −10.942 | 1.00 | 19.51 |
| ATOM | 789 | ND2 | ASN | 771 | 22.289 | 4.069 | −12.382 | 1.00 | 19.02 |
| ATOM | 790 | C | ASN | 771 | 20.278 | 1.636 | −9.292 | 1.00 | 21.01 |
| ATOM | 791 | O | ASN | 771 | 21.129 | 1.013 | −8.648 | 1.00 | 20.52 |
| ATOM | 792 | N | GLU | 772 | 19.258 | 1.043 | −9.898 | 1.00 | 22.23 |
| ATOM | 793 | CA | GLU | 772 | 19.056 | −0.393 | −9.841 | 1.00 | 22.51 |
| ATOM | 794 | CB | GLU | 772 | 17.888 | −0.799 | −10.711 | 1.00 | 23.17 |
| ATOM | 795 | CG | GLU | 772 | 16.652 | −0.455 | −10.099 | 1.00 | 24.81 |
| ATOM | 796 | CD | GLU | 772 | 15.761 | −1.672 | −9.724 | 1.00 | 25.41 |
| ATOM | 797 | OE1 | GLU | 772 | 14.624 | −1.488 | −9.252 | 1.00 | 25.33 |
| ATOM | 798 | OE2 | GLU | 772 | 16.265 | −2.803 | −9.913 | 1.00 | 26.23 |
| ATOM | 799 | C | GLU | 772 | 20.282 | −1.102 | −10.303 | 1.00 | 22.96 |
| ATOM | 800 | O | GLU | 772 | 20.631 | −2.148 | −9.785 | 1.00 | 23.89 |
| ATOM | 801 | N | TYR | 773 | 20.961 | −0.531 | −11.276 | 1.00 | 22.51 |
| ATOM | 802 | CA | TYR | 773 | 22.158 | −1.164 | −11.748 | 1.00 | 22.55 |
| ATOM | 803 | CB | TYR | 773 | 22.640 | −0.492 | −13.018 | 1.00 | 22.84 |
| ATOM | 804 | CG | TYR | 773 | 23.825 | −1.191 | −13.593 | 1.00 | 22.80 |
| ATOM | 805 | CD1 | TYR | 773 | 23.680 | −2.384 | −14.304 | 1.00 | 23.02 |
| ATOM | 806 | CE1 | TYR | 773 | 24.791 | −3.041 | −14.837 | 1.00 | 23.77 |
| ATOM | 807 | CD2 | TYR | 773 | 25.095 | −0.671 | −13.418 | 1.00 | 22.59 |
| ATOM | 808 | CE2 | TYR | 773 | 26.198 | −1.309 | −13.938 | 1.00 | 24.43 |
| ATOM | 809 | CZ | TYR | 773 | 26.047 | −2.491 | −14.643 | 1.00 | 24.22 |
| ATOM | 810 | OH | TYR | 773 | 27.172 | −3.094 | −15.155 | 1.00 | 25.98 |
| ATOM | 811 | C | TYR | 773 | 23.254 | −1.167 | −10.680 | 1.00 | 23.17 |
| ATOM | 812 | O | TYR | 773 | 23.969 | −2.170 | −10.523 | 1.00 | 24.08 |
| ATOM | 813 | N | ARG | 774 | 23.432 | −0.444 | −9.982 | 1.00 | 22.85 |
| ATOM | 814 | CA | ARG | 774 | 24.427 | 0.047 | −8.922 | 1.00 | 21.74 |
| ATOM | 815 | CB | ARG | 774 | 24.623 | 1.487 | −8.494 | 1.00 | 22.23 |
| ATOM | 816 | CG | ARG | 774 | 26.026 | 1.952 | −8.735 | 1.00 | 22.58 |
| ATOM | 817 | CD | ARG | 774 | 26.073 | 3.066 | −9.756 | 1.00 | 23.92 |
| ATOM | 818 | NE | ARG | 774 | 26.048 | 4.383 | −9.146 | 1.00 | 24.69 |
| ATOM | 819 | CZ | ARG | 774 | 26.961 | 5.328 | −9.365 | 1.00 | 25.97 |
| ATOM | 820 | NH1 | ARG | 774 | 27.982 | 5.111 | −10.171 | 1.00 | 25.01 |
| ATOM | 821 | NH2 | ARG | 774 | 26.837 | 6.509 | −8.783 | 1.00 | 26.70 |
| ATOM | 822 | C | ARG | 774 | 23.976 | −0.796 | −7.743 | 1.00 | 21.36 |
| ATOM | 823 | O | ARG | 774 | 24.791 | −1.386 | −7.052 | 1.00 | 20.25 |
| ATOM | 824 | N | MET | 775 | 22.669 | −0.854 | −7.512 | 1.00 | 21.93 |
| ATOM | 825 | CA | MET | 775 | 22.136 | −1.681 | −6.439 | 1.00 | 23.85 |
| ATOM | 826 | CB | MET | 775 | 20.614 | −1.582 | −6.380 | 1.00 | 23.42 |
| ATOM | 827 | CG | MET | 775 | 20.121 | −0.241 | −5.955 | 1.00 | 23.46 |
| ATOM | 828 | SD | MET | 775 | 18.333 | −0.199 | −5.865 | 1.00 | 26.50 |
| ATOM | 829 | CE | MET | 775 | 17.909 | 1.086 | −7.064 | 1.00 | 27.26 |
| ATOM | 830 | C | MET | 775 | 22.550 | −3.136 | −6.666 | 1.00 | 25.38 |
| ATOM | 831 | O | MET | 775 | 22.897 | −3.832 | −5.733 | 1.00 | 25.75 |
| ATOM | 832 | N | HIS | 776 | 22.507 | −3.593 | −7.912 | 1.00 | 27.39 |
| ATOM | 833 | CA | HIS | 776 | 22.891 | −4.954 | −8.262 | 1.00 | 28.41 |
| ATOM | 834 | CB | HIS | 776 | 22.418 | −5.302 | −9.684 | 1.00 | 29.01 |
| ATOM | 835 | CG | HIS | 776 | 22.639 | −6.738 | −10.067 | 1.00 | 30.57 |
| ATOM | 836 | CD2 | HIS | 776 | 21.877 | −7.843 | −9.864 | 1.00 | 30.73 |
| ATOM | 837 | ND1 | HIS | 776 | 23.764 | −7.168 | −10.739 | 1.00 | 30.81 |
| ATOM | 838 | CE1 | HIS | 776 | 23.685 | −8.475 | −10.932 | 1.00 | 29.87 |
| ATOM | 839 | NE2 | HIS | 776 | 22.551 | −8.907 | −10.411 | 1.00 | 29.53 |
| ATOM | 840 | C | HIS | 776 | 24.403 | −5.065 | −8.178 | 1.00 | 29.55 |
| ATOM | 841 | O | HIS | 776 | 24.923 | −5.865 | −7.414 | 1.00 | 30.12 |
| ATOM | 842 | N | LYS | 777 | 25.109 | −4.283 | −8.989 | 1.00 | 31.13 |
| ATOM | 843 | CA | LYS | 777 | 26.570 | −4.290 | −8.980 | 1.00 | 32.73 |
| ATOM | 844 | CB | LYS | 777 | 27.130 | −3.481 | −10.161 | 1.00 | 31.29 |
| ATOM | 845 | CG | LYS | 777 | 26.678 | −3.948 | −11.525 | 1.00 | 30.55 |
| ATOM | 846 | CD | LYS | 777 | 27.443 | −5.163 | −12.003 | 1.00 | 29.83 |
| ATOM | 847 | CE | LYS | 777 | 28.928 | −4.856 | −12.116 | 1.00 | 30.35 |
| ATOM | 848 | NZ | LYS | 777 | 29.631 | −5.860 | −12.983 | 1.00 | 30.53 |
| ATOM | 849 | C | LYS | 777 | 27.032 | −3.655 | −7.660 | 1.00 | 34.07 |
| ATOM | 850 | O | LYS | 777 | 27.382 | −2.478 | −7.611 | 1.00 | 36.43 |
| ATOM | 851 | N | SER | 778 | 26.995 | −4.437 | −6.596 | 1.00 | 33.74 |
| ATOM | 852 | CA | SER | 778 | 27.387 | −4.013 | −5.250 | 1.00 | 33.75 |
| ATOM | 853 | CB | SER | 778 | 26.593 | −2.789 | −4.769 | 1.00 | 33.69 |
| ATOM | 854 | OG | SER | 778 | 25.254 | −3.122 | −4.452 | 1.00 | 33.41 |

TABLE A-continued

| | | | | | | | | |
|---|---|---|---|---|---|---|---|---|
| ATOM | 855 | C | SER | 778 | 27.065 | −5.204 | −4.366 | 1.00 | 32.95 |
| ATOM | 856 | O | SER | 778 | 27.447 | −5.260 | −3.194 | 1.00 | 31.80 |
| ATOM | 857 | N | ARG | 779 | 26.344 | −6.149 | −4.974 | 1.00 | 32.09 |
| ATOM | 858 | CA | ARG | 779 | 25.926 | −7.386 | −4.347 | 1.00 | 31.15 |
| ATOM | 859 | CB | ARG | 779 | 27.161 | −8.256 | −4.071 | 1.00 | 30.74 |
| ATOM | 860 | CG | ARG | 779 | 28.065 | −8.415 | −5.299 | 1.00 | 28.19 |
| ATOM | 861 | CD | ARG | 779 | 29.338 | −9.182 | −4.997 | 1.00 | 26.90 |
| ATOM | 862 | NE | ARG | 779 | 30.284 | −9.129 | −6.117 | 1.00 | 26.55 |
| ATOM | 863 | CZ | ARG | 779 | 31.583 | −9.401 | −6.014 | 1.00 | 26.64 |
| ATOM | 864 | NH1 | ARG | 779 | 32.091 | −9.753 | −4.486 | 1.00 | 27.87 |
| ATOM | 865 | NH2 | ARG | 779 | 32.398 | −9.234 | −7.050 | 1.00 | 26.64 |
| ATOM | 866 | C | ARG | 779 | 25.128 | −7.063 | −3.084 | 1.00 | 30.75 |
| ATOM | 867 | O | ARG | 779 | 25.027 | −7.880 | −2.163 | 1.00 | 31.03 |
| ATOM | 868 | N | MET | 780 | 24.521 | −5.875 | −3.097 | 1.00 | 29.82 |
| ATOM | 869 | CA | MET | 780 | 23.721 | −5.381 | −1.990 | 1.00 | 29.36 |
| ATOM | 870 | CB | MET | 780 | 24.295 | −4.068 | −1.473 | 1.00 | 30.17 |
| ATOM | 871 | CG | MET | 780 | 25.194 | −4.191 | −0.277 | 1.00 | 30.12 |
| ATOM | 872 | SD | MET | 780 | 25.835 | −2.592 | 0.168 | 1.00 | 31.24 |
| ATOM | 873 | CE | MET | 780 | 24.525 | −1.995 | 1.114 | 1.00 | 31.13 |
| ATOM | 874 | C | MET | 780 | 22.262 | −5.165 | −2.331 | 1.00 | 29.21 |
| ATOM | 875 | O | MET | 780 | 21.541 | −4.505 | −1.566 | 1.00 | 29.43 |
| ATOM | 876 | N | TYR | 781 | 21.831 | −5.638 | −3.497 | 1.00 | 28.58 |
| ATOM | 877 | CA | TYR | 781 | 20.433 | −5.498 | −3.897 | 1.00 | 28.82 |
| ATOM | 878 | CB | TYR | 781 | 20.229 | −5.985 | −5.338 | 1.00 | 27.73 |
| ATOM | 879 | CG | TYR | 781 | 18.896 | −5.604 | −5.964 | 1.00 | 26.05 |
| ATOM | 880 | CD1 | TYR | 781 | 18.847 | −4.861 | −7.140 | 1.00 | 25.95 |
| ATOM | 881 | CE1 | TYR | 781 | 17.624 | −4.510 | −7.718 | 1.00 | 25.58 |
| ATOM | 882 | CD2 | TYR | 781 | 17.686 | −5.984 | −5.382 | 1.00 | 25.08 |
| ATOM | 883 | CE2 | TYR | 781 | 16.471 | −5.643 | −5.955 | 1.00 | 24.57 |
| ATOM | 884 | CZ | TYR | 781 | 16.446 | −4.904 | −7.115 | 1.00 | 24.77 |
| ATOM | 885 | OH | TYR | 781 | 15.238 | −4.572 | −7.668 | 1.00 | 24.60 |
| ATOM | 886 | C | TYR | 781 | 19.701 | −6.393 | −2.929 | 1.00 | 30.06 |
| ATOM | 887 | O | TYR | 781 | 19.984 | −7.589 | −2.856 | 1.00 | 32.08 |
| ATOM | 888 | N | SER | 782 | 18.730 | −5.821 | −2.235 | 1.00 | 30.74 |
| ATOM | 889 | CA | SER | 782 | 17.935 | −6.500 | −1.198 | 1.00 | 31.41 |
| ATOM | 890 | CB | SER | 782 | 18.551 | −7.836 | −0.726 | 1.00 | 32.82 |
| ATOM | 891 | OG | SER | 782 | 17.785 | −8.438 | 0.308 | 1.00 | 35.91 |
| ATOM | 892 | C | SER | 782 | 18.027 | −5.483 | −0.070 | 1.00 | 30.50 |
| ATOM | 893 | O | SER | 782 | 17.044 | −4.807 | 0.230 | 1.00 | 30.31 |
| ATOM | 894 | N | GLN | 783 | 19.242 | −5.287 | 0.459 | 1.00 | 29.34 |
| ATOM | 895 | CA | GLN | 783 | 19.455 | −4.314 | 1.522 | 1.00 | 28.01 |
| ATOM | 896 | CB | GLN | 783 | 20.900 | −4.309 | 2.020 | 1.00 | 28.40 |
| ATOM | 897 | CG | GLN | 783 | 21.327 | −5.532 | 2.805 | 1.00 | 29.61 |
| ATOM | 898 | CD | GLN | 783 | 21.790 | −6.634 | 1.900 | 1.00 | 32.01 |
| ATOM | 899 | OE1 | GLN | 783 | 21.486 | −6.621 | 0.714 | 1.00 | 33.24 |
| ATOM | 900 | NE2 | GLN | 783 | 22.547 | −7.587 | 2.436 | 1.00 | 32.18 |
| ATOM | 901 | C | GLN | 783 | 19.089 | −2.963 | 0.935 | 1.00 | 26.36 |
| ATOM | 902 | O | GLN | 783 | 18.342 | −2.211 | 1.544 | 1.00 | 26.08 |
| ATOM | 903 | N | CYS | 784 | 19.538 | −2.698 | −0.290 | 1.00 | 25.49 |
| ATOM | 904 | CA | CYS | 784 | 19.212 | −1.439 | −0.956 | 1.00 | 24.45 |
| ATON | 905 | CB | CYS | 784 | 19.951 | −1.312 | −2.294 | 1.00 | 22.82 |
| ATOM | 906 | SG | CYS | 784 | 21.746 | −0.989 | −2.120 | 1.00 | 18.24 |
| ATON | 907 | C | CYS | 784 | 17.698 | −1.290 | −1.146 | 1.00 | 25.03 |
| ATOM | 908 | O | CYS | 784 | 17.155 | −0.183 | −1.044 | 1.00 | 25.67 |
| ATOM | 909 | N | VAL | 785 | 17.003 | −2.406 | −1.360 | 1.00 | 25.25 |
| ATOM | 910 | CA | VAL | 785 | 15.538 | −2.399 | −1.547 | 1.00 | 25.02 |
| ATOM | 911 | CB | VAL | 785 | 14.987 | −3.826 | −1.903 | 1.00 | 25.94 |
| ATOM | 912 | CG1 | VAL | 785 | 13.457 | −3.901 | −1.710 | 1.00 | 26.21 |
| ATOM | 913 | CG2 | VAL | 785 | 15.349 | −4.195 | −3.324 | 1.00 | 26.31 |
| ATOM | 914 | C | VAL | 785 | 14.864 | −1.979 | −0.257 | 1.00 | 23.91 |
| ATOM | 915 | O | VAL | 785 | 13.881 | −1.259 | −0.260 | 1.00 | 24.19 |
| ATOM | 916 | N | ARG | 786 | 15.402 | −2.455 | 0.853 | 1.00 | 25.02 |
| ATOM | 917 | CA | ARG | 786 | 14.855 | −2.158 | 2.165 | 1.00 | 25.39 |
| ATOM | 918 | CB | ARG | 786 | 15.468 | −3.114 | 3.198 | 1.00 | 26.15 |
| ATOM | 919 | CG | ARG | 786 | 15.392 | −4.591 | 2.748 | 1.00 | 28.30 |
| ATOM | 920 | CD | ARG | 786 | 15.314 | −5.583 | 3.900 | 1.00 | 29.76 |
| ATOM | 921 | NE | ARG | 786 | 14.269 | −5.206 | 4.851 | 1.00 | 32.39 |
| ATOM | 922 | CZ | ARG | 786 | 14.292 | −5.475 | 6.157 | 1.00 | 32.41 |
| ATOM | 923 | NH1 | ARG | 786 | 15.301 | −6.153 | 6.701 | 1.00 | 32.09 |
| ATOM | 924 | NH2 | ARG | 786 | 13.326 | −5.001 | 6.932 | 1.00 | 33.31 |
| ATOM | 925 | C | ARG | 786 | 15.083 | −0.679 | 2.520 | 1.00 | 24.71 |
| ATOM | 926 | O | ARG | 786 | 14.180 | −0.001 | 3.030 | 1.00 | 25.52 |
| ATOM | 927 | N | MET | 787 | 16.246 | −0.146 | 2.160 | 1.00 | 23.53 |
| ATOM | 928 | CA | MET | 787 | 16.548 | 1.252 | 2.463 | 1.00 | 22.11 |
| ATOM | 929 | CB | MET | 787 | 18.018 | 1.528 | 2.261 | 1.00 | 20.46 |
| ATOM | 930 | CG | MET | 787 | 18.883 | 0.925 | 3.314 | 1.00 | 17.04 |
| ATOM | 931 | SD | MET | 787 | 20.578 | 0.861 | 2.788 | 1.00 | 20.46 |
| ATOM | 932 | CE | MET | 787 | 21.285 | 1.969 | 3.729 | 1.00 | 20.07 |
| ATOM | 933 | C | MET | 787 | 15.736 | 2.173 | 1.588 | 1.00 | 23.39 |

TABLE A-continued

| | | | | | | | | |
|---|---|---|---|---|---|---|---|---|
| ATOM | 934 | O | MET | 787 | 15.387 | 3.281 | 1.997 | 1.00 | 24.11 |
| ATOM | 935 | N | ARG | 788 | 15.521 | 1.752 | 0.348 | 1.00 | 24.89 |
| ATOM | 936 | CA | ARG | 788 | 14.738 | 2.499 | −0.625 | 1.00 | 26.29 |
| ATOM | 937 | CB | ARG | 788 | 14.833 | 1.790 | −1.980 | 1.00 | 28.55 |
| ATOM | 938 | CG | ARG | 788 | 14.166 | 2.474 | −3.174 | 1.00 | 32.52 |
| ATOM | 939 | CD | ARG | 788 | 14.217 | 1.541 | −4.395 | 1.00 | 35.44 |
| ATOM | 940 | NE | ARG | 788 | 13.426 | 1.996 | −5.540 | 1.00 | 39.11 |
| ATOM | 941 | CZ | ARG | 788 | 13.899 | 2.177 | −6.783 | 1.00 | 41.32 |
| ATOM | 942 | NH1 | ARG | 788 | 15.182 | 1.960 | −7.081 | 1.00 | 41.94 |
| ATOM | 943 | NH2 | ARG | 788 | 13.079 | 2.567 | −7.754 | 1.00 | 41.48 |
| ATOM | 944 | C | ARG | 788 | 13.312 | 2.475 | −0.090 | 1.00 | 26.13 |
| ATOM | 945 | O | ARG | 788 | 12.596 | 3.473 | −0.146 | 1.00 | 26.50 |
| ATOM | 946 | N | HIS | 789 | 12.920 | 1.339 | 0.483 | 1.00 | 26.36 |
| ATOM | 947 | CA | HIS | 789 | 11.587 | 1.173 | 1.052 | 1.00 | 26.76 |
| ATOM | 948 | CB | HIS | 789 | 11.377 | −0.287 | 1.479 | 1.00 | 29.07 |
| ATOM | 949 | CG | HIS | 789 | 9.970 | −0.609 | 1.879 | 1.00 | 30.42 |
| ATOM | 950 | CD2 | HIS | 789 | 8.890 | −0.944 | 1.137 | 1.00 | 31.35 |
| ATOM | 951 | ND1 | HIS | 789 | 9.538 | −0.567 | 3.188 | 1.00 | 32.05 |
| ATOM | 952 | CE1 | HIS | 789 | 8.249 | −0.856 | 3.235 | 1.00 | 32.56 |
| ATOM | 953 | NE2 | HIS | 789 | 7.831 | −1.087 | 2.001 | 1.00 | 32.55 |
| ATOM | 954 | C | HIS | 789 | 11.369 | 2.133 | 2.231 | 1.00 | 26.08 |
| ATOM | 955 | O | HIS | 789 | 10.275 | 2.671 | 2.394 | 1.00 | 25.72 |
| ATOM | 956 | N | LEU | 790 | 12.413 | 2.318 | 3.048 | 1.00 | 25.92 |
| ATOM | 957 | CA | LEU | 790 | 12.433 | 3.234 | 4.218 | 1.00 | 25.41 |
| ATOM | 958 | CB | LEU | 790 | 13.811 | 3.216 | 4.887 | 1.00 | 23.94 |
| ATOM | 959 | CG | LEU | 790 | 14.039 | 3.400 | 6.383 | 1.00 | 23.32 |
| ATOM | 960 | CD1 | LEU | 790 | 15.444 | 3.930 | 6.570 | 1.00 | 22.41 |
| ATOM | 961 | CD2 | LEU | 790 | 13.047 | 4.324 | 7.014 | 1.00 | 23.17 |
| ATOM | 962 | C | LEU | 790 | 12.218 | 4.654 | 3.720 | 1.00 | 25.47 |
| ATOM | 963 | O | LEU | 790 | 11.359 | 5.380 | 4.216 | 1.00 | 25.06 |
| ATOM | 964 | N | SER | 791 | 13.040 | 5.056 | 2.757 | 1.00 | 25.60 |
| ATOM | 965 | CA | SER | 791 | 12.942 | 6.375 | 2.177 | 1.00 | 26.51 |
| ATOM | 966 | CB | SER | 791 | 13.851 | 6.446 | 0.973 | 1.00 | 28.35 |
| ATOM | 967 | OG | SER | 791 | 14.936 | 5.559 | 1.179 | 1.00 | 32.32 |
| ATOM | 968 | C | SER | 791 | 11.521 | 6.561 | 1.716 | 1.00 | 26.02 |
| ATOM | 969 | O | SER | 791 | 10.950 | 7.632 | 1.885 | 1.00 | 26.00 |
| ATOM | 970 | N | GLN | 792 | 10.964 | 5.505 | 1.122 | 1.00 | 26.31 |
| ATOM | 971 | CA | GLN | 792 | 9.600 | 5.526 | 0.610 | 1.00 | 26.32 |
| ATOM | 972 | CB | GLN | 792 | 9.237 | 4.200 | −0.112 | 1.00 | 28.65 |
| ATOM | 973 | CG | GLN | 792 | 9.700 | 4.109 | −1.603 | 1.00 | 30.43 |
| ATOM | 974 | CD | GLN | 792 | 9.421 | 2.749 | −2.277 | 1.00 | 31.95 |
| ATOM | 975 | OE1 | GLN | 792 | 8.479 | 2.607 | −3.062 | 1.00 | 33.53 |
| ATOM | 976 | NE2 | GLN | 792 | 10.273 | 1.764 | −2.007 | 1.00 | 32.31 |
| ATOM | 977 | C | GLN | 792 | 8.629 | 5.836 | 1.721 | 1.00 | 24.88 |
| ATOM | 978 | O | GLN | 792 | 7.702 | 6.610 | 1.528 | 1.00 | 24.96 |
| ATOM | 979 | N | GLU | 793 | 8.886 | 5.301 | 2.907 | 1.00 | 23.72 |
| ATOM | 980 | CA | GLU | 793 | 8.014 | 5.550 | 4.051 | 1.00 | 22.89 |
| ATOM | 981 | CB | GLU | 793 | 8.460 | 4.728 | 5.273 | 1.00 | 23.65 |
| ATOM | 982 | CG | GLU | 793 | 8.555 | 3.199 | 5.055 | 1.00 | 25.18 |
| ATOM | 983 | CD | GLU | 793 | 7.383 | 2.406 | 5.561 | 1.00 | 27.08 |
| ATOM | 984 | OE1 | GLU | 793 | 6.207 | 2.735 | 5.351 | 1.00 | 25.97 |
| ATOM | 985 | OE2 | GLU | 793 | 7.648 | 1.450 | 6.433 | 1.00 | 28.69 |
| ATOM | 986 | C | GLU | 793 | 7.949 | 7.041 | 4.400 | 1.00 | 21.58 |
| ATOM | 987 | O | GLU | 793 | 6.903 | 7.530 | 4.764 | 1.00 | 21.52 |
| ATOM | 988 | N | PHE | 794 | 9.042 | 7.784 | 4.274 | 1.00 | 21.26 |
| ATOM | 989 | CA | PHE | 794 | 8.999 | 9.208 | 4.598 | 1.00 | 20.65 |
| ATOM | 990 | CB | PHE | 794 | 10.334 | 9.890 | 4.323 | 1.00 | 19.81 |
| ATOM | 991 | CG | PHE | 794 | 11.413 | 9.541 | 5.304 | 1.00 | 19.96 |
| ATOM | 992 | CD1 | PHE | 794 | 11.226 | 9.728 | 6.662 | 1.00 | 20.01 |
| ATOM | 993 | CD2 | PHE | 794 | 12.599 | 8.974 | 4.878 | 1.00 | 19.43 |
| ATOM | 994 | CE1 | PHE | 794 | 12.206 | 9.347 | 7.566 | 1.00 | 19.86 |
| ATOM | 995 | CE2 | PHE | 794 | 13.570 | 8.593 | 5.787 | 1.00 | 18.95 |
| ATOM | 996 | CZ | PHE | 794 | 13.374 | 8.777 | 7.118 | 1.00 | 19.37 |
| ATOM | 997 | C | PHE | 794 | 7.929 | 9.863 | 3.759 | 1.00 | 22.26 |
| ATOM | 998 | O | PHE | 794 | 7.387 | 10.906 | 4.138 | 1.00 | 22.19 |
| ATOM | 999 | N | GLY | 795 | 7.688 | 9.270 | 2.585 | 1.00 | 23.81 |
| ATOM | 1000 | CA | GLY | 795 | 6.676 | 9.750 | 1.662 | 1.00 | 25.46 |
| ATOM | 1001 | C | GLY | 795 | 5.309 | 9.232 | 2.037 | 1.00 | 26.19 |
| ATOM | 1002 | O | GLY | 795 | 4.414 | 10.002 | 2.345 | 1.00 | 27.46 |
| ATOM | 1003 | N | TRP | 796 | 5.181 | 7.912 | 2.081 | 1.00 | 27.45 |
| ATOM | 1004 | CA | TRP | 796 | 3.931 | 7.239 | 2.428 | 1.00 | 28.24 |
| ATON | 1005 | CB | TRP | 796 | 4.135 | 5.697 | 2.542 | 1.00 | 27.71 |
| ATOM | 1006 | CG | TRP | 796 | 4.478 | 4.998 | 1.187 | 1.00 | 27.50 |
| ATOM | 1007 | CD2 | TRP | 796 | 5.208 | 3.763 | 0.985 | 1.00 | 26.97 |
| ATOM | 1008 | CE2 | TRP | 796 | 5.312 | 3.556 | −0.417 | 1.00 | 26.72 |
| ATOM | 1009 | CE3 | TRP | 796 | 5.777 | 2.816 | 1.845 | 1.00 | 25.52 |
| ATOM | 1010 | CD1 | TRP | 796 | 4.177 | 5.460 | −0.079 | 1.00 | 27.17 |
| ATOM | 1011 | NE1 | TRP | 796 | 4.676 | 4.601 | −1.035 | 1.00 | 27.59 |
| ATOM | 1012 | CZ2 | TRP | 796 | 5.967 | 2.448 | −0.970 | 1.00 | 25.70 |

TABLE A-continued

| | | | | | | | | |
|---|---|---|---|---|---|---|---|---|
| ATOM | 1013 | CZ3 | TRP | 796 | 6.427 | 1.714 | 1.290 | 1.00 | 25.51 |
| ATOM | 1014 | CH2 | TRP | 796 | 6.514 | 1.543 | −0.106 | 1.00 | 25.42 |
| ATOM | 1015 | C | TRP | 796 | 3.345 | 7.826 | 3.706 | 1.00 | 29.13 |
| ATOM | 1016 | O | TRP | 796 | 2.132 | 8.026 | 3.801 | 1.00 | 29.87 |
| ATOM | 1017 | N | LEU | 797 | 4.223 | 8.212 | 4.632 | 1.00 | 29.96 |
| ATOM | 1018 | CA | LEU | 797 | 3.816 | 8.768 | 5.923 | 1.00 | 29.80 |
| ATOM | 1019 | CB | LEU | 797 | 4.692 | 8.223 | 7.061 | 1.00 | 28.43 |
| ATOM | 1020 | CG | LEU | 797 | 4.552 | 6.736 | 7.383 | 1.00 | 27.68 |
| ATOM | 1021 | CD1 | LEU | 797 | 5.709 | 6.269 | 8.228 | 1.00 | 27.20 |
| ATOM | 1022 | CD2 | LEU | 797 | 3.216 | 6.470 | 8.058 | 1.00 | 26.62 |
| ATOM | 1023 | C | LEU | 797 | 3.864 | 10.260 | 5.991 | 1.00 | 30.39 |
| ATOM | 1024 | O | LEU | 797 | 3.447 | 10.827 | 6.983 | 1.00 | 32.25 |
| ATOM | 1025 | N | GLN | 798 | 4.415 | 10.908 | 4.978 | 1.00 | 31.03 |
| ATOM | 1026 | CA | GLN | 798 | 4.518 | 12.360 | 5.005 | 1.00 | 30.93 |
| ATOM | 1027 | CB | GLN | 798 | 3.117 | 13.030 | 4.964 | 1.00 | 31.58 |
| ATOM | 1028 | CG | GLN | 798 | 2.253 | 12.757 | 3.701 | 1.00 | 32.86 |
| ATOM | 1029 | CD | GLN | 798 | 0.944 | 13.580 | 3.633 | 1.00 | 32.89 |
| ATOM | 1030 | OE1 | GLN | 798 | 0.342 | 13.933 | 4.648 | 1.00 | 33.16 |
| ATOM | 1031 | NE2 | GLN | 798 | 0.521 | 13.892 | 2.421 | 1.00 | 33.46 |
| ATOM | 1032 | C | GLN | 798 | 5.267 | 12.764 | 6.294 | 1.00 | 30.02 |
| ATOM | 1033 | O | GLN | 798 | 4.716 | 13.460 | 7.147 | 1.00 | 30.51 |
| ATOM | 1034 | N | ILE | 799 | 6.497 | 12.283 | 6.462 | 1.00 | 28.60 |
| ATOM | 1035 | CA | ILE | 799 | 7.277 | 12.634 | 7.648 | 1.00 | 27.76 |
| ATOM | 1036 | CB | ILE | 799 | 8.546 | 11.747 | 7.829 | 1.00 | 26.34 |
| ATOM | 1037 | CG2 | ILE | 799 | 9.382 | 12.246 | 9.007 | 1.00 | 25.78 |
| ATOM | 1038 | CG1 | ILE | 799 | 8.168 | 10.286 | 8.046 | 1.00 | 25.57 |
| ATOM | 1039 | CD1 | ILE | 799 | 7.271 | 10.063 | 9.211 | 1.00 | 25.52 |
| ATOM | 1040 | C | ILE | 799 | 7.729 | 14.094 | 7.552 | 1.00 | 28.59 |
| ATOM | 1041 | O | ILE | 799 | 8.181 | 14.552 | 6.496 | 1.00 | 29.81 |
| ATOM | 1042 | N | THR | 800 | 7.610 | 14.790 | 8.678 | 1.00 | 28.71 |
| ATOM | 1043 | CA | THR | 800 | 7.967 | 16.197 | 8.874 | 1.00 | 28.68 |
| ATOM | 1044 | CB | THR | 800 | 7.202 | 16.718 | 10.142 | 1.00 | 29.24 |
| ATOM | 1045 | OG1 | THR | 800 | 5.839 | 17.003 | 9.815 | 1.00 | 31.49 |
| ATOM | 1046 | CG2 | THR | 800 | 7.824 | 17.925 | 10.746 | 1.00 | 29.69 |
| ATOM | 1047 | C | THR | 800 | 9.475 | 16.347 | 9.116 | 1.00 | 28.69 |
| ATOM | 1048 | O | THR | 800 | 10.069 | 15.510 | 9.796 | 1.00 | 29.15 |
| ATOM | 1049 | N | PRO | 801 | 10.116 | 17.407 | 8.565 | 1.00 | 28.18 |
| ATOM | 1050 | CD | PRO | 801 | 9.618 | 18.376 | 7.569 | 1.00 | 27.62 |
| ATOM | 1051 | CA | PRO | 801 | 11.555 | 17.600 | 8.780 | 1.00 | 27.74 |
| ATOM | 1052 | CB | PRO | 801 | 11.797 | 18.983 | 8.178 | 1.00 | 27.08 |
| ATOM | 1053 | CG | PRO | 801 | 10.908 | 18.956 | 7.002 | 1.00 | 26.58 |
| ATOM | 1054 | C | PRO | 801 | 11.907 | 17.570 | 10.271 | 1.00 | 27.38 |
| ATOM | 1055 | O | PRO | 801 | 12.981 | 17.101 | 10.666 | 1.00 | 27.75 |
| ATOM | 1056 | N | GLN | 802 | 10.982 | 18.045 | 11.095 | 1.00 | 27.01 |
| ATOM | 1057 | CA | GLN | 802 | 11.189 | 18.079 | 12.542 | 1.00 | 26.73 |
| ATOM | 1058 | CB | GLN | 802 | 10.316 | 19.162 | 13.192 | 1.00 | 28.09 |
| ATOM | 1059 | CG | GLN | 802 | 10.582 | 20.596 | 12.692 | 1.00 | 29.79 |
| ATOM | 1060 | CD | GLN | 802 | 9.997 | 20.900 | 11.303 | 1.00 | 30.48 |
| ATOM | 1061 | OE1 | GLN | 802 | 8.948 | 20.381 | 10.918 | 1.00 | 30.36 |
| ATOM | 1062 | NE2 | GLN | 802 | 10.660 | 21.782 | 10.571 | 1.00 | 30.57 |
| ATOM | 1063 | C | GLN | 802 | 10.968 | 16.715 | 13.219 | 1.00 | 24.81 |
| ATOM | 1064 | O | GLN | 802 | 11.599 | 16.415 | 14.222 | 1.00 | 24.41 |
| ATOM | 1065 | N | GLU | 803 | 10.064 | 15.904 | 12.669 | 1.00 | 23.52 |
| ATOM | 1066 | CA | GLU | 803 | 9.797 | 14.558 | 13.196 | 1.00 | 21.64 |
| ATOM | 1067 | CB | GLU | 803 | 8.632 | 13.897 | 12.459 | 1.00 | 20.29 |
| ATOM | 1068 | CG | GLU | 803 | 7.277 | 14.434 | 12.848 | 1.00 | 18.44 |
| ATOM | 1069 | CD | GLU | 803 | 6.147 | 13.786 | 12.119 | 1.00 | 17.84 |
| ATOM | 1070 | OE1 | GLU | 803 | 6.308 | 13.392 | 10.958 | 1.00 | 18.19 |
| ATOM | 1071 | OE2 | GLU | 803 | 5.065 | 13.680 | 12.704 | 1.00 | 19.88 |
| ATOM | 1072 | C | GLU | 803 | 11.067 | 13.784 | 12.923 | 1.00 | 21.04 |
| ATOM | 1073 | O | GLU | 803 | 11.537 | 13.042 | 13.777 | 1.00 | 20.89 |
| ATOM | 1074 | N | PHE | 804 | 11.612 | 14.001 | 11.722 | 1.00 | 19.87 |
| ATOM | 1075 | CA | PHE | 804 | 12.863 | 13.418 | 11.254 | 1.00 | 19.24 |
| ATOM | 1076 | CB | PHE | 804 | 13.144 | 13.867 | 9.822 | 1.00 | 17.23 |
| ATOM | 1077 | CG | PHE | 804 | 14.557 | 13.645 | 9.384 | 1.00 | 14.85 |
| ATOM | 1078 | CD1 | PHE | 804 | 15.012 | 12.380 | 9.095 | 1.00 | 13.76 |
| ATOM | 1079 | CD2 | PHE | 804 | 15.440 | 14.706 | 9.301 | 1.00 | 13.69 |
| ATOM | 1080 | CE1 | PHE | 804 | 16.335 | 12.160 | 8.729 | 1.00 | 13.79 |
| ATOM | 1081 | CE2 | PHE | 804 | 16.765 | 14.496 | 8.936 | 1.00 | 13.36 |
| ATOM | 1082 | CZ | PHE | 804 | 17.214 | 13.217 | 8.647 | 1.00 | 12.84 |
| ATOM | 1083 | C | PHE | 804 | 14.034 | 13.802 | 12.157 | 1.00 | 20.31 |
| ATOM | 1084 | O | PHE | 804 | 14.807 | 12.939 | 12.564 | 1.00 | 21.30 |
| ATOM | 1085 | N | LEU | 805 | 14.187 | 15.086 | 12.463 | 1.00 | 20.30 |
| ATOM | 1086 | CA | LEU | 805 | 15.271 | 15.503 | 13.339 | 1.00 | 20.09 |
| ATOM | 1087 | CB | LEU | 805 | 15.250 | 17.008 | 13.582 | 1.00 | 19.58 |
| ATOM | 1088 | CG | LEU | 805 | 15.552 | 17.834 | 12.330 | 1.00 | 20.47 |
| ATOM | 1089 | CD1 | LEU | 805 | 15.704 | 19.281 | 12.707 | 1.00 | 19.84 |
| ATOM | 1090 | CD2 | LEU | 805 | 16.816 | 17.343 | 11.670 | 1.00 | 19.41 |
| ATOM | 1091 | C | LEU | 805 | 15.172 | 14.767 | 14.651 | 1.00 | 19.83 |

TABLE A-continued

| | | | | | | | | |
|---|---|---|---|---|---|---|---|---|
| ATOM | 1092 | O | LEU | 805 | 16.142 | 14.205 | 15.106 | 1.00 | 20.77 |
| ATOM | 1093 | N | CYS | 806 | 13.980 | 14.719 | 15.223 | 1.00 | 20.17 |
| ATOM | 1094 | CA | CYS | 806 | 13.765 | 14.026 | 16.494 | 1.00 | 21.27 |
| ATOM | 1095 | CB | CYS | 806 | 12.372 | 14.332 | 17.078 | 1.00 | 22.13 |
| ATOM | 1096 | SG | CYS | 806 | 12.142 | 16.017 | 17.706 | 1.00 | 27.50 |
| ATOM | 1097 | C | CYS | 806 | 13.938 | 12.515 | 16.378 | 1.00 | 20.36 |
| ATOM | 1098 | O | CYS | 806 | 14.575 | 11.904 | 17.241 | 1.00 | 20.30 |
| ATOM | 1099 | N | MET | 807 | 13.348 | 11.903 | 15.350 | 1.00 | 19.67 |
| ATOM | 1100 | CA | MET | 807 | 13.491 | 10.458 | 15.160 | 1.00 | 18.10 |
| ATOM | 1101 | CB | MET | 807 | 12.668 | 9.944 | 13.989 | 1.00 | 17.25 |
| ATOM | 1102 | CG | MET | 807 | 11.195 | 9.877 | 14.279 | 1.00 | 16.70 |
| ATOM | 1103 | SD | MET | 807 | 10.377 | 9.142 | 12.911 | 1.00 | 19.42 |
| ATOM | 1104 | CE | MET | 807 | 10.144 | 10.560 | 11.908 | 1.00 | 16.21 |
| ATOM | 1105 | C | MET | 807 | 14.947 | 10.062 | 14.979 | 1.00 | 17.75 |
| ATOM | 1106 | O | MET | 807 | 15.371 | 9.038 | 15.490 | 1.00 | 18.41 |
| ATOM | 1107 | N | LYS | 808 | 15.712 | 10.871 | 14.257 | 1.00 | 17.31 |
| ATOM | 1108 | CA | LYS | 808 | 17.116 | 10.592 | 14.054 | 1.00 | 16.27 |
| ATOM | 1109 | CB | LYS | 808 | 17.729 | 11.514 | 12.994 | 1.00 | 15.01 |
| ATOM | 1110 | CG | LYS | 808 | 19.171 | 11.154 | 12.733 | 1.00 | 14.63 |
| ATOM | 1111 | CD | LYS | 808 | 19.679 | 11.569 | 11.371 | 1.00 | 15.42 |
| ATOM | 1112 | CE | LYS | 808 | 19.422 | 13.053 | 11.092 | 1.00 | 15.64 |
| ATOM | 1113 | NZ | LYS | 808 | 20.232 | 13.940 | 11.928 | 1.00 | 14.15 |
| ATOM | 1114 | C | LYS | 808 | 17.857 | 10.726 | 15.376 | 1.00 | 16.89 |
| ATOM | 1115 | O | LYS | 808 | 18.731 | 9.908 | 15.677 | 1.00 | 16.07 |
| ATOM | 1116 | N | ALA | 809 | 17.522 | 11.747 | 16.166 | 1.00 | 16.53 |
| ATOM | 1117 | CA | ALA | 809 | 18.175 | 11.931 | 17.461 | 1.00 | 17.68 |
| ATOM | 1118 | CB | ALA | 809 | 17.628 | 13.139 | 18.155 | 1.00 | 16.91 |
| ATOM | 1119 | C | ALA | 809 | 17.989 | 10.691 | 18.348 | 1.00 | 19.03 |
| ATOM | 1120 | O | ALA | 809 | 18.932 | 10.207 | 18.996 | 1.00 | 20.50 |
| ATOM | 1121 | N | LEU | 810 | 16.766 | 10.184 | 18.392 | 1.00 | 19.36 |
| ATOM | 1122 | CA | LEU | 810 | 16.459 | 9.011 | 19.186 | 1.00 | 18.99 |
| ATOM | 1123 | CB | LEU | 810 | 14.966 | 8.811 | 19.263 | 1.00 | 19.09 |
| ATOM | 1124 | CG | LEU | 810 | 14.406 | 9.020 | 20.651 | 1.00 | 20.20 |
| ATOM | 1125 | CD1 | LEU | 810 | 12.954 | 8.606 | 20.594 | 1.00 | 21.29 |
| ATOM | 1126 | CD2 | LEU | 810 | 15.176 | 8.199 | 21.674 | 1.00 | 18.75 |
| ATOM | 1127 | C | LEU | 810 | 17.116 | 7.716 | 18.722 | 1.00 | 18.88 |
| ATOM | 1128 | O | LEU | 810 | 17.213 | 6.780 | 19.509 | 1.00 | 20.78 |
| ATOM | 1129 | N | LEU | 811 | 17.537 | 7.636 | 17.456 | 1.00 | 17.63 |
| ATOM | 1130 | CA | LEU | 811 | 18.215 | 6.447 | 16.959 | 1.00 | 15.58 |
| ATOM | 1131 | CB | LEU | 811 | 18.346 | 6.456 | 15.438 | 1.00 | 14.70 |
| ATOM | 1132 | CG | LEU | 811 | 17.148 | 6.107 | 14.574 | 1.00 | 14.14 |
| ATOM | 1133 | CD1 | LEU | 811 | 17.511 | 6.408 | 13.164 | 1.00 | 13.66 |
| ATOM | 1134 | CD2 | LEU | 811 | 16.744 | 4.632 | 14.746 | 1.00 | 13.62 |
| ATOM | 1135 | C | LEU | 811 | 19.598 | 6.328 | 17.582 | 1.00 | 15.42 |
| ATOM | 1136 | O | LEU | 811 | 20.189 | 5.252 | 17.554 | 1.00 | 17.27 |
| ATOM | 1137 | N | LEU | 812 | 20.153 | 7.429 | 18.084 | 1.00 | 13.97 |
| ATOM | 1138 | CA | LEU | 812 | 21.455 | 7.373 | 18.734 | 1.00 | 12.94 |
| ATOM | 1139 | CB | LEU | 812 | 22.004 | 8.790 | 18.937 | 1.00 | 12.69 |
| ATOM | 1140 | CG | LEU | 812 | 23.342 | 8.893 | 19.670 | 1.00 | 12.03 |
| ATOM | 1141 | CD1 | LEU | 812 | 24.488 | 8.422 | 18.802 | 1.00 | 12.16 |
| ATOM | 1142 | CD2 | LEU | 812 | 23.559 | 10.325 | 20.037 | 1.00 | 13.12 |
| ATOM | 1143 | C | LEU | 812 | 21.330 | 6.658 | 20.098 | 1.00 | 12.97 |
| ATOM | 1144 | O | LEU | 812 | 22.282 | 6.118 | 20.629 | 1.00 | 12.99 |
| ATOM | 1145 | N | PHE | 813 | 20.136 | 6.681 | 20.662 | 1.00 | 13.55 |
| ATOM | 1146 | CA | PHE | 813 | 19.859 | 6.064 | 21.950 | 1.00 | 14.19 |
| ATOM | 1147 | CB | PHE | 813 | 19.137 | 7.088 | 22.821 | 1.00 | 15.20 |
| ATOM | 1148 | CG | PHE | 813 | 19.818 | 8.435 | 22.841 | 1.00 | 16.11 |
| ATOM | 1149 | CD1 | PHE | 813 | 20.946 | 8.640 | 23.624 | 1.00 | 15.97 |
| ATOM | 1150 | CD2 | PHE | 813 | 19.349 | 9.472 | 22.036 | 1.00 | 16.07 |
| ATOM | 1151 | CE1 | PHE | 813 | 21.604 | 9.845 | 23.615 | 1.00 | 18.37 |
| ATOM | 1152 | CE2 | PHE | 813 | 19.991 | 10.687 | 22.014 | 1.00 | 17.54 |
| ATOM | 1153 | CZ | PHE | 813 | 21.126 | 10.883 | 22.801 | 1.00 | 17.99 |
| ATOM | 1154 | C | PHE | 813 | 18.971 | 4.856 | 21.753 | 1.00 | 14.71 |
| ATOM | 1155 | O | PHE | 813 | 18.058 | 4.618 | 22.530 | 1.00 | 14.79 |
| ATOM | 1156 | N | SER | 814 | 19.255 | 4.082 | 20.709 | 1.00 | 16.09 |
| ATOM | 1157 | CA | SER | 814 | 18.453 | 2.917 | 20.369 | 1.00 | 15.96 |
| ATOM | 1158 | CB | SER | 814 | 17.697 | 3.172 | 19.062 | 1.00 | 15.79 |
| ATOM | 1159 | OG | SER | 814 | 16.640 | 4.087 | 19.274 | 1.00 | 15.51 |
| ATOM | 1160 | C | SER | 814 | 19.169 | 1.581 | 20.294 | 1.00 | 16.05 |
| ATOM | 1161 | O | SER | 814 | 18.610 | 0.620 | 19.779 | 1.00 | 17.02 |
| ATOM | 1162 | N | ILE | 815 | 20.395 | 1.498 | 20.779 | 1.00 | 16.07 |
| ATOM | 1163 | CA | ILE | 815 | 21.099 | 0.226 | 20.747 | 1.00 | 17.04 |
| ATOM | 1164 | CB | ILE | 815 | 21.620 | −0.086 | 19.325 | 1.00 | 16.75 |
| ATOM | 1165 | CG2 | ILE | 815 | 22.222 | 1.113 | 18.706 | 1.00 | 17.43 |
| ATOM | 1166 | CG1 | ILE | 815 | 22.600 | −1.245 | 19.341 | 1.00 | 17.01 |
| ATOM | 1167 | CD1 | ILE | 815 | 22.915 | −1.753 | 17.953 | 1.00 | 17.98 |
| ATOM | 1168 | C | ILE | 815 | 22.172 | 0.187 | 21.826 | 1.00 | 17.86 |
| ATOM | 1169 | O | ILE | 815 | 23.111 | 0.981 | 21.802 | 1.00 | 18.49 |
| ATOM | 1170 | N | ILE | 816 | 21.994 | −0.700 | 22.809 | 1.00 | 18.25 |

TABLE A-continued

| | | | | | | | | |
|---|---|---|---|---|---|---|---|---|
| ATOM | 1171 | CA | ILE | 816 | 22.913 | −0.804 | 23.947 | 1.00 | 18.91 |
| ATOM | 1172 | CB | ILE | 816 | 22.298 | −0.099 | 25.178 | 1.00 | 19.07 |
| ATOM | 1173 | CG2 | ILE | 816 | 22.175 | 1.378 | 24.921 | 1.00 | 17.73 |
| ATOM | 1174 | CG1 | ILE | 816 | 20.939 | −0.692 | 25.537 | 1.00 | 18.04 |
| ATOM | 1175 | CD1 | ILE | 816 | 20.516 | −0.346 | 26.933 | 1.00 | 17.73 |
| ATOM | 1176 | C | ILE | 816 | 23.302 | −2.226 | 24.385 | 1.00 | 20.13 |
| ATOM | 1177 | O | ILE | 816 | 22.615 | −3.184 | 24.040 | 1.00 | 20.43 |
| ATOM | 1178 | N | PRO | 817 | 24.392 | −2.385 | 25.180 | 1.00 | 20.85 |
| ATOM | 1179 | CD | PRO | 817 | 25.303 | −1.373 | 25.730 | 1.00 | 21.00 |
| ATOM | 1180 | CA | PRO | 817 | 24.805 | −3.720 | 25.631 | 1.00 | 22.05 |
| ATOM | 1181 | CB | PRO | 817 | 26.016 | −3.444 | 26.523 | 1.00 | 21.47 |
| ATOM | 1182 | CG | PRO | 817 | 26.554 | −2.197 | 26.001 | 1.00 | 21.80 |
| ATOM | 1183 | C | PRO | 817 | 23.706 | −4.320 | 26.458 | 1.00 | 22.95 |
| ATOM | 1184 | O | PRO | 817 | 22.988 | −3.594 | 27.151 | 1.00 | 23.12 |
| ATOM | 1185 | N | VAL | 818 | 23.585 | −5.640 | 26.418 | 1.00 | 24.79 |
| ATOM | 1186 | CA | VAL | 818 | 22.544 | −6.316 | 27.195 | 1.00 | 26.35 |
| ATOM | 1187 | CB | VAL | 818 | 22.513 | −7.860 | 26.916 | 1.00 | 27.19 |
| ATOM | 1188 | CG1 | VAL | 818 | 23.864 | −8.515 | 27.282 | 1.00 | 27.82 |
| ATOM | 1189 | CG2 | VAL | 818 | 21.362 | −8.524 | 27.676 | 1.00 | 27.72 |
| ATOM | 1190 | C | VAL | 818 | 22.742 | −6.047 | 28.692 | 1.00 | 26.79 |
| ATOM | 1191 | O | VAL | 818 | 21.777 | −5.849 | 29.421 | 1.00 | 26.79 |
| ATOM | 1192 | N | ASP | 819 | 23.992 | −5.963 | 29.136 | 1.00 | 27.83 |
| ATOM | 1193 | CA | ASP | 819 | 24.240 | −5.732 | 30.550 | 1.00 | 29.78 |
| ATOM | 1194 | CB | ASP | 819 | 25.406 | −6.593 | 31.063 | 1.00 | 32.59 |
| ATOM | 1195 | CG | ASP | 819 | 26.747 | −5.908 | 30.959 | 1.00 | 35.35 |
| ATOM | 1196 | OD1 | ASP | 819 | 27.117 | −5.518 | 29.825 | 1.00 | 38.62 |
| ATOM | 1197 | OD2 | ASP | 819 | 27.431 | −5.776 | 32.011 | 1.00 | 36.18 |
| ATOM | 1198 | C | ASP | 819 | 24.377 | −4.266 | 30.937 | 1.00 | 29.73 |
| ATOM | 1199 | O | ASP | 819 | 24.899 | −3.930 | 32.007 | 1.00 | 30.00 |
| ATOM | 1200 | N | GLY | 820 | 23.839 | −3.403 | 30.085 | 1.00 | 29.43 |
| ATOM | 1201 | CA | GLY | 820 | 23.878 | −1.974 | 30.342 | 1.00 | 28.69 |
| ATOM | 1202 | C | GLY | 820 | 25.216 | −1.317 | 30.125 | 1.00 | 27.42 |
| ATOM | 1203 | O | GLY | 820 | 26.221 | −1.982 | 29.938 | 1.00 | 26.73 |
| ATOM | 1204 | N | LEU | 821 | 25.208 | 0.010 | 30.135 | 1.00 | 28.29 |
| ATOM | 1205 | CA | LEU | 821 | 26.410 | 0.831 | 29.947 | 1.00 | 28.64 |
| ATOM | 1206 | CB | LEU | 821 | 26.023 | 2.110 | 29.195 | 1.00 | 28.29 |
| ATOM | 1207 | CG | LEU | 821 | 25.083 | 1.940 | 27.991 | 1.00 | 28.32 |
| ATOM | 1208 | CD1 | LEU | 821 | 24.046 | 3.022 | 28.031 | 1.00 | 27.27 |
| ATOM | 1209 | CD2 | LEU | 821 | 25.831 | 1.953 | 26.653 | 1.00 | 27.18 |
| ATOM | 1210 | C | LEU | 821 | 26.948 | 1.164 | 31.349 | 1.00 | 28.62 |
| ATOM | 1211 | O | LEU | 821 | 26.341 | 0.747 | 32.342 | 1.00 | 28.84 |
| ATOM | 1212 | N | LYS | 822 | 28.060 | 1.897 | 31.441 | 1.00 | 28.49 |
| ATOM | 1213 | CA | LYS | 822 | 28.642 | 2.268 | 32.741 | 1.00 | 29.80 |
| ATOM | 1214 | CB | LYS | 822 | 29.865 | 3.169 | 32.576 | 1.00 | 30.45 |
| ATOM | 1215 | CG | LYS | 822 | 30.924 | 2.626 | 31.666 | 1.00 | 32.84 |
| ATOM | 1216 | CD | LYS | 822 | 31.517 | 1.345 | 32.194 | 1.00 | 35.27 |
| ATOM | 1217 | CE | LYS | 822 | 32.433 | 0.688 | 31.161 | 1.00 | 36.20 |
| ATOM | 1218 | NZ | LYS | 822 | 33.498 | 1.623 | 30.710 | 1.00 | 37.22 |
| ATOM | 1219 | C | LYS | 822 | 27.621 | 3.016 | 33.587 | 1.00 | 30.25 |
| ATOM | 1220 | O | LYS | 822 | 27.353 | 2.655 | 34.731 | 1.00 | 31.02 |
| ATOM | 1221 | N | ASN | 823 | 27.065 | 4.080 | 33.029 | 1.00 | 29.98 |
| ATOM | 1222 | CA | ASN | 823 | 26.070 | 4.852 | 33.735 | 1.00 | 29.55 |
| ATOM | 1223 | CB | ASN | 823 | 26.458 | 6.323 | 33.774 | 1.00 | 31.17 |
| ATOM | 1224 | CG | ASN | 823 | 27.832 | 6.544 | 34.350 | 1.00 | 32.55 |
| ATOM | 1225 | OD1 | ASN | 823 | 28.787 | 5.856 | 33.985 | 1.00 | 33.56 |
| ATOM | 1226 | ND2 | ASN | 823 | 27.952 | 7.520 | 35.246 | 1.00 | 34.42 |
| ATOM | 1227 | C | ASN | 823 | 24.807 | 4.665 | 32.943 | 1.00 | 28.73 |
| ATOM | 1228 | O | ASN | 823 | 24.476 | 5.473 | 32.091 | 1.00 | 29.00 |
| ATOM | 1229 | N | GLN | 824 | 24.127 | 3.562 | 33.199 | 1.00 | 27.99 |
| ATOM | 1230 | CA | GLN | 824 | 22.893 | 3.227 | 32.514 | 1.00 | 27.77 |
| ATOM | 1231 | CB | GLN | 824 | 22.590 | 1.731 | 32.738 | 1.00 | 28.13 |
| ATOM | 1232 | CG | GLN | 824 | 21.343 | 1.158 | 32.077 | 1.00 | 28.93 |
| ATOM | 1233 | CD | GLN | 824 | 21.331 | 1.302 | 30.551 | 1.00 | 30.20 |
| ATOM | 1234 | OE1 | GLN | 824 | 22.300 | 0.976 | 29.855 | 1.00 | 30.02 |
| ATOM | 1235 | NE2 | GLN | 824 | 20.211 | 1.775 | 30.028 | 1.00 | 29.72 |
| ATOM | 1236 | C | GLN | 824 | 21.723 | 4.115 | 32.960 | 1.00 | 27.61 |
| ATOM | 1237 | O | GLN | 824 | 20.747 | 4.275 | 32.226 | 1.00 | 27.58 |
| ATOM | 1238 | N | LYS | 825 | 21.833 | 4.752 | 34.122 | 1.00 | 27.13 |
| ATOM | 1239 | CA | LYS | 825 | 20.742 | 5.590 | 34.595 | 1.00 | 26.37 |
| ATOM | 1240 | CB | LYS | 825 | 20.815 | 5.802 | 36.113 | 1.00 | 28.08 |
| ATOM | 1241 | CG | LYS | 825 | 19.430 | 5.823 | 36.792 | 1.00 | 31.02 |
| ATOM | 1242 | CD | LYS | 825 | 19.493 | 5.693 | 38.335 | 1.00 | 33.41 |
| ATOM | 1243 | CE | LYS | 825 | 18.086 | 5.725 | 39.002 | 1.00 | 34.57 |
| ATOM | 1244 | NZ | LYS | 825 | 17.196 | 4.516 | 38.739 | 1.00 | 35.55 |
| ATOM | 1245 | C | LYS | 825 | 20.679 | 6.917 | 33.876 | 1.00 | 24.74 |
| ATOM | 1246 | O | LYS | 825 | 19.625 | 7.518 | 33.799 | 1.00 | 25.30 |
| ATOM | 1247 | N | PHE | 826 | 21.794 | 7.375 | 33.330 | 1.00 | 24.06 |
| ATOM | 1248 | CA | PHE | 826 | 21.830 | 8.646 | 32.597 | 1.00 | 23.44 |
| ATOM | 1249 | CB | PHE | 826 | 23.247 | 9.191 | 32.573 | 1.00 | 25.61 |

TABLE A-continued

| ATOM | 1250 | CG  | PHE | 826 | 23.768 | 9.527  | 33.930 | 1.00 | 28.86 |
| ---- | ---- | --- | --- | --- | ------ | ------ | ------ | ---- | ----- |
| ATOM | 1251 | CD1 | PHE | 826 | 22.916 | 10.067 | 34.890 | 1.00 | 29.49 |
| ATOM | 1252 | CD2 | PHE | 826 | 25.091 | 9.284  | 34.268 | 1.00 | 29.08 |
| ATOM | 1253 | CE1 | PHE | 826 | 23.373 | 10.356 | 36.156 | 1.00 | 29.57 |
| ATOM | 1254 | CE2 | PHE | 826 | 25.551 | 9.571  | 35.533 | 1.00 | 29.80 |
| ATOM | 1255 | CZ  | PHE | 826 | 24.688 | 10.108 | 36.479 | 1.00 | 30.14 |
| ATOM | 1256 | C   | PHE | 826 | 21.344 | 8.463  | 31.178 | 1.00 | 21.78 |
| ATOM | 1257 | O   | PHE | 826 | 20.808 | 9.380  | 30.568 | 1.00 | 21.42 |
| ATOM | 1258 | N   | PHE | 827 | 21.581 | 7.277  | 30.636 | 1.00 | 20.42 |
| ATOM | 1259 | CA  | PHE | 827 | 21.145 | 6.937  | 29.299 | 1.00 | 18.74 |
| ATOM | 1260 | CB  | PHE | 827 | 21.814 | 5.644  | 28.857 | 1.00 | 17.62 |
| ATOM | 1261 | CG  | PHE | 827 | 21.238 | 5.083  | 27.610 | 1.00 | 16.77 |
| ATOM | 1262 | CD1 | PHE | 827 | 21.780 | 5.412  | 26.380 | 1.00 | 16.74 |
| ATOM | 1263 | CD2 | PHE | 827 | 20.123 | 4.261  | 27.656 | 1.00 | 16.46 |
| ATOM | 1264 | CE1 | PHE | 827 | 21.225 | 4.939  | 25.212 | 1.00 | 16.50 |
| ATOM | 1265 | CE2 | PHE | 827 | 19.555 | 3.782  | 26.491 | 1.00 | 17.41 |
| ATOM | 1266 | CZ  | PHE | 827 | 20.105 | 4.120  | 25.266 | 1.00 | 16.35 |
| ATOM | 1267 | C   | PHE | 827 | 19.267 | 6.778  | 29.277 | 1.00 | 19.19 |
| ATOM | 1268 | O   | PHE | 827 | 18.962 | 7.183  | 28.331 | 1.00 | 18.79 |
| ATOM | 1269 | N   | ASP | 828 | 19.079 | 6.150  | 30.312 | 1.00 | 20.42 |
| ATOM | 1270 | CA  | ASP | 828 | 17.638 | 5.943  | 30.421 | 1.00 | 21.69 |
| ATOM | 1271 | CB  | ASP | 828 | 17.325 | 5.045  | 31.633 | 1.00 | 23.37 |
| ATOM | 1272 | CG  | ASP | 828 | 17.885 | 3.627  | 31.487 | 1.00 | 24.46 |
| ATOM | 1273 | OD1 | ASP | 828 | 17.900 | 3.095  | 30.365 | 1.00 | 26.34 |
| ATOM | 1274 | OD2 | ASP | 828 | 18.296 | 3.023  | 32.501 | 1.00 | 26.77 |
| ATOM | 1275 | C   | ASP | 828 | 16.931 | 7.287  | 30.572 | 1.00 | 21.41 |
| ATOM | 1276 | O   | ASP | 828 | 15.835 | 7.487  | 30.070 | 1.00 | 21.87 |
| ATOM | 1277 | N   | GLU | 829 | 17.552 | 8.187  | 31.313 | 1.00 | 22.11 |
| ATOM | 1278 | CA  | GLU | 829 | 17.005 | 9.510  | 31.533 | 1.00 | 23.92 |
| ATOM | 1279 | CB  | GLU | 829 | 17.910 | 10.309 | 32.499 | 1.00 | 27.77 |
| ATOM | 1280 | CG  | GLU | 829 | 18.168 | 11.823 | 32.130 | 1.00 | 32.20 |
| ATOM | 1281 | CD  | GLU | 829 | 19.650 | 12.266 | 32.334 | 1.00 | 35.29 |
| ATOM | 1282 | OE1 | GLU | 829 | 20.005 | 12.655 | 33.482 | 1.00 | 37.06 |
| ATOM | 1283 | OE2 | GLU | 829 | 20.463 | 12.217 | 31.360 | 1.00 | 34.89 |
| ATOM | 1284 | C   | GLU | 829 | 17.011 | 10.166 | 30.174 | 1.00 | 22.78 |
| ATOM | 1285 | O   | GLU | 829 | 15.963 | 10.539 | 29.656 | 1.00 | 22.06 |
| ATOM | 1286 | N   | LEU | 830 | 18.201 | 10.200 | 29.575 | 1.00 | 22.21 |
| ATOM | 1287 | CA  | LEU | 830 | 18.437 | 10.812 | 28.272 | 1.00 | 22.14 |
| ATOM | 1288 | CB  | LEU | 830 | 19.885 | 10.575 | 27.852 | 1.00 | 21.24 |
| ATOM | 1289 | CG  | LEU | 830 | 20.415 | 11.572 | 26.833 | 1.00 | 21.76 |
| ATOM | 1290 | CD1 | LEU | 830 | 20.037 | 13.004 | 27.215 | 1.00 | 21.40 |
| ATOM | 1291 | CD2 | LEU | 830 | 21.895 | 11.429 | 26.752 | 1.00 | 22.34 |
| ATOM | 1292 | C   | LEU | 830 | 17.499 | 10.318 | 27.191 | 1.00 | 22.74 |
| ATOM | 1293 | O   | LEU | 830 | 16.874 | 11.114 | 26.481 | 1.00 | 23.35 |
| ATOM | 1294 | N   | ARG | 831 | 17.400 | 9.002  | 27.079 | 1.00 | 22.23 |
| ATOM | 1295 | CA  | ARG | 831 | 16.559 | 8.352  | 26.097 | 1.00 | 22.37 |
| ATOM | 1296 | CB  | ARG | 831 | 16.780 | 6.849  | 26.186 | 1.00 | 22.50 |
| ATOM | 1297 | CG  | ARG | 831 | 15.957 | 6.087  | 25.219 | 1.00 | 22.59 |
| ATOM | 1298 | CD  | ARG | 831 | 16.130 | 4.600  | 25.375 | 1.00 | 23.29 |
| ATOM | 1299 | NE  | ARG | 831 | 15.921 | 3.972  | 24.074 | 1.00 | 25.50 |
| ATOM | 1300 | CZ  | ARG | 831 | 14.738 | 3.800  | 23.491 | 1.00 | 24.36 |
| ATOM | 1301 | NH1 | ARG | 831 | 13.632 | 4.173  | 24.096 | 1.00 | 25.37 |
| ATOM | 1302 | NH2 | ARG | 831 | 14.676 | 3.366  | 22.250 | 1.00 | 24.31 |
| ATOM | 1303 | C   | ARG | 831 | 15.086 | 8.667  | 26.302 | 1.00 | 22.46 |
| ATOM | 1304 | O   | ARG | 831 | 14.354 | 8.964  | 25.351 | 1.00 | 22.89 |
| ATOM | 1305 | N   | MET | 832 | 14.655 | 8.593  | 27.550 | 1.00 | 22.76 |
| ATOM | 1306 | CA  | MET | 832 | 13.276 | 8.859  | 27.923 | 1.00 | 22.91 |
| ATOM | 1307 | CB  | MET | 832 | 13.126 | 8.762  | 29.429 | 1.00 | 23.88 |
| ATOM | 1308 | CG  | MET | 832 | 11.739 | 9.050  | 29.870 | 1.00 | 24.65 |
| ATOM | 1309 | SD  | MET | 832 | 11.693 | 9.332  | 31.596 | 1.00 | 29.43 |
| ATOM | 1310 | CE  | MET | 832 | 10.059 | 10.026 | 31.651 | 1.00 | 29.67 |
| ATOM | 1311 | C   | MET | 832 | 12.879 | 10.262 | 27.513 | 1.00 | 23.47 |
| ATOM | 1312 | O   | MET | 832 | 11.740 | 10.512 | 27.097 | 1.00 | 23.79 |
| ATOM | 1313 | N   | ASN | 833 | 13.782 | 11.198 | 27.768 | 1.00 | 23.63 |
| ATOM | 1314 | CA  | ASN | 833 | 13.562 | 12.599 | 27.423 | 1.00 | 23.80 |
| ATOM | 1315 | CB  | ASN | 833 | 14.676 | 13.482 | 28.013 | 1.00 | 23.64 |
| ATOM | 1316 | CG  | ASN | 833 | 14.532 | 13.679 | 29.544 | 1.00 | 23.87 |
| ATOM | 1317 | OD1 | ASN | 833 | 15.519 | 13.864 | 30.270 | 1.00 | 23.24 |
| ATOM | 1318 | ND2 | ASN | 833 | 13.293 | 13.628 | 30.030 | 1.00 | 24.57 |
| ATOM | 1319 | C   | ASN | 833 | 13.403 | 12.761 | 25.905 | 1.00 | 23.94 |
| ATOM | 1320 | O   | ASN | 833 | 12.463 | 13.397 | 25.445 | 1.00 | 24.48 |
| ATOM | 1321 | N   | TYR | 834 | 14.240 | 12.093 | 15.123 | 1.00 | 23.69 |
| ATOM | 1322 | CA  | TYR | 834 | 14.121 | 12.165 | 23.673 | 1.00 | 24.70 |
| ATOM | 1323 | CB  | TYR | 834 | 15.340 | 11.532 | 23.007 | 1.00 | 25.39 |
| ATOM | 1324 | CG  | TYR | 834 | 16.491 | 12.489 | 22.872 | 1.00 | 25.49 |
| ATOM | 1325 | CD1 | TYR | 834 | 16.802 | 13.051 | 21.635 | 1.00 | 26.75 |
| ATOM | 1326 | CE1 | TYR | 834 | 17.828 | 13.975 | 21.502 | 1.00 | 27.67 |
| ATOM | 1327 | CD2 | TYR | 834 | 17.239 | 12.869 | 23.986 | 1.00 | 26.00 |
| ATOM | 1328 | CE2 | TYR | 834 | 18.268 | 13.791 | 23.873 | 1.00 | 26.69 |

TABLE A-continued

| | | | | | | | | |
|---|---|---|---|---|---|---|---|---|
| ATOM | 1329 | CZ | TYR | 834 | 18.558 | 14.341 | 22.624 | 1.00 | 28.15 |
| ATOM | 1330 | OH | TYR | 834 | 19.571 | 15.263 | 22.497 | 1.00 | 28.86 |
| ATOM | 1331 | C | TYR | 834 | 12.809 | 11.574 | 23.128 | 1.00 | 24.43 |
| ATOM | 1332 | O | TYR | 834 | 12.297 | 12.006 | 22.082 | 1.00 | 24.26 |
| ATOM | 1333 | N | ILE | 835 | 12.260 | 10.599 | 23.843 | 1.00 | 24.33 |
| ATOM | 1334 | CA | ILE | 835 | 11.004 | 9.991 | 23.450 | 1.00 | 23.48 |
| ATOM | 1335 | CB | ILE | 835 | 10.724 | 8.727 | 24.235 | 1.00 | 21.33 |
| ATOM | 1336 | CG2 | ILE | 835 | 9.297 | 8.308 | 24.054 | 1.00 | 19.87 |
| ATOM | 1337 | CG1 | ILE | 835 | 11.657 | 7.624 | 23.756 | 1.00 | 20.40 |
| ATOM | 1338 | CD1 | ILE | 835 | 11.684 | 6.400 | 24.655 | 1.00 | 21.05 |
| ATOM | 1339 | C | ILE | 835 | 9.893 | 10.977 | 23.687 | 1.00 | 25.05 |
| ATOM | 1340 | O | ILE | 835 | 8.972 | 11.061 | 22.889 | 1.00 | 26.24 |
| ATOM | 1341 | N | LYS | 836 | 9.998 | 11.738 | 24.771 | 1.00 | 26.82 |
| ATOM | 1342 | CA | LYS | 836 | 9.006 | 12.747 | 25.137 | 1.00 | 28.28 |
| ATOM | 1343 | CB | LYS | 836 | 9.245 | 13.281 | 26.556 | 1.00 | 29.95 |
| ATOM | 1344 | CG | LYS | 836 | 9.115 | 12.252 | 27.712 | 1.00 | 32.62 |
| ATOM | 1345 | CD | LYS | 836 | 7.690 | 11.672 | 27.901 | 1.00 | 33.04 |
| ATOM | 1346 | CE | LYS | 836 | 7.575 | 10.238 | 27.344 | 1.00 | 34.32 |
| ATOM | 1347 | NZ | LYS | 836 | 8.559 | 9.259 | 27.942 | 1.00 | 32.90 |
| ATOM | 1348 | C | LYS | 836 | 9.030 | 13.919 | 24.164 | 1.00 | 28.39 |
| ATOM | 1349 | O | LYS | 836 | 7.997 | 14.545 | 23.946 | 1.00 | 29.09 |
| ATOM | 1350 | N | GLU | 837 | 10.194 | 14.249 | 23.606 | 1.00 | 28.61 |
| ATOM | 1351 | CA | GLU | 837 | 10.276 | 15.351 | 22.643 | 1.00 | 28.70 |
| ATOM | 1352 | CB | GLU | 837 | 11.715 | 15.824 | 22.439 | 1.00 | 29.34 |
| ATOM | 1353 | CG | GLU | 837 | 12.305 | 16.584 | 23.627 | 1.00 | 32.13 |
| ATOM | 1354 | CD | GLU | 837 | 11.553 | 17.887 | 23.971 | 1.00 | 34.30 |
| ATOM | 1355 | OE1 | GLU | 837 | 11.612 | 18.303 | 25.157 | 1.00 | 34.18 |
| ATOM | 1356 | OE2 | GLU | 837 | 10.925 | 18.503 | 23.063 | 1.00 | 35.58 |
| ATOM | 1357 | C | GLU | 837 | 9.666 | 14.907 | 21.321 | 1.00 | 28.92 |
| ATOM | 1358 | O | GLU | 837 | 9.041 | 15.699 | 20.626 | 1.00 | 28.40 |
| ATOM | 1359 | N | LEU | 838 | 9.826 | 13.631 | 20.991 | 1.00 | 29.32 |
| ATOM | 1360 | CA | LEU | 838 | 9.250 | 13.092 | 19.774 | 1.00 | 30.90 |
| ATOM | 1361 | CB | LEU | 838 | 9.614 | 11.622 | 19.592 | 1.00 | 30.44 |
| ATOM | 1362 | CG | LEU | 838 | 8.810 | 10.983 | 18.460 | 1.00 | 30.56 |
| ATOM | 1363 | CD1 | LEU | 838 | 9.077 | 11.728 | 17.151 | 1.00 | 30.31 |
| ATOM | 1364 | CD2 | LEU | 838 | 9.166 | 9.533 | 18.330 | 1.00 | 30.00 |
| ATOM | 1365 | C | LEU | 838 | 7.740 | 13.211 | 19.884 | 1.00 | 32.66 |
| ATOM | 1366 | O | LEU | 838 | 7.076 | 13.706 | 18.983 | 1.00 | 32.60 |
| ATOM | 1367 | N | ASP | 839 | 7.186 | 12.724 | 20.979 | 1.00 | 34.82 |
| ATOM | 1368 | CA | ASP | 839 | 5.755 | 12.823 | 21.162 | 1.00 | 37.61 |
| ATOM | 1369 | CA | ASP | 839 | 5.331 | 12.117 | 22.449 | 1.00 | 39.22 |
| ATOM | 1370 | CG | ASP | 839 | 3.816 | 11.952 | 22.557 | 1.00 | 41.54 |
| ATOM | 1371 | OD1 | ASP | 839 | 3.249 | 12.375 | 23.592 | 1.00 | 43.10 |
| ATOM | 1372 | OD2 | ASP | 839 | 3.192 | 11.400 | 21.613 | 1.00 | 42.60 |
| ATOM | 1373 | C | ASP | 839 | 5.338 | 14.293 | 21.187 | 1.00 | 38.83 |
| ATOM | 1374 | O | ASP | 839 | 4.285 | 14.645 | 20.672 | 1.00 | 39.02 |
| ATOM | 1375 | N | ARG | 840 | 6.195 | 15.151 | 21.731 | 1.00 | 40.51 |
| ATOM | 1376 | CA | ARG | 840 | 5.916 | 16.580 | 21.828 | 1.00 | 42.20 |
| ATOM | 1377 | CB | ARG | 840 | 7.032 | 17.289 | 22.610 | 1.00 | 43.32 |
| ATOM | 1378 | CG | ARG | 840 | 6.657 | 18.639 | 23.261 | 1.00 | 45.47 |
| ATOM | 1379 | CD | ARG | 840 | 6.945 | 19.881 | 22.401 | 1.00 | 46.95 |
| ATOM | 1380 | NE | ARG | 840 | 8.319 | 20.371 | 22.542 | 1.00 | 48.57 |
| ATOM | 1381 | CZ | ARG | 840 | 9.066 | 20.823 | 21.533 | 1.00 | 49.57 |
| ATOM | 1382 | NH1 | ARG | 840 | 8.580 | 20.860 | 20.294 | 1.00 | 49.89 |
| ATOM | 1383 | NH2 | ARG | 840 | 10.314 | 21.220 | 21.755 | 1.00 | 49.90 |
| ATOM | 1384 | C | ARG | 840 | 5.776 | 17.220 | 20.457 | 1.00 | 43.27 |
| ATOM | 1385 | O | ARG | 840 | 4.860 | 18.004 | 20.232 | 1.00 | 43.50 |
| ATOM | 1386 | N | ILE | 841 | 6.663 | 16.876 | 19.528 | 1.00 | 44.53 |
| ATOM | 1387 | CA | ILE | 841 | 6.600 | 17.483 | 18.211 | 1.00 | 46.22 |
| ATOM | 1388 | CB | ILE | 841 | 7.983 | 17.572 | 17.510 | 1.00 | 45.82 |
| ATOM | 1389 | CG2 | ILE | 841 | 9.044 | 18.078 | 18.463 | 1.00 | 46.40 |
| ATOM | 1390 | CG1 | ILE | 841 | 8.383 | 16.237 | 16.918 | 1.00 | 46.46 |
| ATOM | 1391 | CD1 | ILE | 841 | 8.064 | 16.150 | 15.463 | 1.00 | 45.92 |
| ATOM | 1392 | C | ILE | 841 | 5.534 | 16.913 | 17.286 | 1.00 | 48.04 |
| ATOM | 1393 | O | ILE | 841 | 5.472 | 17.572 | 16.109 | 1.00 | 48.90 |
| ATOM | 1394 | N | ILE | 842 | 4.737 | 15.976 | 17.786 | 1.00 | 49.91 |
| ATOM | 1395 | CA | ILE | 842 | 3.632 | 15.446 | 16.990 | 1.00 | 51.38 |
| ATOM | 1396 | CB | ILE | 842 | 3.577 | 13.878 | 16.889 | 1.00 | 51.11 |
| ATOM | 1397 | CG2 | ILE | 842 | 3.917 | 13.445 | 15.482 | 1.00 | 51.75 |
| ATOM | 1398 | CG1 | ILE | 842 | 4.523 | 13.192 | 17.870 | 1.00 | 50.67 |
| ATOM | 1399 | CD1 | ILE | 842 | 4.691 | 11.701 | 17.619 | 1.00 | 49.36 |
| ATOM | 1400 | C | ILE | 842 | 2.384 | 16.003 | 17.659 | 1.00 | 52.63 |
| ATOM | 1401 | O | ILE | 842 | 1.509 | 16.551 | 16.999 | 1.00 | 52.38 |
| ATOM | 1402 | N | ALA | 843 | 2.356 | 15.939 | 18.986 | 1.00 | 54.81 |
| ATOM | 1403 | CA | ALA | 843 | 1.242 | 16.456 | 19.761 | 1.00 | 57.24 |
| ATOM | 1404 | CB | ALA | 843 | 1.424 | 16.129 | 21.247 | 1.00 | 56.69 |
| ATOM | 1405 | C | ALA | 843 | 1.215 | 17.962 | 19.557 | 1.00 | 59.28 |
| ATOM | 1406 | O | ALA | 843 | 1.847 | 18.704 | 20.304 | 1.00 | 59.69 |
| ATOM | 1407 | N | CYS | 844 | 0.560 | 18.391 | 18.481 | 1.00 | 61.60 |

TABLE A-continued

| | | | | | | | | |
|---|---|---|---|---|---|---|---|---|
| ATOM | 1408 | CA | CYS | 844 | 0.402 | 19.810 | 18.130 | 1.00 | 63.67 |
| ATOM | 1409 | CB | CYS | 844 | 1.766 | 20.536 | 17.979 | 1.00 | 64.05 |
| ATOM | 1410 | SG | CYS | 844 | 2.751 | 20.268 | 16.470 | 1.00 | 65.30 |
| ATOM | 1411 | C | CYS | 844 | −0.441 | 19.854 | 16.848 | 1.00 | 64.63 |
| ATOM | 1412 | O | CYS | 844 | −1.618 | 19.471 | 16.889 | 1.00 | 64.70 |
| ATOM | 1413 | N | ALA | 845 | 0.136 | 20.332 | 15.738 | 1.00 | 65.65 |
| ATOM | 1414 | CA | ALA | 845 | −0.545 | 20.374 | 14.439 | 1.00 | 65.96 |
| ATOM | 1415 | CB | ALA | 845 | −0.195 | 21.639 | 13.684 | 1.00 | 65.80 |
| ATOM | 1416 | C | ALA | 845 | −0.079 | 19.165 | 13.644 | 1.00 | 66.49 |
| ATOM | 1417 | O | ALA | 845 | −0.675 | 18.829 | 12.620 | 1.00 | 66.85 |
| ATOM | 1418 | N | ALA | 846 | 0.998 | 18.553 | 14.127 | 1.00 | 66.74 |
| ATOM | 1419 | CA | ALA | 846 | 1.601 | 17.343 | 13.511 | 1.00 | 66.90 |
| ATOM | 1420 | CB | ALA | 846 | 3.110 | 17.337 | 13.730 | 1.00 | 66.74 |
| ATOM | 1421 | C | ALA | 846 | 0.984 | 16.074 | 14.086 | 1.00 | 66.88 |
| ATOM | 1422 | O | ALA | 846 | 1.675 | 15.092 | 14.345 | 1.00 | 66.35 |
| ATOM | 1423 | N | ALA | 847 | −0.325 | 16.141 | 14.291 | 1.00 | 67.27 |
| ATOM | 1424 | CA | ALA | 847 | −1.162 | 15.076 | 14.826 | 1.00 | 67.87 |
| ATOM | 1425 | CB | ALA | 847 | −0.515 | 14.407 | 16.033 | 1.00 | 68.14 |
| ATOM | 1426 | C | ALA | 847 | −2.420 | 15.816 | 15.251 | 1.00 | 68.35 |
| ATOM | 1427 | O | ALA | 847 | −2.432 | 17.046 | 15.278 | 1.00 | 68.33 |
| ATOM | 1428 | N | ALA | 848 | −3.468 | 15.079 | 15.597 | 1.00 | 69.11 |
| ATOM | 1429 | CA | ALA | 848 | −4.728 | 15.685 | 16.016 | 1.00 | 69.71 |
| ATOM | 1430 | CB | ALA | 848 | −5.272 | 16.598 | 14.907 | 1.00 | 69.68 |
| ATOM | 1431 | C | ALA | 848 | −5.737 | 14.586 | 16.340 | 1.00 | 70.20 |
| ATOM | 1432 | O | ALA | 848 | −5.342 | 13.474 | 16.720 | 1.00 | 70.21 |
| ATOM | 1433 | N | ALA | 849 | −7.021 | 14.914 | 16.146 | 1.00 | 70.54 |
| ATOM | 1434 | CA | ALA | 849 | −8.185 | 14.043 | 16.374 | 1.00 | 70.31 |
| ATOM | 1435 | CB | ALA | 849 | −9.014 | 13.929 | 15.079 | 1.00 | 70.65 |
| ATOM | 1436 | C | ALA | 849 | −7.856 | 12.661 | 16.920 | 1.00 | 69.92 |
| ATOM | 1437 | O | ALA | 849 | −7.665 | 12.492 | 18.130 | 1.00 | 70.12 |
| ATOM | 1438 | N | ALA | 850 | −7.808 | 11.680 | 16.020 | 1.00 | 69.47 |
| ATOM | 1439 | CA | ALA | 850 | −7.473 | 10.304 | 16.377 | 1.00 | 68.74 |
| ATOM | 1440 | CB | ALA | 850 | −8.494 | 9.331 | 15.774 | 1.00 | 68.95 |
| ATOM | 1441 | C | ALA | 850 | −6.061 | 10.015 | 15.845 | 1.00 | 67.76 |
| ATOM | 1442 | O | ALA | 850 | −5.590 | 8.867 | 15.684 | 1.00 | 67.27 |
| ATOM | 1443 | N | SER | 851 | −5.391 | 11.077 | 15.388 | 1.00 | 66.46 |
| ATOM | 1444 | CA | SER | 851 | −4.046 | 10.962 | 14.846 | 1.00 | 65.28 |
| ATOM | 1445 | CB | SER | 851 | −3.664 | 12.200 | 14.018 | 1.00 | 65.24 |
| ATOM | 1446 | OG | SER | 851 | −2.405 | 12.037 | 13.369 | 1.00 | 65.05 |
| ATOM | 1447 | C | SER | 851 | −3.023 | 10.710 | 15.944 | 1.00 | 64.16 |
| ATOM | 1448 | O | SER | 851 | −2.426 | 9.639 | 15.969 | 1.00 | 64.16 |
| ATOM | 1449 | N | CYS | 852 | −2.873 | 11.651 | 16.879 | 1.00 | 62.68 |
| ATOM | 1450 | CA | CYS | 852 | −1.901 | 11.526 | 17.974 | 1.00 | 60.96 |
| ATOM | 1451 | CB | CYS | 852 | −2.353 | 12.333 | 19.191 | 1.00 | 61.34 |
| ATOM | 1452 | SG | CYS | 852 | −1.712 | 14.024 | 19.216 | 1.00 | 62.06 |
| ATOM | 1453 | C | CYS | 852 | −1.480 | 10.102 | 18.388 | 1.00 | 59.71 |
| ATOM | 1454 | O | CYS | 852 | −0.282 | 9.800 | 18.422 | 1.00 | 59.67 |
| ATOM | 1455 | N | SER | 853 | −2.440 | 9.223 | 18.678 | 1.00 | 57.85 |
| ATOM | 1456 | CA | SER | 853 | −2.109 | 7.847 | 19.053 | 1.00 | 55.45 |
| ATOM | 1457 | CB | SER | 853 | −3.308 | 7.133 | 19.686 | 1.00 | 56.27 |
| ATOM | 1458 | OG | SER | 853 | −3.480 | 7.522 | 21.038 | 1.00 | 57.65 |
| ATOM | 1459 | C | SER | 853 | −1.610 | 7.052 | 17.847 | 1.00 | 53.09 |
| ATOM | 1460 | O | SER | 853 | −0.601 | 6.346 | 17.942 | 1.00 | 53.22 |
| ATOM | 1461 | N | ARG | 854 | −2.304 | 7.172 | 16.719 | 1.00 | 49.75 |
| ATOM | 1462 | CA | ARG | 854 | −1.924 | 6.462 | 15.500 | 1.00 | 46.39 |
| ATOM | 1463 | CB | ARG | 854 | −3.021 | 6.634 | 14.443 | 1.00 | 47.23 |
| ATOM | 1464 | CG | ARG | 854 | −2.747 | 5.970 | 13.105 | 1.00 | 48.09 |
| ATOM | 1465 | CD | ARG | 854 | −2.985 | 6.943 | 11.940 | 1.00 | 49.85 |
| ATOM | 1466 | NE | ARG | 854 | −4.340 | 7.500 | 11.936 | 1.00 | 51.11 |
| ATOM | 1467 | CZ | ARG | 854 | −4.911 | 8.122 | 10.904 | 1.00 | 51.20 |
| ATOM | 1468 | NH1 | ARG | 854 | −4.261 | 8.290 | 9.755 | 1.00 | 51.32 |
| ATOM | 1469 | NH2 | ARG | 854 | −6.153 | 8.567 | 11.021 | 1.00 | 51.21 |
| ATOM | 1470 | C | ARG | 854 | −0.564 | 6.962 | 14.967 | 1.00 | 43.72 |
| ATOM | 1471 | O | ARG | 854 | 0.294 | 6.164 | 14.564 | 1.00 | 43.80 |
| ATOM | 1472 | N | ARG | 855 | −0.360 | 8.273 | 15.019 | 1.00 | 39.68 |
| ATOM | 1473 | CA | ARG | 855 | 0.860 | 8.926 | 14.558 | 1.00 | 36.58 |
| ATOM | 1474 | CB | ARG | 855 | 0.713 | 10.439 | 14.734 | 1.00 | 36.42 |
| ATOM | 1475 | CG | ARG | 855 | 1.801 | 11.264 | 14.082 | 1.00 | 34.79 |
| ATOM | 1476 | CD | ARG | 855 | 1.724 | 11.109 | 12.594 | 1.00 | 32.86 |
| ATOM | 1477 | NE | ARG | 855 | 2.869 | 11.699 | 11.907 | 1.00 | 30.54 |
| ATOM | 1478 | CZ | ARG | 855 | 3.030 | 11.655 | 10.590 | 1.00 | 29.61 |
| ATOM | 1479 | NH1 | ARG | 855 | 2.130 | 11.051 | 9.831 | 1.00 | 28.88 |
| ATOM | 1480 | NH2 | ARG | 855 | 4.085 | 12.219 | 10.028 | 1.00 | 29.20 |
| ATOM | 1481 | C | ARG | 855 | 2.106 | 8.454 | 15.306 | 1.00 | 35.02 |
| ATOM | 1482 | O | ARG | 855 | 3.180 | 8.326 | 14.723 | 1.00 | 34.97 |
| ATOM | 1483 | N | PHE | 856 | 1.973 | 8.239 | 16.609 | 1.00 | 33.30 |
| ATOM | 1484 | CA | PHE | 856 | 3.086 | 7.786 | 17.428 | 1.00 | 31.21 |
| ATOM | 1485 | CB | PHE | 856 | 2.846 | 8.128 | 18.895 | 1.00 | 30.24 |
| ATOM | 1486 | CG | PHE | 856 | 4.058 | 7.977 | 19.755 | 1.00 | 30.06 |

TABLE A-continued

| | | | | | | | | |
|---|---|---|---|---|---|---|---|---|
| ATOM | 1487 | CD1 | PHE | 856 | 5.022 | 8.972 | 19.787 | 1.00 | 29.34 |
| ATOM | 1488 | CD2 | PHE | 856 | 4.241 | 6.829 | 20.536 | 1.00 | 29.33 |
| ATOM | 1489 | CE1 | PHE | 856 | 6.150 | 8.832 | 20.580 | 1.00 | 29.36 |
| ATOM | 1490 | CE2 | PHE | 856 | 5.364 | 6.676 | 21.335 | 1.00 | 28.86 |
| ATOM | 1491 | CZ | PHE | 856 | 6.325 | 7.680 | 21.357 | 1.00 | 29.62 |
| ATOM | 1492 | C | PHE | 856 | 3.308 | 6.290 | 17.254 | 1.00 | 30.61 |
| ATOM | 1493 | O | PHE | 856 | 4.420 | 5.803 | 17.424 | 1.00 | 30.75 |
| ATOM | 1494 | N | TYR | 857 | 2.258 | 5.543 | 16.943 | 1.00 | 29.79 |
| ATOM | 1495 | CA | TYR | 857 | 2.446 | 4.118 | 16.725 | 1.00 | 29.79 |
| ATOM | 1496 | CB | TYR | 857 | 1.116 | 3.365 | 16.660 | 1.00 | 30.78 |
| ATOM | 1497 | CG | TYR | 857 | 1.254 | 1.871 | 16.396 | 1.00 | 32.21 |
| ATOM | 1498 | CD1 | TYR | 857 | 1.425 | 0.972 | 17.442 | 1.00 | 32.75 |
| ATOM | 1499 | CE1 | TYR | 857 | 1.548 | −0.401 | 17.215 | 1.00 | 34.60 |
| ATOM | 1500 | CD2 | TYR | 857 | 1.208 | 1.362 | 15.098 | 1.00 | 33.36 |
| ATOM | 1501 | CE2 | TYR | 857 | 1.331 | −0.011 | 14.854 | 1.00 | 34.67 |
| ATOM | 1502 | CZ | TYR | 857 | 1.503 | −0.887 | 15.918 | 1.00 | 35.61 |
| ATOM | 1503 | OH | TYR | 857 | 1.652 | −2.444 | 15.697 | 1.00 | 36.96 |
| ATOM | 1504 | C | TYR | 857 | 3.206 | 3.929 | 15.419 | 1.00 | 29.44 |
| ATOM | 1505 | O | TYR | 857 | 4.135 | 3.125 | 15.371 | 1.00 | 29.44 |
| ATOM | 1506 | N | GLN | 858 | 2.847 | 4.685 | 14.376 | 1.00 | 28.32 |
| ATOM | 1507 | CA | GLN | 858 | 3.533 | 4.537 | 13.087 | 1.00 | 28.06 |
| ATOM | 1508 | CB | GLN | 858 | 2.675 | 5.020 | 11.890 | 1.00 | 28.98 |
| ATOM | 1509 | CG | GLN | 858 | 1.970 | 6.384 | 12.029 | 1.00 | 31.65 |
| ATOM | 1510 | CD | GLN | 858 | 0.781 | 6.569 | 11.059 | 1.00 | 32.26 |
| ATOM | 1511 | OE1 | GLN | 858 | 0.385 | 7.700 | 10.724 | 1.00 | 32.11 |
| ATOM | 1512 | NE2 | GLN | 858 | 0.210 | 5.458 | 10.617 | 1.00 | 32.79 |
| ATOM | 1513 | C | GLN | 858 | 4.967 | 5.077 | 13.037 | 1.00 | 26.56 |
| ATOM | 1514 | O | GLN | 858 | 5.820 | 4.525 | 12.332 | 1.00 | 26.58 |
| ATOM | 1515 | N | LEU | 859 | 5.266 | 6.101 | 13.825 | 1.00 | 24.64 |
| ATOM | 1516 | CA | LEU | 859 | 6.622 | 6.632 | 13.832 | 1.00 | 22.82 |
| ATOM | 1517 | CB | LEU | 859 | 6.675 | 8.067 | 14.395 | 1.00 | 23.93 |
| ATOM | 1518 | CG | LEU | 859 | 6.054 | 9.243 | 13.617 | 1.00 | 23.18 |
| ATOM | 1519 | CD1 | LEU | 859 | 6.616 | 10.541 | 14.156 | 1.00 | 23.42 |
| ATON | 1520 | CD2 | LEU | 859 | 6.363 | 9.137 | 12.173 | 1.00 | 22.30 |
| ATOM | 1521 | C | LEU | 859 | 7.545 | 5.705 | 14.613 | 1.00 | 20.92 |
| ATON | 1522 | O | LEU | 859 | 8.694 | 5.486 | 14.222 | 1.00 | 20.35 |
| ATOM | 1523 | N | THR | 860 | 7.030 | 5.124 | 15.691 | 1.00 | 20.30 |
| ATOM | 1524 | CA | THR | 860 | 7.821 | 4.195 | 16.505 | 1.00 | 20.14 |
| ATOM | 1525 | CB | THR | 860 | 7.215 | 3.957 | 17.905 | 1.00 | 18.65 |
| ATOM | 1526 | OG1 | THR | 860 | 5.849 | 3.551 | 17.797 | 1.00 | 18.55 |
| ATOM | 1527 | CG2 | THR | 860 | 7.314 | 5.196 | 18.734 | 1.00 | 18.12 |
| ATOM | 1528 | C | THR | 860 | 7.969 | 2.855 | 15.765 | 1.00 | 20.30 |
| ATOM | 1529 | O | THR | 860 | 8.922 | 2.108 | 15.985 | 1.00 | 20.28 |
| ATOM | 1530 | N | LYS | 861 | 7.040 | 2.600 | 14.851 | 1.00 | 21.02 |
| ATOM | 1531 | CA | LYS | 861 | 7.046 | 1.411 | 14.034 | 1.00 | 21.82 |
| ATOM | 1532 | CB | LYS | 861 | 5.649 | 1.178 | 13.475 | 1.00 | 23.82 |
| ATOM | 1533 | CG | LYS | 861 | 5.375 | −0.268 | 13.110 | 1.00 | 26.71 |
| ATOM | 1534 | CD | LYS | 861 | 5.015 | −1.106 | 14.321 | 1.00 | 28.40 |
| ATOM | 1535 | CE | LYS | 861 | 4.924 | −2.587 | 13.922 | 1.00 | 30.14 |
| ATOM | 1536 | NZ | LYS | 861 | 4.542 | −3.514 | 15.050 | 1.00 | 31.53 |
| ATOM | 1537 | C | LYS | 861 | 8.040 | 1.642 | 12.895 | 1.00 | 21.28 |
| ATOM | 1538 | O | LYS | 861 | 8.781 | 0.750 | 12.510 | 1.00 | 21.01 |
| ATOM | 1539 | N | LEU | 862 | 8.093 | 2.863 | 12.389 | 1.00 | 21.49 |
| ATOM | 1540 | CA | LEU | 862 | 9.021 | 3.192 | 11.311 | 1.00 | 21.32 |
| ATOM | 1541 | CB | LEU | 862 | 8.713 | 4.577 | 10.731 | 1.00 | 22.14 |
| ATOM | 1542 | CG | LEU | 862 | 9.816 | 5.281 | 9.921 | 1.00 | 21.98 |
| ATOM | 1543 | CD1 | LEU | 862 | 10.022 | 4.563 | 8.622 | 1.00 | 22.72 |
| ATOM | 1544 | CD2 | LEU | 862 | 9.456 | 6.726 | 9.670 | 1.00 | 22.58 |
| ATOM | 1545 | C | LEU | 862 | 10.438 | 3.181 | 11.854 | 1.00 | 21.15 |
| ATOM | 1546 | O | LEU | 862 | 11.386 | 2.884 | 11.133 | 1.00 | 22.30 |
| ATOM | 1547 | N | LEU | 863 | 10.596 | 3.602 | 13.105 | 1.00 | 20.71 |
| ATOM | 1548 | CA | LEU | 863 | 11.906 | 3.625 | 13.749 | 1.00 | 18.90 |
| ATOM | 1549 | CB | LEU | 863 | 11.827 | 4.423 | 15.040 | 1.00 | 18.78 |
| ATOM | 1550 | CG | LEU | 863 | 11.890 | 5.931 | 14.863 | 1.00 | 18.02 |
| ATOM | 1551 | CD1 | LEU | 863 | 12.103 | 6.545 | 16.230 | 1.00 | 19.67 |
| ATOM | 1552 | CD2 | LEU | 863 | 13.049 | 6.291 | 13.944 | 1.00 | 16.59 |
| ATOM | 1553 | C | LEU | 863 | 12.462 | 2.218 | 14.004 | 1.00 | 18.08 |
| ATOM | 1554 | O | LEU | 863 | 13.676 | 1.984 | 13.895 | 1.00 | 17.06 |
| ATOM | 1555 | N | ASP | 864 | 11.592 | 1.307 | 14.436 | 1.00 | 18.33 |
| ATOM | 1556 | CA | ASP | 864 | 11.985 | −0.088 | 14.642 | 1.00 | 19.28 |
| ATOM | 1557 | CB | ASP | 864 | 10.797 | −0.917 | 15.143 | 1.00 | 19.27 |
| ATOM | 1558 | CG | ASP | 864 | 10.525 | −0.727 | 16.620 | 1.00 | 19.92 |
| ATOM | 1559 | OD1 | ASP | 864 | 11.256 | 0.045 | 17.721 | 1.00 | 20.94 |
| ATOM | 1560 | OD2 | ASP | 864 | 9.577 | −1.364 | 17.116 | 1.00 | 19.39 |
| ATOM | 1561 | C | ASP | 864 | 12.467 | −0.692 | 13.321 | 1.00 | 10.06 |
| ATOM | 1562 | O | ASP | 864 | 13.377 | −1.519 | 13.298 | 1.00 | 18.82 |
| ATOM | 1563 | N | SER | 865 | 11.847 | −0.263 | 12.222 | 1.00 | 19.90 |
| ATOM | 1564 | CA | SER | 865 | 12.202 | −0.764 | 10.894 | 1.00 | 19.17 |
| ATOM | 1565 | CB | SER | 865 | 11.226 | −0.289 | 9.798 | 1.00 | 18.59 |

TABLE A-continued

| | | | | | | | | |
|---|---|---|---|---|---|---|---|---|
| ATOM | 1566 | OG | SER | 865 | 11.167 | 1.123 | 9.613 | 1.00 | 19.91 |
| ATOM | 1567 | C | SER | 865 | 13.634 | −0.507 | 10.489 | 1.00 | 18.01 |
| ATOM | 1568 | O | SER | 865 | 14.213 | −1.294 | 9.765 | 1.00 | 18.93 |
| ATOM | 1569 | N | VAL | 866 | 14.257 | 0.535 | 11.004 | 1.00 | 17.08 |
| ATOM | 1570 | CA | VAL | 866 | 15.619 | 0.747 | 10.589 | 1.00 | 15.20 |
| ATOM | 1571 | CB | VAL | 866 | 16.093 | 2.211 | 10.783 | 1.00 | 15.01 |
| ATOM | 1572 | CG1 | VAL | 866 | 14.982 | 3.081 | 11.320 | 1.00 | 13.81 |
| ATOM | 1573 | CG2 | VAL | 866 | 17.344 | 2.280 | 11.574 | 1.00 | 13.41 |
| ATOM | 1574 | C | VAL | 866 | 16.564 | −0.260 | 11.194 | 1.00 | 14.83 |
| ATOM | 1575 | O | VAL | 866 | 17.625 | −0.518 | 10.641 | 1.00 | 14.66 |
| ATOM | 1576 | N | GLN | 867 | 16.168 | −0.873 | 12.032 | 1.00 | 15.12 |
| ATOM | 1577 | CA | GLN | 867 | 17.031 | −1.849 | 12.977 | 1.00 | 15.64 |
| ATOM | 1578 | CB | GLN | 867 | 16.508 | −2.155 | 14.374 | 1.00 | 16.10 |
| ATOM | 1579 | CG | GLN | 867 | 16.526 | −0.968 | 15.315 | 1.00 | 16.35 |
| ATOM | 1580 | CD | GLN | 867 | 17.910 | −0.474 | 15.672 | 1.00 | 17.91 |
| ATOM | 1581 | OE1 | GLN | 867 | 18.924 | −1.175 | 15.510 | 1.00 | 17.76 |
| ATOM | 1582 | NE2 | GLN | 867 | 17.958 | 0.750 | 16.201 | 1.00 | 17.53 |
| ATOM | 1583 | C | GLN | 867 | 17.358 | −3.143 | 12.233 | 1.00 | 14.54 |
| ATOM | 1584 | O | GLN | 867 | 18.487 | −3.594 | 12.271 | 1.00 | 15.92 |
| ATOM | 1585 | N | PRO | 868 | 16.364 | −3.809 | 11.634 | 1.00 | 14.35 |
| ATOM | 1586 | CD | PRO | 868 | 14.914 | −3.555 | 11.696 | 1.00 | 15.17 |
| ATOM | 1587 | CA | PRO | 868 | 16.630 | −5.040 | 10.886 | 1.00 | 13.73 |
| ATOM | 1588 | CB | PRO | 868 | 15.232 | −5.465 | 10.415 | 1.00 | 14.35 |
| ATOM | 1589 | CG | PRO | 868 | 14.331 | −4.928 | 11.438 | 1.00 | 14.42 |
| ATOM | 1590 | C | PRO | 868 | 17.500 | −4.704 | 9.674 | 1.00 | 13.45 |
| ATOM | 1591 | O | PRO | 868 | 18.341 | −5.497 | 9.254 | 1.00 | 14.77 |
| ATOM | 1592 | N | ILE | 869 | 17.289 | −3.514 | 9.113 | 1.00 | 13.49 |
| ATOM | 1593 | CA | ILE | 869 | 18.043 | −3.044 | 7.790 | 1.00 | 12.06 |
| ATOM | 1594 | CB | ILE | 869 | 17.447 | −1.740 | 7.358 | 1.00 | 12.53 |
| ATOM | 1595 | CG2 | ILE | 869 | 18.272 | −1.307 | 6.175 | 1.00 | 12.44 |
| ATOM | 1596 | CG1 | ILE | 869 | 15.998 | −1.973 | 6.928 | 1.00 | 12.25 |
| ATOM | 1597 | CD1 | ILE | 869 | 15.258 | −0.746 | 6.432 | 1.00 | 11.91 |
| ATOM | 1598 | C | ILE | 869 | 19.458 | −2.818 | 8.411 | 1.00 | 11.70 |
| ATOM | 1599 | O | ILE | 869 | 20.356 | −3.302 | 7.755 | 1.00 | 13.01 |
| ATOM | 1600 | N | ALA | 870 | 19.655 | −2.254 | 9.610 | 1.00 | 12.19 |
| ATOM | 1601 | CA | ALA | 870 | 21.007 | −1.993 | 10.110 | 1.00 | 11.52 |
| ATOM | 1602 | CB | ALA | 870 | 20.971 | −1.189 | 11.375 | 1.00 | 10.62 |
| ATOM | 1603 | C | ALA | 870 | 21.758 | −3.287 | 10.350 | 1.00 | 12.90 |
| ATOM | 1604 | O | ALA | 870 | 22.955 | −3.374 | 10.074 | 1.00 | 13.99 |
| ATOM | 1605 | N | ARG | 871 | 21.082 | −4.262 | 10.962 | 1.00 | 14.67 |
| ATOM | 1606 | CA | ARG | 871 | 21.659 | −5.577 | 11.226 | 1.00 | 15.30 |
| ATOM | 1607 | CB | ARG | 871 | 20.668 | −6.465 | 11.970 | 1.00 | 16.99 |
| ATOM | 1608 | CG | ARG | 871 | 21.317 | −7.789 | 12.304 | 1.00 | 20.44 |
| ATOM | 1609 | CD | ARG | 871 | 20.552 | −8.755 | 13.190 | 1.00 | 22.19 |
| ATOM | 1610 | NE | ARG | 871 | 21.529 | −9.736 | 13.678 | 1.00 | 25.05 |
| ATOM | 1611 | CZ | ARG | 871 | 22.248 | −9.581 | 14.785 | 1.00 | 24.87 |
| ATOM | 1612 | NH1 | ARG | 871 | 22.085 | −8.513 | 15.553 | 1.00 | 26.86 |
| ATOM | 1613 | NH2 | ARG | 871 | 23.221 | −10.425 | 15.059 | 1.00 | 27.12 |
| ATOM | 1614 | C | ARG | 871 | 22.119 | −6.287 | 9.939 | 1.00 | 16.18 |
| ATOM | 1615 | O | ARG | 871 | 23.216 | −6.846 | 9.897 | 1.00 | 16.90 |
| ATOM | 1616 | N | GLU | 872 | 21.300 | −6.256 | 8.886 | 1.00 | 17.08 |
| ATOM | 1617 | CA | GLU | 872 | 21.669 | −6.874 | 7.595 | 1.00 | 17.70 |
| ATOM | 1618 | CB | GLU | 872 | 20.546 | −6.670 | 6.578 | 1.00 | 20.21 |
| ATOM | 1619 | CG | GLU | 872 | 20.070 | −7.920 | 5.827 | 1.00 | 27.32 |
| ATON | 1620 | CD | GLU | 872 | 19.041 | −7.600 | 4.715 | 1.00 | 31.24 |
| ATOM | 1621 | OE1 | GLU | 872 | 19.199 | −8.069 | 3.544 | 1.00 | 32.65 |
| ATOM | 1622 | OE2 | GLU | 872 | 18.068 | −6.867 | 5.018 | 1.00 | 33.14 |
| ATOM | 1623 | C | GLU | 872 | 22.961 | −6.229 | 7.064 | 1.00 | 16.22 |
| ATOM | 1624 | O | GLU | 872 | 23.826 | −6.892 | 6.504 | 1.00 | 16.64 |
| ATOM | 1625 | N | LEU | 873 | 23.109 | −4.927 | 7.254 | 1.00 | 15.48 |
| ATOM | 1626 | CA | LEU | 873 | 24.304 | −4.230 | 6.781 | 1.00 | 13.64 |
| ATOM | 1627 | CB | LEU | 873 | 24.040 | −2.718 | 6.664 | 1.00 | 13.09 |
| ATOM | 1628 | CG | LEU | 873 | 22.957 | −2.359 | 5.640 | 1.00 | 12.60 |
| ATOM | 1629 | CD1 | LEU | 873 | 22.396 | −0.985 | 5.856 | 1.00 | 13.12 |
| ATOM | 1630 | CD2 | LEU | 873 | 23.511 | −2.529 | 4.229 | 1.00 | 12.29 |
| ATOM | 1631 | C | LEU | 873 | 25.489 | −4.510 | 7.662 | 1.00 | 13.26 |
| ATOM | 1632 | O | LEU | 873 | 26.621 | −4.541 | 7.185 | 1.00 | 12.91 |
| ATOM | 1633 | N | HIS | 874 | 25.237 | −4.688 | 8.960 | 1.00 | 14.96 |
| ATOM | 1634 | CA | HIS | 874 | 26.297 | −5.011 | 9.935 | 1.00 | 15.73 |
| ATOM | 1635 | CB | HIS | 874 | 25.735 | −5.154 | 11.351 | 1.00 | 14.09 |
| ATOM | 1636 | CG | HIS | 874 | 25.513 | −3.860 | 12.062 | 1.00 | 13.53 |
| ATOM | 1637 | CD2 | HIS | 874 | 26.303 | −2.769 | 12.204 | 1.00 | 12.74 |
| ATOM | 1638 | ND1 | HIS | 874 | 24.365 | −3.588 | 12.771 | 1.00 | 12.74 |
| ATOM | 1639 | CE1 | HIS | 874 | 24.451 | −2.397 | 13.313 | 1.00 | 11.45 |
| ATOM | 1640 | NE2 | HIS | 874 | 25.616 | −1.878 | 12.990 | 1.00 | 10.87 |
| ATOM | 1641 | C | HIS | 874 | 26.945 | −6.342 | 9.549 | 1.00 | 16.66 |
| ATOM | 1642 | O | HIS | 874 | 28.171 | −6.454 | 9.539 | 1.00 | 16.68 |
| ATOM | 1643 | N | GLN | 875 | 26.122 | −7.356 | 9.268 | 1.00 | 18.67 |
| ATOM | 1644 | CA | GLN | 875 | 26.635 | −8.674 | 8.853 | 1.00 | 19.45 |

TABLE A-continued

| ATOM | 1645 | CB  | GLN | 875 | 25.507 | −9.726  | 8.779  | 1.00 | 21.56 |
| ATOM | 1646 | CG  | GLN | 875 | 25.566 | −10.875 | 9.864  | 1.00 | 25.76 |
| ATOM | 1647 | CD  | GLN | 875 | 26.681 | −11.938 | 9.671  | 1.00 | 26.74 |
| ATOM | 1648 | OE1 | GLN | 875 | 27.871 | −11.624 | 9.654  | 1.00 | 27.36 |
| ATOM | 1649 | NE2 | GLN | 875 | 26.285 | −13.204 | 9.589  | 1.00 | 27.93 |
| ATOM | 1650 | C   | GLN | 875 | 27.324 | −8.521  | 7.491  | 1.00 | 18.37 |
| ATOM | 1651 | O   | GLN | 875 | 28.428 | −9.022  | 7.294  | 1.00 | 18.65 |
| ATOM | 1652 | N   | PHE | 876 | 26.737 | −7.724  | 6.597  | 1.00 | 18.47 |
| ATOM | 1653 | CA  | PHE | 876 | 27.338 | −7.515  | 5.280  | 1.00 | 18.22 |
| ATOM | 1654 | CB  | PHE | 876 | 26.453 | −6.641  | 4.377  | 1.00 | 19.25 |
| ATOM | 1655 | CG  | PHE | 876 | 26.966 | −6.506  | 2.954  | 1.00 | 19.63 |
| ATOM | 1656 | CD1 | PHE | 876 | 28.038 | −5.675  | 2.657  | 1.00 | 18.97 |
| ATOM | 1657 | CD2 | PHE | 876 | 26.380 | −7.226  | 1.917  | 1.00 | 19.90 |
| ATOM | 1658 | CE1 | PHE | 876 | 28.519 | −5.558  | 1.343  | 1.00 | 20.30 |
| ATOM | 1659 | CE2 | PHE | 876 | 26.857 | −7.113  | 0.597  | 1.00 | 20.70 |
| ATOM | 1660 | CZ  | PHE | 876 | 27.926 | −6.281  | 0.310  | 1.00 | 18.82 |
| ATOM | 1661 | C   | PHE | 876 | 28.689 | −6.871  | 5.403  | 1.00 | 17.76 |
| ATOM | 1662 | O   | PHE | 876 | 29.687 | −7.412  | 4.920  | 1.00 | 17.95 |
| ATOM | 1663 | N   | THR | 877 | 28.741 | −5.732  | 6.086  | 1.00 | 17.85 |
| ATOM | 1664 | CA  | THR | 877 | 30.002 | −5.024  | 6.215  | 1.00 | 17.77 |
| ATOM | 1665 | CB  | THR | 877 | 29.855 | −3.641  | 6.915  | 1.00 | 18.24 |
| ATOM | 1666 | OG1 | THR | 877 | 30.954 | −2.808  | 6.525  | 1.00 | 19.13 |
| ATOM | 1667 | CG2 | THR | 877 | 29.868 | −3.765  | 8.444  | 1.00 | 17.92 |
| ATOM | 1668 | C   | THR | 877 | 31.040 | −5.884  | 6.900  | 1.00 | 17.52 |
| ATOM | 1669 | O   | THR | 877 | 32.208 | −5.849  | 6.514  | 1.00 | 16.51 |
| ATOM | 1670 | N   | PHE | 878 | 30.634 | −6.610  | 7.943  | 1.00 | 18.06 |
| ATOM | 1671 | CA  | PHE | 878 | 31.559 | −7.501  | 8.651  | 1.00 | 19.20 |
| ATOM | 1672 | CB  | PHE | 878 | 30.863 | −8.201  | 9.805  | 1.00 | 19.53 |
| ATOM | 1673 | CG  | PHE | 878 | 31.731 | −9.220  | 10.484 | 1.00 | 20.60 |
| ATOM | 1674 | CD1 | PHE | 878 | 32.681 | −8.829  | 11.414 | 1.00 | 19.88 |
| ATOM | 1675 | CD2 | PHE | 878 | 31.623 | −10.575 | 10.150 | 1.00 | 20.59 |
| ATOM | 1676 | CE1 | PHE | 878 | 33.518 | −9.774  | 12.008 | 1.00 | 22.10 |
| ATOM | 1677 | CE2 | PHE | 878 | 32.454 | −11.532 | 10.733 | 1.00 | 20.21 |
| ATOM | 1678 | CZ  | PHE | 878 | 33.403 | −11.138 | 11.660 | 1.00 | 20.82 |
| ATOM | 1679 | C   | PHE | 878 | 32.176 | −8.567  | 7.725  | 1.00 | 18.91 |
| ATOM | 1680 | O   | PHE | 878 | 33.400 | −8.724  | 7.670  | 1.00 | 17.63 |
| ATOM | 1681 | N   | ASP | 879 | 31.326 | −9.268  | 6.973  | 1.00 | 19.57 |
| ATOM | 1682 | CA  | ASP | 879 | 31.800 | −10.301 | 6.054  | 1.00 | 20.02 |
| ATOM | 1683 | CB  | ASP | 879 | 30.622 | −10.972 | 5.342  | 1.00 | 20.24 |
| ATOM | 1684 | CG  | ASP | 879 | 29.693 | −11.724 | 6.307  | 1.00 | 22.04 |
| ATOM | 1685 | OD1 | ASP | 879 | 30.122 | −12.072 | 7.443  | 1.00 | 23.16 |
| ATOM | 1686 | OD2 | ASP | 879 | 28.520 | −11.968 | 5.937  | 1.00 | 21.98 |
| ATOM | 1687 | C   | ASP | 879 | 32.723 | −9.654  | 5.044  | 1.00 | 20.35 |
| ATOM | 1688 | O   | ASP | 879 | 33.802 | −10.171 | 4.737  | 1.00 | 20.51 |
| ATOM | 1689 | N   | LEU | 880 | 32.342 | −8.472  | 4.580  | 1.00 | 20.77 |
| ATOM | 1690 | CA  | LEU | 880 | 33.149 | −7.775  | 3.596  | 1.00 | 20.33 |
| ATOM | 1691 | CB  | LEU | 880 | 32.484 | −6.471  | 3.180  | 1.00 | 20.23 |
| ATOM | 1692 | CG  | LEU | 880 | 33.089 | −5.838  | 1.939  | 1.00 | 18.50 |
| ATOM | 1693 | CD1 | LEU | 880 | 33.310 | −6.886  | 0.855  | 1.00 | 19.38 |
| ATOM | 1694 | CD2 | LEU | 880 | 32.159 | −4.762  | 1.477  | 1.00 | 18.07 |
| ATOM | 1695 | C   | LEU | 880 | 34.529 | −7.496  | 4.136  | 1.00 | 20.40 |
| ATOM | 1696 | O   | LEU | 880 | 35.513 | −7.723  | 3.453  | 1.00 | 21.41 |
| ATOM | 1697 | N   | LEU | 881 | 34.602 | −7.040  | 5.376  | 1.00 | 20.90 |
| ATOM | 1698 | CA  | LEU | 881 | 35.882 | −6.723  | 6.011  | 1.00 | 20.84 |
| ATOM | 1699 | CB  | LEU | 881 | 35.651 | −6.055  | 7.364  | 1.00 | 19.23 |
| ATOM | 1700 | CG  | LEU | 881 | 36.989 | −5.773  | 8.031  | 1.00 | 19.26 |
| ATOM | 1701 | CD1 | LEU | 881 | 37.662 | −4.593  | 7.350  | 1.00 | 19.67 |
| ATOM | 1702 | CD2 | LEU | 881 | 36.810 | −5.514  | 9.500  | 1.00 | 18.92 |
| ATOM | 1703 | C   | LEU | 881 | 36.818 | −7.923  | 6.188  | 1.00 | 21.55 |
| ATOM | 1704 | O   | LEU | 881 | 38.055 | −7.806  | 6.107  | 1.00 | 21.03 |
| ATOM | 1705 | N   | ILE | 882 | 36.230 | −9.063  | 6.492  | 1.00 | 22.39 |
| ATOM | 1706 | CA  | ILE | 882 | 37.013 | −10.265 | 6.671  | 1.00 | 23.63 |
| ATOM | 1707 | CB  | ILE | 882 | 36.136 | −11.390 | 7.248  | 1.00 | 23.00 |
| ATOM | 1708 | CG2 | ILE | 882 | 36.855 | −12.729 | 7.185  | 1.00 | 22.75 |
| ATOM | 1709 | CG1 | ILE | 882 | 35.749 | −11.006 | 8.675  | 1.00 | 22.91 |
| ATOM | 1710 | CD1 | ILE | 882 | 36.922 | −10.412 | 9.491  | 1.00 | 22.94 |
| ATOM | 1711 | C   | ILE | 882 | 37.668 | −10.643 | 5.340  | 1.00 | 24.48 |
| ATOM | 1712 | O   | ILE | 882 | 38.859 | −10.953 | 5.290  | 1.00 | 24.23 |
| ATOM | 1713 | N   | LYS | 883 | 36.908 | −10.541 | 4.256  | 1.00 | 25.73 |
| ATOM | 1714 | CA  | LYS | 883 | 37.441 | −10.868 | 2.945  | 1.00 | 28.25 |
| ATOM | 1715 | CB  | LYS | 883 | 36.492 | −11.820 | 2.211  | 1.00 | 27.47 |
| ATOM | 1716 | CG  | LYS | 883 | 35.140 | −11.240 | 1.932  | 1.00 | 27.17 |
| ATOM | 1717 | CD  | LYS | 883 | 34.293 | −12.163 | 1.109  | 1.00 | 27.60 |
| ATOM | 1718 | CE  | LYS | 883 | 32.926 | −11.544 | 0.899  | 1.00 | 28.94 |
| ATOM | 1719 | NZ  | LYS | 883 | 32.036 | −12.319 | −0.003 | 1.00 | 29.99 |
| ATOM | 1720 | C   | LYS | 883 | 37.749 | −9.657  | 2.061  | 1.00 | 30.08 |
| ATOM | 1721 | O   | LYS | 883 | 37.823 | −9.790  | 0.841  | 1.00 | 30.81 |
| ATOM | 1722 | N   | SER | 884 | 37.976 | −8.495  | 2.672  | 1.00 | 32.24 |
| ATOM | 1723 | CA  | SER | 884 | 38.268 | −7.260  | 1.938  | 1.00 | 33.66 |

TABLE A-continued

| | | | | | | | | |
|---|---|---|---|---|---|---|---|---|
| ATOM | 1724 | CB  | SER | 884 | 38.440 | −6.106  | 2.921  | 1.00 | 32.96 |
| ATOM | 1725 | OG  | SER | 884 | 39.466 | −6.384  | 3.856  | 1.00 | 32.02 |
| ATOM | 1726 | C   | SER | 884 | 39.500 | −7.349  | 1.042  | 1.00 | 35.48 |
| ATOM | 1727 | O   | SER | 884 | 39.491 | −6.867  | −0.087 | 1.00 | 35.08 |
| ATOM | 1728 | N   | HIS | 885 | 40.557 | −7.969  | 1.556  | 1.00 | 38.15 |
| ATOM | 1729 | CA  | HIS | 885 | 41.815 | −8.138  | 0.824  | 1.00 | 40.84 |
| ATOM | 1730 | CB  | HIS | 885 | 42.882 | −8.688  | 1.789  | 1.00 | 43.70 |
| ATOM | 1731 | CG  | HIS | 885 | 44.032 | −9.392  | 1.124  | 1.00 | 47.44 |
| ATOM | 1732 | CD2 | HIS | 885 | 44.240 | −10.707 | 0.860  | 1.00 | 49.14 |
| ATOM | 1733 | ND1 | HIS | 885 | 45.172 | −8.737  | 0.704  | 1.00 | 49.20 |
| ATOM | 1734 | CE1 | HIS | 885 | 46.034 | −9.615  | 0.217  | 1.00 | 49.74 |
| ATOM | 1735 | NE2 | HIS | 885 | 45.493 | −10.818 | 0.300  | 1.00 | 50.17 |
| ATOM | 1736 | C   | HIS | 885 | 41.682 | −9.017  | −0.432 | 1.00 | 41.12 |
| ATOM | 1737 | O   | HIS | 885 | 42.563 | −9.010  | −1.288 | 1.00 | 41.51 |
| ATOM | 1738 | N   | MET | 886 | 40.586 | −9.762  | −0.544 | 1.00 | 41.14 |
| ATOM | 1739 | CA  | MET | 886 | 40.372 | −10.639 | −1.686 | 1.00 | 41.17 |
| ATOM | 1740 | CB  | MET | 886 | 39.859 | −11.989 | −1.212 | 1.00 | 43.08 |
| ATOM | 1741 | CG  | MET | 886 | 40.928 | −12.860 | −0.584 | 1.00 | 45.59 |
| ATOM | 1742 | SD  | MET | 886 | 40.175 | −14.113 | −0.457 | 1.00 | 50.78 |
| ATOM | 1743 | CE  | MET | 886 | 39.069 | −14.971 | −0.725 | 1.00 | 48.51 |
| ATOM | 1744 | C   | MET | 886 | 39.455 | −10.074 | −2.761 | 1.00 | 40.68 |
| ATOM | 1745 | O   | MET | 886 | 39.535 | −14.476 | −3.923 | 1.00 | 41.66 |
| ATOM | 1746 | N   | VAL | 887 | 38.542 | −9.193  | −2.370 | 1.00 | 39.25 |
| ATOM | 1747 | CA  | VAL | 887 | 37.637 | −8.565  | −3.333 | 1.00 | 37.55 |
| ATOM | 1748 | CB  | VAL | 887 | 36.187 | −8.459  | −2.802 | 1.00 | 37.19 |
| ATOM | 1749 | CG1 | VAL | 887 | 35.526 | −9.828  | −2.756 | 1.00 | 37.49 |
| ATOM | 1750 | CG2 | VAL | 887 | 36.175 | −7.817  | −1.429 | 1.00 | 36.99 |
| ATOM | 1751 | C   | VAL | 887 | 38.145 | −7.168  | −3.702 | 1.00 | 37.08 |
| ATOM | 1752 | O   | VAL | 887 | 37.484 | −6.444  | −4.442 | 1.00 | 37.26 |
| ATOM | 1753 | N   | SER | 888 | 39.320 | −6.809  | −3.188 | 1.00 | 35.90 |
| ATOM | 1754 | CA  | SER | 888 | 39.955 | −5.515  | −3.437 | 1.00 | 35.05 |
| ATOM | 1755 | CB  | SER | 888 | 40.231 | −5.342  | −4.929 | 1.00 | 35.29 |
| ATOM | 1756 | OG  | SER | 888 | 41.335 | −6.133  | −5.326 | 1.00 | 36.74 |
| ATOM | 1757 | C   | SER | 888 | 39.216 | −4.290  | −2.898 | 1.00 | 34.27 |
| ATOM | 1758 | O   | SER | 888 | 39.402 | −3.179  | −3.396 | 1.00 | 34.78 |
| ATOM | 1759 | N   | VAL | 889 | 38.391 | −4.485  | −1.875 | 1.00 | 32.78 |
| ATOM | 1760 | CA  | VAL | 889 | 37.636 | −3.386  | −1.283 | 1.00 | 31.50 |
| ATOM | 1761 | CB  | VAL | 889 | 36.244 | −3.857  | −0.772 | 1.00 | 30.79 |
| ATOM | 1762 | CG1 | VAL | 889 | 35.509 | −2.729  | −0.055 | 1.00 | 30.12 |
| ATOM | 1763 | CG2 | VAL | 889 | 35.410 | −4.364  | −1.903 | 1.00 | 30.08 |
| ATOM | 1764 | C   | VAL | 889 | 38.410 | −3.002  | −0.064 | 1.00 | 31.36 |
| ATOM | 1765 | O   | VAL | 889 | 38.855 | −3.895  | 0.648  | 1.00 | 32.20 |
| ATOM | 1766 | N   | ASP | 890 | 38.692 | −1.724  | 0.156  | 1.00 | 31.10 |
| ATOM | 1767 | CA  | ASP | 890 | 39.364 | −1.428  | 1.414  | 1.00 | 30.80 |
| ATOM | 1768 | CB  | ASP | 890 | 40.849 | −1.093  | 1.296  | 1.00 | 33.89 |
| ATOM | 1769 | CG  | ASP | 890 | 41.720 | −1.949  | 2.261  | 1.00 | 35.96 |
| ATOM | 1770 | OD1 | ASP | 890 | 41.248 | −2.314  | 3.373  | 1.00 | 35.86 |
| ATOM | 1771 | OD2 | ASP | 890 | 42.882 | −2.260  | 1.901  | 1.00 | 37.33 |
| ATOM | 1772 | C   | ASP | 890 | 38.629 | −0.493  | 2.326  | 1.00 | 28.51 |
| ATOM | 1773 | O   | ASP | 890 | 37.889 | 0.379   | 1.889  | 1.00 | 27.96 |
| ATOM | 1774 | N   | PHE | 891 | 38.761 | −0.782  | 3.610  | 1.00 | 26.20 |
| ATOM | 1775 | CA  | PHE | 891 | 38.096 | −0.045  | 4.661  | 1.00 | 24.15 |
| ATOM | 1776 | CB  | PHE | 891 | 37.595 | −1.027  | 5.732  | 1.00 | 20.51 |
| ATOM | 1777 | CG  | PHE | 891 | 36.501 | −1.937  | 5.259  | 1.00 | 16.33 |
| ATOM | 1778 | CD1 | PHE | 891 | 36.741 | −2.892  | 4.288  | 1.00 | 15.42 |
| ATOM | 1779 | CD2 | PHE | 891 | 35.230 | −1.826  | 5.773  | 1.00 | 14.37 |
| ATOM | 1780 | CE1 | PHE | 891 | 35.720 | −3.370  | 3.832  | 1.00 | 13.60 |
| ATOM | 1781 | CE2 | PHE | 891 | 34.220 | −2.648  | 5.335  | 1.00 | 14.04 |
| ATOM | 1782 | CZ  | PHE | 891 | 34.467 | −3.607  | 4.353  | 1.00 | 13.43 |
| ATOM | 1783 | C   | PHE | 891 | 39.036 | 0.942   | 5.305  | 1.00 | 24.58 |
| ATOM | 1784 | O   | PHE | 891 | 40.150 | 0.574   | 5.695  | 1.00 | 25.30 |
| ATOM | 1785 | N   | PRO | 892 | 38.603 | 2.209   | 5.437  | 1.00 | 23.93 |
| ATOM | 1786 | CD  | PRO | 892 | 37.376 | 2.811   | 4.909  | 1.00 | 22.44 |
| ATOM | 1787 | CA  | PRO | 892 | 39.441 | 3.234   | 6.060  | 1.00 | 23.41 |
| ATOM | 1788 | CB  | PRO | 892 | 38.582 | 4.485   | 5.940  | 1.00 | 23.21 |
| ATOM | 1789 | CG  | PRO | 892 | 37.796 | 4.241   | 4.748  | 1.00 | 23.19 |
| ATOM | 1790 | C   | PRO | 892 | 39.655 | 2.866   | 7.520  | 1.00 | 23.31 |
| ATOM | 1791 | O   | PRO | 892 | 38.887 | 2.090   | 8.078  | 1.00 | 22.72 |
| ATOM | 1792 | N   | GLU | 893 | 40.619 | 3.517   | 8.157  | 1.00 | 24.55 |
| ATOM | 1793 | CA  | GLU | 893 | 40.984 | 3.267   | 9.555  | 1.00 | 26.50 |
| ATOM | 1794 | CB  | GLU | 893 | 41.885 | 4.385   | 10.072 | 1.00 | 28.90 |
| ATOM | 1795 | CG  | GLU | 893 | 42.329 | 4.192   | 11.509 | 1.00 | 33.98 |
| ATOM | 1796 | CD  | GLU | 893 | 42.441 | 5.498   | 12.280 | 1.00 | 37.38 |
| ATOM | 1797 | OE1 | GLU | 893 | 43.356 | 6.292   | 11.955 | 1.00 | 39.69 |
| ATOM | 1798 | OE2 | GLU | 893 | 41.624 | 5.729   | 13.216 | 1.00 | 39.34 |
| ATOM | 1799 | C   | GLU | 893 | 39.859 | 3.054   | 10.563 | 1.00 | 26.24 |
| ATOM | 1800 | O   | GLU | 893 | 39.750 | 1.992   | 11.180 | 1.00 | 27.29 |
| ATOM | 1801 | N   | MET | 894 | 39.052 | 4.078   | 10.782 | 1.00 | 26.07 |
| ATOM | 1802 | CA  | MET | 894 | 37.968 | 3.974   | 11.744 | 1.00 | 26.28 |

TABLE A-continued

| ATOM | 1803 | CB  | MET | 894 | 37.313 | 5.337  | 11.954 | 1.00 | 28.30 |
|------|------|-----|-----|-----|--------|--------|--------|------|-------|
| ATOM | 1804 | CG  | MET | 894 | 38.256 | 6.389  | 12.509 | 1.00 | 32.56 |
| ATOM | 1805 | SD  | MET | 894 | 38.847 | 5.925  | 14.144 | 1.00 | 38.01 |
| ATOM | 1806 | CE  | MET | 894 | 37.260 | 5.830  | 15.037 | 1.00 | 35.95 |
| ATOM | 1807 | C   | MET | 894 | 36.927 | 2.918  | 11.393 | 1.00 | 24.69 |
| ATOM | 1808 | O   | MET | 894 | 36.337 | 2.311  | 12.287 | 1.00 | 24.64 |
| ATOM | 1809 | N   | MET | 895 | 36.662 | 2.743  | 10.102 | 1.00 | 23.64 |
| ATOM | 1810 | CA  | MET | 895 | 35.705 | 1.738  | 9.645  | 1.00 | 22.83 |
| ATOM | 1811 | CB  | MET | 895 | 35.487 | 1.824  | 8.135  | 1.00 | 21.32 |
| ATOM | 1812 | CG  | MET | 895 | 34.669 | 3.006  | 7.693  | 1.00 | 21.17 |
| ATOM | 1813 | SD  | MET | 895 | 33.044 | 3.064  | 8.432  | 1.00 | 20.56 |
| ATOM | 1814 | CE  | MET | 895 | 32.088 | 2.305  | 7.205  | 1.00 | 22.81 |
| ATOM | 1815 | C   | MET | 895 | 36.171 | 0.328  | 10.032 | 1.00 | 22.26 |
| ATOM | 1816 | O   | MET | 895 | 35.469 | −0.383 | 10.714 | 1.00 | 22.26 |
| ATOM | 1817 | N   | ALA | 896 | 37.362 | −0.066 | 9.616  | 1.00 | 22.06 |
| ATOM | 1818 | CA  | ALA | 896 | 37.867 | −1.378 | 9.953  | 1.00 | 22.36 |
| ATOM | 1819 | CB  | ALA | 896 | 39.243 | −1.588 | 9.350  | 1.00 | 22.56 |
| ATOM | 1820 | C   | ALA | 896 | 37.914 | −1.581 | 11.460 | 1.00 | 22.96 |
| ATOM | 1821 | O   | ALA | 896 | 37.520 | −2.630 | 11.947 | 1.00 | 23.87 |
| ATOM | 1822 | N   | GLU | 897 | 38.377 | −0.586 | 12.212 | 1.00 | 23.92 |
| ATOM | 1823 | CA  | GLU | 897 | 38.455 | −0.724 | 13.666 | 1.00 | 24.05 |
| ATOM | 1824 | CB  | GLU | 897 | 39.128 | 0.502  | 14.313 | 1.00 | 25.98 |
| ATOM | 1825 | CG  | GLU | 897 | 39.288 | 0.390  | 15.841 | 1.00 | 27.50 |
| ATOM | 1826 | CD  | GLU | 897 | 39.150 | 1.718  | 16.555 | 1.00 | 27.88 |
| ATOM | 1827 | OE1 | GLU | 897 | 40.150 | 2.453  | 16.674 | 1.00 | 29.49 |
| ATOM | 1828 | OE2 | GLU | 897 | 38.036 | 2.018  | 17.013 | 1.00 | 29.22 |
| ATOM | 1829 | C   | GLU | 897 | 37.076 | −0.901 | 14.276 | 1.00 | 22.80 |
| ATOM | 1830 | O   | GLU | 897 | 36.873 | −1.774 | 15.094 | 1.00 | 22.95 |
| ATOM | 1831 | N   | ILE | 898 | 36.129 | −0.071 | 13.884 | 1.00 | 22.19 |
| ATOM | 1832 | CA  | ILE | 898 | 34.801 | −0.178 | 14.459 | 1.00 | 21.88 |
| ATOM | 1833 | CB  | ILE | 898 | 33.940 | 1.077  | 14.196 | 1.00 | 21.85 |
| ATOM | 1834 | CG2 | ILE | 898 | 32.478 | 0.836  | 14.587 | 1.00 | 22.66 |
| ATOM | 1835 | CG1 | ILE | 898 | 34.438 | 2.233  | 15.043 | 1.00 | 22.82 |
| ATOM | 1836 | CD1 | ILE | 898 | 33.490 | 3.390  | 15.019 | 1.00 | 23.11 |
| ATOM | 1837 | C   | ILE | 898 | 34.080 | −1.398 | 13.968 | 1.00 | 20.49 |
| ATOM | 1838 | O   | ILE | 898 | 33.228 | −1.917 | 14.656 | 1.00 | 21.90 |
| ATOM | 1839 | N   | ILE | 899 | 34.410 | −1.860 | 12.781 | 1.00 | 19.59 |
| ATOM | 1840 | CA  | ILE | 899 | 33.747 | −3.027 | 12.248 | 1.00 | 19.42 |
| ATOM | 1841 | CB  | ILE | 899 | 33.758 | −3.014 | 10.706 | 1.00 | 19.12 |
| ATOM | 1842 | CG2 | ILE | 899 | 33.095 | −4.285 | 10.157 | 1.00 | 18.71 |
| ATOM | 1843 | CG1 | ILE | 899 | 32.987 | −1.786 | 10.187 | 1.00 | 18.56 |
| ATOM | 1844 | CD1 | ILE | 899 | 33.054 | −1.588 | 8.683  | 1.00 | 15.05 |
| ATOM | 1845 | C   | ILE | 899 | 34.305 | −4.338 | 12.832 | 1.00 | 19.02 |
| ATOM | 1846 | O   | ILE | 899 | 33.571 | −5.300 | 12.982 | 1.00 | 19.98 |
| ATOM | 1847 | N   | SER | 900 | 35.565 | −4.344 | 13.233 | 1.00 | 19.03 |
| ATOM | 1848 | CA  | SER | 900 | 36.177 | −5.518 | 13.822 | 1.00 | 19.74 |
| ATOM | 1849 | CB  | SER | 900 | 37.614 | −5.631 | 13.340 | 1.00 | 19.62 |
| ATOM | 1850 | OG  | SER | 900 | 38.368 | −4.478 | 13.683 | 1.00 | 22.08 |
| ATOM | 1851 | C   | SER | 900 | 36.135 | −5.502 | 15.355 | 1.00 | 20.48 |
| ATOM | 1852 | O   | SER | 900 | 36.352 | −6.521 | 16.010 | 1.00 | 21.19 |
| ATOM | 1853 | N   | VAL | 901 | 35.866 | −4.346 | 15.939 | 1.00 | 20.99 |
| ATOM | 1854 | CA  | VAL | 901 | 35.808 | −4.235 | 17.396 | 1.00 | 20.43 |
| ATOM | 1855 | CB  | VAL | 901 | 36.705 | −3.074 | 17.927 | 1.00 | 20.22 |
| ATOM | 1856 | CG1 | VAL | 901 | 36.407 | −2.785 | 19.382 | 1.00 | 20.37 |
| ATOM | 1857 | CG2 | VAL | 901 | 38.168 | −3.436 | 17.782 | 1.00 | 18.81 |
| ATOM | 1858 | C   | VAL | 901 | 34.397 | −4.087 | 17.935 | 1.00 | 20.42 |
| ATOM | 1859 | O   | VAL | 901 | 33.999 | −4.823 | 18.841 | 1.00 | 21.68 |
| ATOM | 1860 | N   | GLN | 902 | 33.614 | −3.187 | 17.350 | 1.00 | 19.34 |
| ATOM | 1861 | CA  | GLN | 902 | 32.264 | −2.957 | 17.828 | 1.00 | 17.55 |
| ATOM | 1862 | CB  | GLN | 902 | 31.929 | −1.476 | 17.735 | 1.00 | 19.32 |
| ATOM | 1863 | CG  | GLN | 902 | 32.952 | −0.579 | 18.371 | 1.00 | 20.82 |
| ATOM | 1864 | CD  | GLN | 902 | 33.089 | −0.776 | 19.861 | 1.00 | 23.15 |
| ATOM | 1865 | OE1 | GLN | 902 | 32.211 | −1.336 | 20.528 | 1.00 | 23.22 |
| ATOM | 1866 | NE2 | GLN | 902 | 24.197 | −0.288 | 20.404 | 1.00 | 25.36 |
| ATOM | 1867 | C   | GLN | 902 | 31.145 | −3.766 | 17.207 | 1.00 | 16.24 |
| ATOM | 1868 | O   | GLN | 902 | 30.337 | −4.326 | 17.938 | 1.00 | 15.40 |
| ATOM | 1869 | N   | VAL | 903 | 31.075 | −3.810 | 15.872 | 1.00 | 15.79 |
| ATOM | 1870 | CA  | VAL | 903 | 30.025 | −4.552 | 15.144 | 1.00 | 15.22 |
| ATOM | 1871 | CB  | VAL | 903 | 30.195 | −4.461 | 13.594 | 1.00 | 14.30 |
| ATOM | 1872 | CG1 | VAL | 903 | 29.159 | −5.314 | 12.883 | 1.00 | 13.20 |
| ATOM | 1873 | CG2 | VAL | 903 | 30.012 | −3.005 | 13.147 | 1.00 | 14.90 |
| ATOM | 1874 | C   | VAL | 903 | 29.860 | −6.010 | 15.605 | 1.00 | 14.74 |
| ATOM | 1875 | O   | VAL | 903 | 28.732 | −6.489 | 15.693 | 1.00 | 14.48 |
| ATOM | 1876 | N   | PRO | 904 | 30.976 | −6.729 | 15.893 | 1.00 | 14.65 |
| ATOM | 1877 | CD  | PRO | 904 | 32.377 | −6.425 | 15.571 | 1.00 | 13.72 |
| ATOM | 1878 | CA  | PRO | 904 | 30.884 | −8.122 | 16.356 | 1.00 | 15.80 |
| ATOM | 1879 | CB  | PRO | 904 | 32.350 | −8.481 | 16.602 | 1.00 | 15.45 |
| ATOM | 1880 | CG  | PRO | 904 | 33.014 | −7.830 | 15.512 | 1.00 | 14.60 |
| ATOM | 1881 | C   | PRO | 904 | 30.053 | −8.206 | 17.632 | 1.00 | 16.77 |

TABLE A-continued

| | | | | | | | | |
|---|---|---|---|---|---|---|---|---|
| ATOM | 1882 | O | PRO | 904 | 29.151 | −9.039 | 17.713 | 1.00 | 18.38 |
| ATOM | 1883 | N | LYS | 905 | 30.286 | −7.295 | 18.589 | 1.00 | 17.00 |
| ATOM | 1884 | CA | LYS | 905 | 29.525 | −7.292 | 19.830 | 1.00 | 16.34 |
| ATOM | 1885 | CB | LYS | 905 | 29.866 | −6.085 | 20.668 | 1.00 | 18.17 |
| ATOM | 1886 | CG | LYS | 905 | 31.293 | −6.007 | 21.132 | 1.00 | 19.96 |
| ATOM | 1887 | CD | LYS | 905 | 31.464 | −4.733 | 21.947 | 1.00 | 22.09 |
| ATOM | 1888 | CE | LYS | 905 | 32.911 | −4.429 | 22.276 | 1.00 | 23.59 |
| ATOM | 1889 | NZ | LYS | 905 | 33.003 | −3.173 | 23.083 | 1.00 | 27.13 |
| ATOM | 1890 | C | LYS | 905 | 28.039 | −7.273 | 19.546 | 1.00 | 15.58 |
| ATOM | 1891 | O | LYS | 905 | 27.251 | −7.817 | 20.297 | 1.00 | 15.43 |
| ATOM | 1892 | N | ILE | 906 | 27.647 | −6.620 | 18.466 | 1.00 | 15.71 |
| ATOM | 1893 | CA | ILE | 906 | 26.239 | −6.554 | 18.086 | 1.00 | 15.74 |
| ATOM | 1894 | CB | ILE | 906 | 25.991 | −5.423 | 17.030 | 1.00 | 14.76 |
| ATOM | 1895 | CG2 | ILE | 906 | 24.527 | −5.427 | 16.565 | 1.00 | 13.47 |
| ATOM | 1896 | CG1 | ILE | 906 | 26.358 | −4.051 | 17.611 | 1.00 | 13.40 |
| ATOM | 1897 | CD1 | ILE | 906 | 26.021 | −2.876 | 16.686 | 1.00 | 13.18 |
| ATOM | 1898 | C | ILE | 906 | 25.800 | −7.899 | 17.748 | 1.00 | 17.05 |
| ATOM | 1899 | O | ILE | 906 | 24.759 | −8.471 | 17.834 | 1.00 | 16.35 |
| ATOM | 1900 | N | LEU | 907 | 26.609 | −8.385 | 16.539 | 1.00 | 17.95 |
| ATOM | 1901 | CA | LEU | 907 | 26.348 | −9.631 | 15.287 | 1.00 | 17.64 |
| ATOM | 1902 | CB | LEU | 907 | 27.331 | −9.787 | 14.659 | 1.00 | 15.32 |
| ATOM | 1903 | CG | LEU | 907 | 27.338 | −8.653 | 13.632 | 1.00 | 14.36 |
| ATOM | 1904 | CD1 | LEU | 907 | 28.382 | −8.885 | 12.557 | 1.00 | 12.28 |
| ATOM | 1905 | CD2 | LEU | 907 | 25.947 | −8.531 | 13.029 | 1.00 | 13.60 |
| ATOM | 1906 | C | LEU | 907 | 26.386 | −10.858 | 16.747 | 1.00 | 18.93 |
| ATOM | 1907 | O | LEU | 907 | 25.756 | −11.860 | 16.437 | 1.00 | 20.36 |
| ATOM | 1908 | N | SER | 908 | 27.097 | −10.805 | 17.868 | 1.00 | 19.02 |
| ATOM | 1909 | CA | SER | 908 | 27.103 | −11.947 | 18.772 | 1.00 | 19.60 |
| ATOM | 1910 | CB | SER | 908 | 28.469 | −12.099 | 19.407 | 1.00 | 19.21 |
| ATOM | 1911 | OG | SER | 908 | 28.811 | −10.944 | 20.135 | 1.00 | 19.20 |
| ATOM | 1912 | C | SER | 908 | 26.027 | −11.844 | 19.867 | 1.00 | 20.23 |
| ATOM | 1913 | O | SER | 908 | 25.946 | −12.709 | 20.752 | 1.00 | 20.86 |
| ATOM | 1914 | N | GLY | 909 | 25.208 | −10.791 | 19.812 | 1.00 | 19.30 |
| ATOM | 1915 | CA | GLY | 909 | 24.169 | −10.603 | 20.817 | 1.00 | 18.22 |
| ATOM | 1916 | C | GLY | 909 | 24.533 | −9.859 | 22.102 | 1.00 | 16.28 |
| ATOM | 1917 | O | GLY | 909 | 23.711 | −9.712 | 22.987 | 1.00 | 16.09 |
| ATOM | 1918 | N | LYS | 910 | 25.773 | −9.422 | 22.236 | 1.00 | 16.37 |
| ATOM | 1919 | CA | LYS | 910 | 26.166 | −8.670 | 23.411 | 1.00 | 17.37 |
| ATOM | 1920 | CB | LYS | 910 | 27.665 | −8.464 | 23.403 | 1.00 | 17.13 |
| ATOM | 1921 | CG | LYS | 910 | 28.418 | −9.703 | 23.684 | 1.00 | 16.32 |
| ATOM | 1922 | CD | LYS | 910 | 29.860 | −9.370 | 23.896 | 1.00 | 17.48 |
| ATOM | 1923 | CE | LYS | 910 | 30.577 | −10.534 | 24.482 | 1.00 | 17.90 |
| ATOM | 1924 | NZ | LYS | 910 | 32.055 | −10.284 | 24.502 | 1.00 | 19.93 |
| ATOM | 1925 | C | LYS | 910 | 25.472 | −7.296 | 23.532 | 1.00 | 18.68 |
| ATOM | 1926 | O | LYS | 910 | 25.250 | −6.797 | 24.640 | 1.00 | 19.51 |
| ATOM | 1927 | N | VAL | 911 | 25.219 | −6.641 | 22.397 | 1.00 | 18.99 |
| ATOM | 1928 | CA | VAL | 911 | 24.545 | −5.341 | 22.396 | 1.00 | 17.49 |
| ATOM | 1929 | CB | VAL | 911 | 25.501 | −4.130 | 22.041 | 1.00 | 17.52 |
| ATOM | 1930 | CG1 | VAL | 911 | 26.928 | −4.550 | 22.019 | 1.00 | 15.48 |
| ATOM | 1931 | CG2 | VAL | 911 | 25.094 | −3.412 | 20.788 | 1.00 | 15.48 |
| ATOM | 1932 | C | VAL | 911 | 23.379 | −5.475 | 21.458 | 1.00 | 17.48 |
| ATOM | 1933 | O | VAL | 911 | 23.504 | −6.015 | 20.358 | 1.00 | 17.40 |
| ATOM | 1934 | N | LYS | 912 | 22.219 | −5.032 | 21.896 | 1.00 | 17.96 |
| ATOM | 1935 | CA | LYS | 912 | 21.057 | −5.210 | 21.072 | 1.00 | 19.32 |
| ATOM | 1936 | CB | LYS | 912 | 20.189 | −6.325 | 21.672 | 1.00 | 21.17 |
| ATOM | 1937 | CG | LYS | 912 | 19.261 | −5.889 | 22.811 | 1.00 | 25.24 |
| ATOM | 1938 | CD | LYS | 912 | 19.998 | −5.297 | 24.030 | 1.00 | 26.63 |
| ATOM | 1939 | CE | LYS | 912 | 19.509 | −3.871 | 24.370 | 1.00 | 26.56 |
| ATOM | 1940 | NZ | LYS | 912 | 18.028 | −3.782 | 24.457 | 1.00 | 27.08 |
| ATOM | 1941 | C | LYS | 912 | 20.262 | −3.943 | 20.903 | 1.00 | 19.72 |
| ATOM | 1942 | O | LYS | 912 | 20.437 | −2.985 | 21.651 | 1.00 | 19.46 |
| ATOM | 1943 | N | PRO | 913 | 19.463 | −3.877 | 19.841 | 1.00 | 20.13 |
| ATOM | 1944 | CD | PRO | 913 | 19.437 | −4.660 | 18.599 | 1.00 | 20.38 |
| ATOM | 1945 | CA | PRO | 913 | 18.693 | −2.665 | 19.683 | 1.00 | 20.09 |
| ATOM | 1946 | CB | PRO | 913 | 18.174 | −2.780 | 18.259 | 1.00 | 20.97 |
| ATOM | 1947 | CG | PRO | 913 | 18.127 | −4.240 | 18.017 | 1.00 | 21.02 |
| ATOM | 1948 | C | PRO | 913 | 17.555 | −2.665 | 20.658 | 1.00 | 20.77 |
| ATOM | 1949 | O | PRO | 913 | 17.108 | −3.719 | 21.120 | 1.00 | 20.82 |
| ATOM | 1950 | N | ILE | 914 | 17.094 | −1.460 | 20.972 | 1.00 | 20.62 |
| ATOM | 1951 | CA | ILE | 914 | 15.965 | −1.262 | 21.846 | 1.00 | 18.90 |
| ATOM | 1952 | CB | ILE | 914 | 16.119 | 0.012 | 22.659 | 1.00 | 17.34 |
| ATOM | 1953 | CG1 | ILE | 914 | 14.953 | 0.149 | 23.589 | 1.00 | 15.42 |
| ATOM | 1954 | CG2 | ILE | 914 | 17.445 | −0.022 | 23.418 | 1.00 | 16.40 |
| ATOM | 1955 | CD1 | ILE | 914 | 17.794 | 1.261 | 24.098 | 1.00 | 15.82 |
| ATOM | 1956 | C | ILE | 914 | 14.823 | −1.093 | 20.858 | 1.00 | 19.73 |
| ATOM | 1957 | O | ILE | 914 | 14.946 | −0.313 | 19.909 | 1.00 | 20.71 |
| ATOM | 1958 | N | TYR | 915 | 13.774 | −1.908 | 20.995 | 1.00 | 19.80 |
| ATOM | 1959 | CA | TYR | 915 | 12.622 | −1.823 | 20.105 | 1.00 | 19.03 |
| ATOM | 1960 | CB | TYR | 915 | 12.194 | −3.193 | 19.566 | 1.00 | 18.88 |

TABLE A-continued

| ATOM | 1961 | CG | TYR | 915 | 13.072 | −3.773 | 18.505 | 1.00 | 18.76 |
|---|---|---|---|---|---|---|---|---|---|
| ATOM | 1962 | CD1 | TYR | 915 | 14.096 | −4.640 | 18.832 | 1.00 | 19.63 |
| ATOM | 1963 | CE1 | TYR | 915 | 14.923 | −5.170 | 17.853 | 1.00 | 21.76 |
| ATOM | 1964 | CD2 | TYR | 915 | 12.881 | −3.457 | 17.173 | 1.00 | 19.64 |
| ATOM | 1965 | CE2 | TYR | 915 | 13.698 | −3.989 | 16.177 | 1.00 | 20.92 |
| ATOM | 1966 | CZ | TYR | 915 | 14.721 | −4.839 | 16.531 | 1.00 | 21.98 |
| ATOM | 1967 | OH | TYR | 915 | 15.592 | −5.314 | 15.577 | 1.00 | 25.00 |
| ATOM | 1968 | C | TYR | 915 | 11.468 | −1.273 | 20.882 | 1.00 | 18.68 |
| ATOM | 1969 | O | TYR | 915 | 11.340 | −1.494 | 22.080 | 1.00 | 18.72 |
| ATOM | 1970 | N | PHE | 916 | 10.621 | −0.543 | 20.194 | 1.00 | 18.68 |
| ATOM | 1971 | CA | PHE | 916 | 9.456 | −0.019 | 20.836 | 1.00 | 19.66 |
| ATOM | 1972 | CB | PHE | 916 | 8.898 | 1.145 | 20.042 | 1.00 | 17.07 |
| ATOM | 1973 | CG | PHE | 916 | 9.567 | 2.411 | 20.335 | 1.00 | 14.89 |
| ATOM | 1974 | CD1 | PHE | 916 | 9.377 | 3.034 | 21.561 | 1.00 | 16.16 |
| ATOM | 1975 | CD2 | PHE | 916 | 10.393 | 2.992 | 19.407 | 1.00 | 16.16 |
| ATOM | 1976 | CE1 | PHE | 916 | 10.010 | 4.225 | 21.854 | 1.00 | 14.78 |
| ATOM | 1977 | CE2 | PHE | 916 | 11.028 | 4.183 | 19.689 | 1.00 | 16.01 |
| ATOM | 1978 | CZ | PHE | 916 | 10.836 | 4.800 | 20.916 | 1.00 | 15.28 |
| ATOM | 1979 | C | PHE | 916 | 8.451 | −1.148 | 20.868 | 1.00 | 21.60 |
| ATOM | 1980 | O | PHE | 916 | 7.862 | −1.434 | 21.910 | 1.00 | 22.04 |
| ATOM | 1981 | N | HIS | 917 | 8.300 | −1.804 | 19.718 | 1.00 | 22.86 |
| ATOM | 1982 | CA | HIS | 917 | 7.354 | −2.899 | 19.543 | 1.00 | 24.45 |
| ATOM | 1983 | CB | HIS | 917 | 6.549 | −2.696 | 18.258 | 1.00 | 23.60 |
| ATOM | 1984 | CG | HIS | 917 | 5.921 | −1.347 | 18.153 | 1.00 | 21.90 |
| ATOM | 1985 | CD2 | HIS | 917 | 6.440 | −0.153 | 17.787 | 1.00 | 21.97 |
| ATOM | 1986 | ND1 | HIS | 917 | 4.614 | −1.109 | 18.504 | 1.00 | 21.41 |
| ATOM | 1987 | CE1 | HIS | 917 | 4.350 | 0.178 | 18.360 | 1.00 | 22.05 |
| ATOM | 1988 | NE2 | HIS | 917 | 5.446 | 0.783 | 17.929 | 1.00 | 21.26 |
| ATOM | 1989 | C | HIS | 917 | 8.077 | −4.225 | 19.477 | 1.00 | 25.83 |
| ATOM | 1990 | OT1 | HIS | 917 | 9.185 | −4.257 | 18.908 | 1.00 | 27.53 |
| ATOM | 1991 | OT2 | HIS | 917 | 7.525 | −5.225 | 19.988 | 1.00 | 29.26 |
| ATOM | 1992 | C1 | DHT | 920 | 27.685 | 5.199 | 4.565 | 1.00 | 13.59 |
| ATOM | 1993 | C2 | DHT | 920 | 26.814 | 6.485 | 4.636 | 1.00 | 12.55 |
| ATOM | 1994 | C3 | DHT | 920 | 25.484 | 6.280 | 3.944 | 1.00 | 12.58 |
| ATOM | 1995 | O3 | DHT | 920 | 24.904 | 7.249 | 3.448 | 1.00 | 11.99 |
| ATOM | 1996 | C4 | DHT | 920 | 24.887 | 4.964 | 3.857 | 1.00 | 13.18 |
| ATOM | 1997 | C5 | DHT | 920 | 25.464 | 3.903 | 4.357 | 1.00 | 13.98 |
| ATOM | 1998 | C6 | DHT | 920 | 24.727 | 2.560 | 4.241 | 1.00 | 14.79 |
| ATOM | 1999 | C7 | DHT | 920 | 25.613 | 1.454 | 3.609 | 1.00 | 14.79 |
| ATOM | 2000 | C8 | DHT | 920 | 26.955 | 1.303 | 4.359 | 1.00 | 15.54 |
| ATOM | 2001 | C9 | DHT | 920 | 27.708 | 2.656 | 4.279 | 1.00 | 14.37 |
| ATOM | 2002 | C10 | DHT | 920 | 26.943 | 3.876 | 4.949 | 1.00 | 14.56 |
| ATOM | 2003 | C11 | DHT | 920 | 29.161 | 2.525 | 4.830 | 1.00 | 14.73 |
| ATOM | 2004 | C12 | DHT | 920 | 29.951 | 1.344 | 4.192 | 1.00 | 14.11 |
| ATOM | 2005 | C13 | DHT | 920 | 19.194 | −0.010 | 4.339 | 1.00 | 15.34 |
| ATOM | 2006 | C14 | DHT | 920 | 27.784 | 0.212 | 3.680 | 1.00 | 15.67 |
| ATOM | 2007 | C15 | DHT | 920 | 27.178 | −1.232 | 3.647 | 1.00 | 15.64 |
| ATOM | 2008 | C16 | DHT | 920 | 28.435 | −2.118 | 3.310 | 1.00 | 15.37 |
| ATOM | 2009 | C17 | DHT | 920 | 29.679 | −1.189 | 3.426 | 1.00 | 14.87 |
| ATOM | 2010 | C18 | DHT | 920 | 29.107 | −0.450 | 5.847 | 1.00 | 14.67 |
| ATOM | 2011 | C19 | DHT | 920 | 26.781 | 3.770 | 6.524 | 1.00 | 13.94 |
| ATOM | 2012 | O20 | DHT | 920 | 30.910 | −1.918 | 3.981 | 1.00 | 16.20 |
| ATOM | 2013 | O | HOH | 921 | 16.187 | 17.463 | 26.217 | 1.00 | 26.98 |
| ATOM | 2014 | O | HOH | 922 | 19.878 | 17.183 | 14.290 | 1.00 | 13.49 |
| ATOM | 2015 | O | HOH | 923 | 18.473 | 14.908 | 14.407 | 1.00 | 6.52 |
| ATOM | 2016 | O | HOH | 924 | 29.144 | 18.703 | 11.673 | 1.00 | 37.40 |
| ATOM | 2017 | O | HOH | 925 | 27.076 | 19.321 | 12.893 | 1.00 | 18.76 |
| ATOM | 2018 | O | HOH | 926 | 23.789 | 12.817 | 9.649 | 1.00 | 33.78 |
| ATOM | 2019 | O | HOH | 927 | 25.400 | 14.577 | 5.432 | 1.00 | 19.79 |
| ATOM | 2020 | O | HOH | 928 | 23.015 | 12.473 | 12.245 | 1.00 | 14.03 |
| ATOM | 2021 | O | HOH | 929 | 25.209 | 14.445 | 2.442 | 1.00 | 19.95 |
| ATOM | 2022 | O | HOH | 930 | 34.235 | 16.490 | 0.235 | 1.00 | 41.09 |
| ATOM | 2023 | O | HOH | 931 | 31.687 | 16.720 | 1.143 | 1.00 | 22.88 |
| ATOM | 2024 | O | HOH | 932 | 26.451 | 12.094 | 2.237 | 1.00 | 8.25 |
| ATOM | 2025 | O | HOH | 933 | 11.606 | −0.191 | −7.963 | 1.00 | 46.13 |
| ATOM | 2026 | O | HOH | 934 | 13.798 | 0.894 | 17.657 | 1.00 | 15.30 |
| ATOM | 2027 | O | HOH | 935 | 15.475 | 2.114 | 16.386 | 1.00 | 12.01 |
| ATOM | 2028 | O | HOH | 936 | 8.514 | −2.110 | 12.665 | 1.00 | 21.79 |
| ATOM | 2029 | O | HOH | 937 | 23.094 | 0.783 | 14.094 | 1.00 | 10.94 |
| ATOM | 2030 | O | HOH | 938 | 23.758 | −13.306 | 5.541 | 1.00 | 40.43 |
| ATOM | 2031 | O | HOH | 939 | 22.933 | −11.472 | 10.611 | 1.00 | 31.03 |
| ATOM | 2032 | O | HOH | 940 | 26.094 | −11.914 | 5.354 | 1.00 | 51.71 |
| ATOM | 2033 | O | HOH | 941 | 10.995 | −6.843 | 16.294 | 1.00 | 29.91 |
| ATOM | 2034 | O | HOH | 942 | 23.088 | 7.362 | −10.811 | 1.00 | 30.10 |
| ATOM | 2035 | O | HOH | 943 | 26.671 | 9.139 | −8.686 | 1.00 | 38.12 |
| ATOM | 2036 | O | HOH | 946 | 35.410 | −8.438 | −7.084 | 1.00 | 42.68 |
| ATOM | 2037 | O | HOH | 947 | 10.842 | 24.353 | 21.391 | 1.00 | 43.09 |
| ATOM | 2038 | O | HOH | 948 | 15.704 | 21.095 | 27.707 | 1.00 | 54.35 |
| ATOM | 2039 | O | HOH | 949 | 1.671 | 16.382 | 5.866 | 1.00 | 24.50 |

TABLE A-continued

| ATOM | 2040 | O | HOH | 950 | 8.009 | 20.744 | 8.572 | 1.00 | 36.16 |
|---|---|---|---|---|---|---|---|---|---|
| ATOM | 2041 | O | HOH | 951 | 29.490 | 17.190 | 30.961 | 1.00 | 56.26 |
| ATOM | 2042 | O | HOH | 952 | 23.829 | −12.134 | 35.596 | 1.00 | 39.41 |
| ATOM | 2043 | O | HOH | 953 | 42.457 | 5.523 | 7.132 | 1.00 | 28.93 |
| ATOM | 2044 | O | HOH | 954 | 41.318 | 2.323 | 2.406 | 1.00 | 38.22 |
| ATOM | 2045 | O | HOH | 955 | 25.857 | 7.152 | 30.722 | 1.00 | 18.97 |
| ATOM | 2046 | O | HOH | 956 | 18.191 | 16.505 | 27.701 | 1.00 | 29.01 |
| ATOM | 2047 | O | HOH | 957 | 14.018 | 2.408 | 20.246 | 1.00 | 18.75 |
| ATOM | 2048 | O | HOH | 958 | 14.651 | 4.006 | 17.873 | 1.00 | 21.70 |
| ATOM | 2049 | O | HOH | 959 | 5.786 | 11.770 | 15.499 | 1.00 | 35.58 |
| ATOM | 2050 | O | HOH | 960 | 2.694 | 19.497 | 9.834 | 1.00 | 25.35 |
| ATOM | 2051 | O | HOH | 961 | 0.334 | 6.151 | 20.624 | 1.00 | 27.66 |
| ATOM | 2052 | O | HOH | 962 | −2.677 | 2.639 | 17.420 | 1.00 | 35.67 |
| ATOM | 2053 | O | HOH | 963 | 0.868 | 8.543 | 25.138 | 1.00 | 43.49 |
| ATOM | 2054 | O | HOH | 964 | −8.085 | 7.667 | 23.358 | 1.00 | 40.82 |
| ATOM | 2055 | O | HOH | 965 | 6.749 | 1.200 | 9.766 | 1.00 | 24.57 |
| ATOM | 2056 | O | HOH | 966 | −0.636 | 8.734 | 6.585 | 1.00 | 40.09 |
| ATOM | 2057 | O | HOH | 967 | 22.487 | −4.734 | 14.335 | 1.00 | 28.04 |
| ATOM | 2058 | O | HOH | 968 | 18.615 | 17.070 | 7.167 | 1.00 | 23.83 |
| ATOM | 2059 | O | HOH | 969 | 10.049 | 19.612 | 2.716 | 1.00 | 28.02 |
| ATOM | 2060 | O | HOH | 970 | 26.829 | 21.030 | 22.736 | 1.00 | 25.40 |
| ATOM | 2061 | O | HOH | 971 | 23.684 | 9.361 | 5.898 | 1.00 | 24.06 |
| ATOM | 2062 | O | HOH | 972 | 23.124 | 15.837 | 0.189 | 1.00 | 29.07 |
| ATOM | 2063 | O | HOH | 973 | 34.079 | 8.287 | 19.446 | 1.00 | 34.35 |
| ATOM | 2064 | O | HOH | 974 | 37.522 | 2.898 | 1.092 | 1.00 | 22.39 |
| ATOM | 2065 | O | HOH | 975 | 21.838 | 14.392 | 5.445 | 1.00 | 20.42 |
| ATOM | 2066 | O | HOH | 976 | 16.106 | −10.859 | 0.784 | 1.00 | 48.09 |
| ATOM | 2067 | O | HOH | 977 | 11.295 | 27.231 | 20.742 | 1.00 | 24.50 |
| ATOM | 2068 | O | HOH | 978 | 21.562 | −7.923 | 18.100 | 1.00 | 34.94 |
| ATOM | 2069 | O | HOH | 979 | 41.647 | −2.962 | 5.907 | 1.00 | 41.33 |
| ATOM | 2070 | O | HOH | 981 | 12.897 | 22.682 | 24.398 | 1.00 | 44.10 |
| ATOM | 2071 | O | HOH | 982 | 33.709 | 13.619 | −5.931 | 1.00 | 26.84 |
| ATOM | 2072 | O | HOH | 983 | 0.019 | −4.834 | 14.164 | 1.00 | 36.91 |
| ATOM | 2073 | O | HOH | 984 | 39.563 | 3.365 | −2.334 | 1.00 | 36.56 |
| ATOM | 2074 | O | HOH | 985 | 16.244 | 18.091 | 7.952 | 1.00 | 25.52 |
| ATOM | 2075 | O | HOH | 986 | 13.038 | 13.790 | 19.688 | 1.00 | 21.93 |
| ATOM | 2076 | O | HOH | 987 | 22.095 | 3.621 | 21.834 | 1.00 | 19.27 |
| ATOM | 2077 | O | HOH | 988 | 2.516 | 2.235 | 3.905 | 1.00 | 30.91 |
| ATOM | 2078 | O | HOH | 989 | 2.950 | 1.064 | 1.716 | 1.00 | 31.16 |
| ATOM | 2079 | O | HOH | 990 | 5.186 | −1.082 | 5.207 | 1.00 | 26.66 |
| ATOM | 2080 | O | HOH | 991 | −0.310 | 15.229 | 24.529 | 1.00 | 28.42 |
| ATOM | 2081 | O | HOH | 992 | −6.181 | 9.210 | 18.935 | 1.00 | 37.84 |
| ATOM | 2082 | O | HOH | 993 | 17.408 | 26.662 | 14.814 | 1.00 | 30.32 |
| ATOM | 2083 | O | HOH | 994 | 17.401 | 31.211 | 13.007 | 1.00 | 30.57 |
| ATOM | 2084 | O | HOH | 995 | 21.268 | 22.961 | 10.009 | 1.00 | 33.92 |
| ATOM | 2085 | O | HOH | 996 | 26.335 | 12.379 | 6.567 | 1.00 | 36.58 |
| ATOM | 2086 | O | HOH | 997 | 33.730 | 15.077 | 4.345 | 1.00 | 24.42 |
| ATOM | 2087 | O | HOH | 998 | 28.576 | 2.290 | −15.305 | 1.00 | 30.54 |
| ATOM | 2088 | O | HOH | 999 | 33.926 | −5.402 | −13.979 | 1.00 | 48.01 |
| ATOM | 2089 | O | HOH | 1000 | 31.878 | −6.250 | −10.283 | 1.00 | 38.45 |
| ATOM | 2090 | O | HOH | 1021 | 30.673 | 18.487 | 18.256 | 1.00 | 34.16 |
| ATOM | 2091 | O | HOH | 1022 | 35.035 | 20.192 | 15.084 | 1.00 | 37.70 |
| ATOM | 2092 | O | HOH | 1023 | 32.791 | 17.836 | 19.423 | 1.00 | 35.34 |
| ATOM | 2093 | O | HOH | 1024 | 22.587 | −14.097 | 7.907 | 1.00 | 30.71 |
| ATOM | 2094 | O | HOH | 1025 | 29.778 | −9.620 | −0.255 | 1.00 | 24.68 |
| ATOM | 2095 | O | HOH | 1026 | 25.904 | 17.949 | 24.176 | 1.00 | 16.80 |
| ATOM | 2096 | O | HOH | 1027 | 33.066 | −13.092 | 7.455 | 1.00 | 20.84 |
| ATOM | 2097 | O | HOH | 1028 | 31.787 | 15.265 | 28.988 | 1.00 | 32.80 |
| ATOM | 2098 | O | HOH | 1029 | 27.029 | 0.835 | 13.994 | 1.00 | 20.01 |
| ATOM | 2099 | O | HOH | 1030 | 20.499 | 2.720 | 16.384 | 1.00 | 31.66 |
| ATOM | 2100 | O | HOH | 1031 | 10.991 | 16.858 | −1.085 | 1.00 | 30.58 |
| ATOM | 2101 | O | HOH | 1032 | 7.904 | 10.344 | −5.081 | 1.00 | 41.55 |
| ATOM | 2102 | O | HOH | 1033 | 12.570 | 3.398 | −10.099 | 1.00 | 26.95 |
| ATOM | 2103 | O | HOH | 1034 | 17.128 | 3.214 | −10.962 | 1.00 | 22.24 |
| ATOM | 2104 | O | HOH | 1035 | 17.056 | 1.547 | −4.553 | 1.00 | 26.98 |
| ATOM | 2105 | O | HOH | 1036 | 11.020 | 0.892 | 6.595 | 1.00 | 25.24 |
| ATOM | 2106 | O | HOH | 1037 | 3.092 | −1.135 | −0.025 | 1.00 | 27.44 |
| ATOM | 2107 | O | HOH | 1038 | 24.006 | 5.653 | 35.765 | 1.00 | 34.54 |
| ATOM | 2108 | O | HOH | 1039 | 29.738 | 0.950 | 27.680 | 1.00 | 26.47 |
| ATOM | 2109 | O | HOH | 1040 | 1.507 | 8.706 | 22.315 | 1.00 | 36.26 |
| ATOM | 2110 | O | HOH | 1041 | 10.755 | −4.751 | 9.776 | 1.00 | 27.77 |
| ATOM | 2111 | O | HOH | 1042 | 20.223 | −3.560 | 14.440 | 1.00 | 25.10 |
| ATOM | 2112 | O | HOH | 1043 | 30.147 | −9.103 | 2.467 | 1.00 | 26.08 |
| ATOM | 2113 | O | HOH | 1044 | 28.518 | −12.565 | −5.152 | 1.00 | 28.96 |
| ATOM | 2114 | O | HOH | 1045 | 39.044 | 7.751 | 17.961 | 1.00 | 38.02 |
| ATOM | 2115 | O | HOH | 1046 | 37.030 | 10.428 | 20.994 | 1.00 | 37.73 |

TABLE A-continued

| ATOM | 2116 | O | HOH | 1047 | 7.847 | -2.227 | 15.270 | 1.00 | 24.79 |
| ATOM | 2117 | O | HOH | 1048 | 9.958 | -5.351 | 21.522 | 1.00 | 40.62 |
| ATOM | 2118 | O | HOH | 1049 | 6.839 | -6.928 | 22.567 | 1.00 | 30.96 |

What is claimed is:

1. A crystal of an androgen receptor ligand binding domain (AR-LBD) consisting of amino acids 13 through 258 of SEQ ID NO:1 complexed with an AR-LBD ligand that is dihydroxytestosterone, said crystal belonging to the space group P212121 and having the unit cell dimensions a=56.03 angstrom, b=66.27 angstrom, and c=70.38 angstrom.

2. The crystal of claim 1 that has an AR-LBD ligand binding site defined by the structure coordinates of AR-LBD amino acids V685, L700, L701, S702, S703, L704, N705, E706, L707, G708, E709, Q711, A735, I737, Q738, Y739, S740, W742, M742, G743, L744, M745, V746, F747, A748, M749, G750, R752, Y763, F764, A765, L768, F770, M780, M787, I869, L873, H874, F876, T877 and F878 according to Table A.

3. The crystal of claim 1 that has an AR-LBD ligand binding site defined by the structure coordinates of AR-LBD amino acids N705, Q711, R752, F764 and T877 according to Table A.

* * * * *

```
                          SEQUENCE LISTING

<160> NUMBER OF SEQ ID NOS: 5

<210> SEQ ID NO 1
<211> LENGTH: 260
<212> TYPE: PRT
<213> ORGANISM: Rattus sp.

<400> SEQUENCE: 1

Gly Ser His Met Ile Glu Gly Tyr Glu Cys Gln Pro Ile Phe Leu Asn
1               5                   10                  15

Val Leu Glu Ala Ile Glu Pro Gly Val Val Cys Ala Gly His Asp Asn
                20                  25                  30

Asn Gln Pro Asp Ser Phe Ala Ala Leu Leu Ser Ser Leu Asn Glu Leu
            35                  40                  45

Gly Glu Arg Gln Leu Val His Val Val Lys Trp Ala Lys Ala Leu Pro
50                  55                  60

Gly Phe Arg Asn Leu His Val Asp Asp Gln Met Ala Val Ile Gln Tyr
65                  70                  75                  80

Ser Trp Met Gly Leu Met Val Phe Ala Met Gly Trp Arg Ser Phe Thr
                85                  90                  95

Asn Val Asn Ser Arg Met Leu Tyr Phe Ala Pro Asp Leu Val Phe Asn
            100                 105                 110

Glu Tyr Arg Met His Lys Ser Arg Met Tyr Ser Gln Cys Val Arg Met
            115                 120                 125

Arg His Leu Ser Gln Glu Phe Gly Trp Leu Gln Ile Thr Pro Gln Glu
        130                 135                 140

Phe Leu Cys Met Lys Ala Leu Leu Leu Phe Ser Ile Ile Pro Val Asp
145                 150                 155                 160

Gly Leu Lys Asn Gln Lys Phe Phe Asp Glu Leu Arg Met Asn Tyr Ile
                165                 170                 175

Lys Glu Leu Asp Arg Ile Ile Ala Cys Lys Arg Lys Asn Pro Thr Ser
            180                 185                 190

Cys Ser Arg Arg Phe Tyr Gln Leu Thr Lys Leu Leu Asp Ser Val Gln
        195                 200                 205

Pro Ile Ala Arg Glu Leu His Gln Phe Thr Phe Asp Leu Leu Ile Lys
    210                 215                 220

Ser His Met Val Ser Val Asp Phe Pro Glu Met Met Ala Glu Ile Ile
225                 230                 235                 240

Ser Val Gln Val Pro Lys Ile Leu Ser Gly Lys Val Lys Pro Ile Tyr
                245                 250                 255

Phe His Thr Gln
            260

<210> SEQ ID NO 2
<211> LENGTH: 255
<212> TYPE: PRT
<213> ORGANISM: Rattus sp.

<400> SEQUENCE: 2
```

```
Gly Gln Asp Ile Gln Leu Ile Pro Pro Leu Ile Asn Leu Leu Met Ser
1               5                   10                  15

Ile Glu Pro Asp Val Ile Tyr Ala Gly His Asp Asn Thr Lys Pro Asp
                20                  25                  30

Thr Ser Ser Ser Leu Leu Thr Ser Leu Asn Gln Leu Gly Glu Arg Gln
            35                  40                  45

Leu Leu Ser Val Val Lys Trp Ser Lys Ser Leu Pro Gly Phe Arg Asn
    50                  55                  60

Leu His Ile Asp Asp Gln Ile Thr Leu Ile Gln Tyr Ser Trp Met Ser
65                  70                  75                  80

Leu Met Val Phe Gly Leu Gly Trp Arg Ser Tyr Lys His Val Ser Gly
                85                  90                  95

Gln Met Leu Tyr Phe Ala Pro Asp Leu Ile Leu Asn Glu Gln Arg Met
                100                 105                 110

Lys Glu Ser Ser Phe Tyr Ser Leu Cys Leu Thr Met Trp Gln Ile Pro
            115                 120                 125

Gln Glu Phe Val Lys Leu Gln Val Ser Gln Glu Glu Phe Leu Cys Met
    130                 135                 140

Lys Val Leu Leu Leu Leu Asn Thr Ile Pro Leu Glu Gly Leu Arg Ser
145                 150                 155                 160

Gln Thr Gln Phe Glu Glu Met Arg Ser Ser Tyr Ile Arg Glu Leu Ile
                165                 170                 175

Lys Ala Ile Gly Leu Arg Gln Lys Gly Val Val Ser Ser Ser Gln Arg
                180                 185                 190

Phe Tyr Gln Leu Thr Lys Leu Leu Asp Asn Leu His Asp Leu Val Lys
            195                 200                 205

Gln Leu His Leu Tyr Cys Leu Asn Thr Phe Ile Gln Ser Arg Ala Leu
    210                 215                 220

Ser Val Glu Phe Pro Glu Met Met Ser Glu Val Ile Ala Ala Gln Leu
225                 230                 235                 240

Pro Lys Ile Leu Ala Gly Met Val Lys Pro Leu Leu Phe His Lys
                245                 250                 255

<210> SEQ ID NO 3
<211> LENGTH: 36
<212> TYPE: DNA
<213> ORGANISM: Artificial
<220> FEATURE:
<223> OTHER INFORMATION: Synthetic

<400> SEQUENCE: 3
catatgattg aaggctatga atgtcaacct atcttt                              36

<210> SEQ ID NO 4
<211> LENGTH: 24
<212> TYPE: DNA
<213> ORGANISM: Artificial
<220> FEATURE:
<223> OTHER INFORMATION: Synthetic

<400> SEQUENCE: 4
tcactgtgtg tggaaataga tggg                                           24

<210> SEQ ID NO 5
<211> LENGTH: 4
<212> TYPE: PRT
<213> ORGANISM: Artificial
<220> FEATURE:
```

```
<223> OTHER INFORMATION: Synthetic

<400> SEQUENCE: 5

Gly Ser His Met
```